US011541057B2

(12) United States Patent
Anderson et al.

(10) Patent No.: US 11,541,057 B2
(45) Date of Patent: *Jan. 3, 2023

(54) THIENOPYRIMIDINONE NMDA RECEPTOR MODULATORS AND USES THEREOF

(71) Applicant: Cadent Therapeutics, Inc., Cambridge, MA (US)

(72) Inventors: David R. Anderson, Salem, CT (US); Robert A. Volkmann, Mystic, CT (US); Frank S. Menniti, Mystic, CT (US); Christopher Fanger, Bolton, MA (US)

(73) Assignee: Cadent Therapeutics, Inc., Cambridge, MA (US)

( * ) Notice: Subject to any disclaimer, the term of this patent is extended or adjusted under 35 U.S.C. 154(b) by 14 days.

This patent is subject to a terminal disclaimer.

(21) Appl. No.: 17/186,137

(22) Filed: Feb. 26, 2021

(65) Prior Publication Data

US 2022/0016117 A1  Jan. 20, 2022

Related U.S. Application Data

(63) Continuation of application No. 16/929,602, filed on Jul. 15, 2020, now abandoned, which is a continuation of application No. 16/060,267, filed as application No. PCT/US2016/065855 on Dec. 9, 2016, now Pat. No. 10,973,825.

(60) Provisional application No. 62/265,187, filed on Dec. 9, 2015.

(51) Int. Cl.
*A61K 31/519* (2006.01)
*C07D 495/04* (2006.01)
*A61P 25/28* (2006.01)
*A61P 25/18* (2006.01)
*A61P 25/24* (2006.01)

(52) U.S. Cl.
CPC ............ *A61K 31/519* (2013.01); *A61P 25/18* (2018.01); *A61P 25/24* (2018.01); *A61P 25/28* (2018.01); *C07D 495/04* (2013.01)

(58) Field of Classification Search
CPC ............................. A61K 31/519; A61P 25/28
See application file for complete search history.

(56) References Cited

U.S. PATENT DOCUMENTS

| | | | |
|---|---|---|---|
| 4,921,854 | A | 5/1990 | Bozsing et al. |
| 6,852,731 | B2 | 2/2005 | Larsen et al. |
| 9,963,434 | B2 | 5/2018 | Anderson et al. |
| 10,500,205 | B2 | 12/2019 | Anderson et al. |
| 10,584,131 | B2 | 3/2020 | Anderson et al. |
| 10,626,122 | B2 | 4/2020 | Anderson et al. |
| 10,752,633 | B2 | 8/2020 | Anderson et al. |
| 10,973,825 | B2 | 4/2021 | Anderson et al. |
| 2002/0013329 | A1 | 1/2002 | Claremon et al. |
| 2007/0093509 | A1 | 4/2007 | Washburn et al. |
| 2008/0064678 | A1 | 3/2008 | Letourneau et al. |
| 2008/0090802 | A1 | 4/2008 | Letourneau et al. |
| 2008/0214553 | A1 | 9/2008 | Letourneau et al. |
| 2008/0280900 | A1 | 11/2008 | Pajouhesh et al. |
| 2010/0249087 | A1 | 9/2010 | Wang et al. |
| 2012/0165330 | A1 | 6/2012 | Vu |
| 2012/0178742 | A1 | 7/2012 | Henrich et al. |
| 2013/0123231 | A1 | 5/2013 | Harriman et al. |
| 2016/0222033 | A1 | 8/2016 | Yu et al. |
| 2017/0305861 | A1 | 10/2017 | Kim et al. |
| 2017/0313719 | A1 | 11/2017 | Traynelis et al. |
| 2020/0087323 | A1 | 3/2020 | Anderson et al. |
| 2021/0107916 | A1 | 4/2021 | Anderson et al. |

FOREIGN PATENT DOCUMENTS

| | | |
|---|---|---|
| AU | 2009243006 A1 | 11/2009 |
| AU | 2009266889 A1 | 1/2010 |
| CN | 102336768 A | 2/2012 |
| CN | 103664877 A | 3/2014 |
| JP | 2008-532981 A | 8/2008 |
| JP | 2010-502745 A | 1/2010 |
| JP | 2010-502746 A | 1/2010 |
| JP | 2013-507417 A | 3/2013 |
| JP | 2014-517833 A | 7/2014 |
| WO | WO-1998/00401 A1 | 1/1998 |
| WO | WO-2006/095014 A1 | 9/2006 |
| WO | WO-2008/033757 A2 | 3/2008 |
| WO | WO-2008/033764 A2 | 3/2008 |
| WO | WO-2008/076883 A2 | 6/2008 |
| WO | WO-2008/097538 A1 | 8/2008 |
| WO | WO-2008/128982 A1 | 10/2008 |
| WO | WO-2008/138126 A1 | 11/2008 |

(Continued)

OTHER PUBLICATIONS

Almasi et al., Characterization of potential NMDA and cholecystokinin antagonists II. Lipophilicity studies on 2-methyl-4-oxo-3H-quinazoline-3-alkyl-carboxylic acid derivatives. International Journal of Pharmaceutics. 1999;180:13-22.

Ciapetti et al., Molecular Variations Based on Isosteric Replacements. The Practice of Medicinal Chemistry, Third Edition. Camille Georges Wermuth (Ed.), Academic Press, Amsterdam. Chapter 15, pp. 290-342, (2008).

Ding et al., Parallel synthesis of 5-cyano-6-aryl-2-thiouracil derivatives as inhibitors for hepatitis C viral NS5B RNA-dependent RNA polymerase. Bioorg Chem. 2006;34(1):26-38.

Dotsenko et al., The Mannich reaction in the synthesis of N,S-containing heterocycles 5. Synthesis and structures of new pyrimido[2,1-b][1,3,5]thiadiazine derivatives. Russian Chemical Bulletin, International Edition. Jul. 2007;56(7):1437-1440.

(Continued)

*Primary Examiner* — Sahar Javanmard
(74) *Attorney, Agent, or Firm* — McCarter & English, LLP; Michael J. DeGrazia

(57) ABSTRACT

Disclosed herein, in part, are methods of treating neurological disorders, e.g., schizophrenia and major depressive disorder, comprising administering an effective amount of a disclosed heterocyclic compound. Pharmaceutical compositions and methods of making heteroaromatic compounds are provided. The compounds are contemplated to modulate the NMDA receptor.

9 Claims, No Drawings

(56) References Cited

FOREIGN PATENT DOCUMENTS

| WO | WO-2009/025784 A1 | 2/2009 |
|---|---|---|
| WO | WO-2009/062930 A1 | 5/2009 |
| WO | WO-2009/134973 A1 | 11/2009 |
| WO | WO-2009/146358 A1 | 12/2009 |
| WO | WO-2010/003048 A1 | 1/2010 |
| WO | WO-2010/037127 A1 | 4/2010 |
| WO | WO-2010/037129 A1 | 4/2010 |
| WO | WO-2010/079443 A1 | 7/2010 |
| WO | WO-2010/111573 A1 | 9/2010 |
| WO | WO-2010/139483 A1 | 12/2010 |
| WO | WO-2011/045258 A1 | 4/2011 |
| WO | WO-2011/117381 A1 | 9/2011 |
| WO | WO-2011/117382 A1 | 9/2011 |
| WO | WO-2012/052540 A1 | 4/2012 |
| WO | WO-2012/129562 A2 | 9/2012 |
| WO | WO-2012/154760 A1 | 11/2012 |
| WO | WO-2013/048928 A1 | 4/2013 |
| WO | WO-2013/048942 A1 | 4/2013 |
| WO | WO-2013/049104 A1 | 4/2013 |
| WO | WO-2014/139325 A1 | 9/2014 |
| WO | WO-2014/179144 A1 | 11/2014 |
| WO | WO-2014/206343 A1 | 12/2014 |
| WO | WO-2015/007453 A1 | 1/2015 |
| WO | WO-2015/096611 A1 | 7/2015 |
| WO | WO-2016/034703 A1 | 3/2016 |
| WO | WO-2016/081649 A1 | 5/2016 |
| WO | WO-2017/066590 A1 | 4/2017 |
| WO | WO-2017/100591 A1 | 6/2017 |
| WO | WO-2017/100593 A1 | 6/2017 |
| WO | WO-2017/100599 A1 | 6/2017 |
| WO | WO-2017/188694 A1 | 11/2017 |
| WO | WO-2018/026371 A1 | 2/2018 |
| WO | WO-2018/119374 A1 | 6/2018 |

OTHER PUBLICATIONS

El-Sherief et al., Intramolecular Cyclization of Mannich Reaction for Synthesis of Pyrimido[2,1-b]-1,3,5-tiadiazines. J Heterocyclic Chem. 2010;47:1294-1302.

Jia et al., Identification, design and bio-evaluation of novel Hsp90 inhibitors by ligand-based virtual screening. PLoS One. 2013;8(4):e59315, 15 pages.

Napier et al., Synthesis and SAR studies of novel 2-(6-aminomethylaryl-2-aryl-4-oxo-quinazolin-3(4H)-yl)acetamide vasopressin V1b receptor antagonists. Bioorg Med Chem Lett. Jun. 15, 2011;21(12):3813-7.

Nerkar et al., In Silico Design, Synthesis and Pharmacological Screening of Novel Mono and Di- Bromo Quinazolinone Derivatives as NMDA Receptor Antagonists for Anticonvulsant Activity. International Journal of Pharmacy and Pharmaceutical Sciences. 2013;5(1):331-335.

Noueiry et al., Identification of Novel Small-Molecule Inhibitors of West Nile Virus Infection. J Virol. Nov. 2007; 81(21):11992-12004.

PUBCHEM-CID 10587973, Create Date: Oct. 25, 2006, 9 pages.

PUBCHEM-CID 16957685, 8-(4-tert-butylphenyl)-6-oxo-3,4-dihydro-2H,6H-pyrimido[2,1-b][1,3]thiazine-7-carbonitrile. Create Date: Nov. 13, 2007, 7 pages.

PUBCHEM-CID 6612590, 7-phenyl-8H-[1,2,4]triazolo[4,3-a]pyrimidin-5-one. Create Date: Jun. 5, 2006, 8 pages.

Ram et al., 5-Cyano-6-aryluracil and 2-Thiouracil Derivatives as Potential Chemotherapeutic Agents. IV. J Heterocyclic Chem. Sep.-Oct. 1984;21:1307-1312.

Ram, Chemotherapeutic agents, XXI: Synthesis of Pi-deficient pyrimidines as leishmanicides. Arch Pharm (Weinheim). 1991;324(11):837-839.

Salem et al., Antioxidant Activity of Novel Fused Heterocyclic Compounds Derived from Tetrahydropyrimidine Derivative. Chem Pharm Bull (Tokyo). 2015;63(11):866-872.

Salem et al., Pyrimidinthiones (Part I): Utility of 2-Thioxopyrimidin-6-(1H)ones as Ring Transformer in the Synthesis of Fused Bi- and Tri-Cyclic Heterocyclic Compounds and Their Potential Biological Activities. Phosphorus, Sulfur, and Silicon. 2008;183:2596-2614.

Santangelo et al., Novel NMDA receptor modulators: an update. Expert Opin Ther Pat. Nov. 2012;22(11):1337-52.

Singh et al., Synthesis and Antiviral Activity of Some Novel N-Substituted Benzimidazolyl Annulated Pyrimidines. Journal of Indian Council of Chemists. 2008;25(1):19-22.

STN Registry No. 924249-59-2, Thieno[2,3-d]pyrimidin-4(3H)-one, 3-[3-(1-azetidinyl)-3-oxopropyl]-5-(4-methylphenyl)-, dated Mar. 2, 2007, 3 pages.

International Search Report for Application No. PCT/US2016/065855, dated Feb. 21, 2017, 4 pages.

THIENOPYRIMIDINONE NMDA RECEPTOR MODULATORS AND USES THEREOF

CROSS REFERENCE TO RELATED APPLICATIONS

This application is a continuation of U.S. application Ser. No. 16/929,602, filed Jul. 15, 2020, which is a continuation of U.S. application Ser. No. 16/060,267, filed Jun. 7, 2018, which is a 35 U.S.C. § 371 national stage filing of International Application Number PCT/US2016/065855, filed Dec. 9, 2016, which claims priority to U.S. Provisional Patent Application No. 62/265,187, filed Dec. 9, 2015, the entire contents of each of which are incorporated herein by reference.

BACKGROUND

Diseases of the nervous system are collectively the leading cause of human disability, as measured by the global burden of disease. Even those major diseases of the nervous system for which treatments have been approved by health authorities, including psychiatric diseases such as Schizophrenia, neurological diseases such as Alzheimer's Disease, and neurodevelopmental disorders, such as Attention Deficit and Hyperactivity Disorder, are poorly managed because approved treatments have limited efficacy and serious side effects, leaving a significant burden of unmet medical need. In addition, there are many major and rare nervous system disorders for which no treatments are approved, such as the neurodevelopmental disorders of the Autism Spectrum, and many intellectual disability disorders, and which are therefore associated with profound unmet medical need.

The N-methyl-D-aspartate-(NMDA) subtype of ligand-gated ion channel receptors are a diverse family of glutamate receptors widely accepted to mediate synaptic transmission, key mechanisms of synaptic plasticity, and dynamic neuronal network connectivity required for normal nervous system development and function.

The NMDA receptor is composed of four protein subunits, two GluN1 subunits and two GluN2 subunits. The GluN1 subunit is derived from a single gene (GRIN1), is ubiquitously expressed throughout the nervous system, and is common to all NMDA receptors. Four different GluN2 subunits, GluN2A-D, are derived from separate genes (GRIN2A-D) that are differentially expressed in different regions of the nervous system and by distinct populations of neurons within a particular region. A GluN3 subunit has also been identified, but its function is less well understood. Furthermore, individual neurons may express more than one GluN2 subunit and individual NMDA receptors expressed by such neurons may contain two of the same GluN2 subunits (for example, 2GluN2B subunits) or two different subunits (one GluN2A and one GluN2B subunit). In addition, all NMDA receptor subunits are expressed as diverse mRNA splice variants. Thus, native nervous system NMDA receptors are highly diverse in their composition.

The study of the molecular basis of NMDA receptor function continues to be an area of importance. As glutamate is the major excitatory neurotransmitter, dysfunction of glutamate neurotransmission and NMDA receptor-dependent mechanisms of synaptic transmission, plasticity, and neuronal network connectivity are broadly implicated in diseases of the nervous system. Accordingly, compounds that are capable of modulating NMDA receptors may be useful for the treatment of nervous system disorders and diseases, for example, schizophrenia, Alzheimer's disease, attention deficit and hyperactivity disorder, and autism.

SUMMARY

The present disclosure provides, at least in part, a method of treating a neurological disorder in a patient in need thereof, comprising administering an effective amount of a compound represented by Formula I:

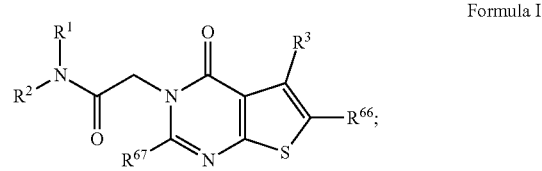

Formula I and pharmaceutically acceptable salts, stereoisomers and prodrugs thereof, where $R^1$, $R^2$, $R^3$, $R^{66}$, and $R^{67}$ are defined herein.

In particular, the present disclosure relates to a method for the treatment of psychiatric, neurologicial and/or neurodevelopmental disorders and/or diseases of the nervous system, for example, schizophrenia, Alzheimer's disease, attention deficit and hyperactivity, autism, and other nervous system-associated conditions. The disclosure provides, for example, a method of treating a neurological disorder in a patient in need thereof, comprising administering an effective amount of a compound which may be a modulator of NMDA receptors (e.g., positive allosteric modulators of NMDA receptors). The disclosure provides, for example, for the use of disclosed compounds as medicaments and/or in the manufacture of medicaments for the modulation of NMDA receptors in warm-blooded animals such as humans. Also contemplated herein are pharmaceutical compositions comprising at least one disclosed compound and a pharmaceutically acceptable excipient.

DETAILED DESCRIPTION

The features and other details of the disclosure will now be more particularly described. Before further description of the present disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

"Treating" includes any effect, e.g., lessening, reducing, modulating, or eliminating, that results in the improvement of the condition, disease, disorder and the like.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "carbonyl" as used herein refers to the radical —C(O)—.

The term "cyano" as used herein refers to the radical —CN.

The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine, etc.

The terms "heterocyclyl" or "heterocyclic group" are art-recognized and refer to saturated or partially unsaturated, 4-10 membered ring structures, including bridged or fused rings, and whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran, etc.

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to an OH functionality.

The term "oxo" as used herein refers to a carbonyl functionality (e.g., C=O).

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment of e.g., schizophrenia desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in substantially relief of symptoms associated with schizophrenia.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may be chiral or exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a stereogenic center implicitly. The present invention encompasses various stereoisomers of these compounds and mixtures thereof. Mixtures of enantiomers or diastereomers may be designated "(±)" in nomenclature, but the skilled artisan will recognize that a structure may denote a stereogenic center implicitly.

The compounds of the disclosure may contain one or more double bonds and, therefore, exist as geometric isomers resulting from the arrangement of substituents around a carbon-carbon double bond. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al., Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_{1-2})$alkylamino$(C_{2-3})$alkyl (such as β-dimethylaminoethyl), carbamoyl-$(C_{1-2})$alkyl, N,N-di) $C_{1-2}$)alkylcarbamoyl-$(C_{1-2})$alkyl and piperidino-, pyrrolidino- or morpholino$(C_{2-3})$alkyl.

Similarly, if a compound of the invention contains an alcohol functional group, a prodrug can be formed by the replacement of the hydrogen atom of the alcohol group with a group such as $(C_{1-6})$alkylcarbonyloxymethyl, 1-(($C_{1-6}$) alkylcarbonyloxy)ethyl, 1-methyl-1-(($C_{1-6}$)alkylcarbonyloxy)ethyl $(C_{1-6})$alkoxycarbonyloxymethyl, N-$(C_{1-6})$ alkoxycarbonylaminomethyl, succinoyl, $(C_{1-6})$ alkylcarbonyl, α-amino$(C_{1-4})$alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, $P(O)(OH)_2$, —$P(O)(O (C_{1-6})$alkyl$)_2$ or glycosyl (the radical resulting from the removal of a hydroxyl group of the hemiacetal form of a carbohydrate).

If a compound of the invention incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

In certain embodiments, the present disclosure provides a method of treating a neurological disorder in a patient in need thereof, comprising administering an effective amount of a compound represented by Formula I:

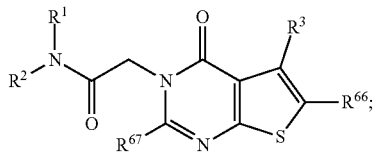

Formula I
and pharmaceutically acceptable salts, stereoisomers and prodrugs thereof, wherein:

$R^1$ and $R^2$ are each independently selected from the group consisting of hydrogen, $C_{1-4}$ alkyl, $C_{3-6}$ cycloalkyl, $C_{1-4}$alkoxy, and $C_{1-4}$ alkylcarbonyl; wherein $C_{1-4}$ alkyl, $C_{3-6}$ cycloalkyl, $C_{1-4}$alkoxy, and $C_{1-4}$ alkylcarbonyl may be optionally substituted on a carbon not bound to the nitrogen with one, two or three substituents each independently selected from halogen, hydroxyl, cyano, and $NR^aR^b$; or $R^1$ and $R^2$, together with the nitrogen to which they are attached, form a 3-7 membered heterocyclic ring which may have an additional heteroatom selected from O, S, or N; and wherein the 3-6 membered heterocyclic ring may optionally be substituted on carbon by one, two or more substituents each selected from the group consisting of: phenyl (optionally substituted by one, two or three halogens), $C_3$-$C_6$cycloalkyl (optionally substituted by one, two or three halogens), $C_{1-6}$alkoxy (optionally substituted by one, two or three halogens), and $C_{1-6}$alkyl (optionally substituted by one, two or three halogens), and on a carbon not bound to the nitrogen, by halogen, cyano, oxo, and hydroxyl;

$R^3$ is selected from the group consisting of phenyl, naphthyl, heteroaryl, heterocyclyl and $C_{3-6}$cycloalkyl; wherein $R^3$ may optionally be substituted with one, two or three substituents each independently selected from $C_{1-4}$alkyl, halogen, hydroxyl, cyano, $C_{1-4}$alkoxy, $C_{2-6}$alkenyl, $C_{2-6}$alkynyl, $C_{3-6}$cycloalkyl, $C_{1-6}$alkyl-S(O)$_2$—, $C_{1-6}$alkylcarbonyl, $R^aR^bN$—SO$_2$—, $NR^aR^b$, C(O)OH, $C_{1-4}$alkoxycarbonyl, and $NR^aR^b$carbonyl; and wherein $C_{1-4}$alkyl, $C_{1-4}$alkoxy, $C_{2-6}$alkenyl, $C_{2-6}$alkynyl, $C_{3-6}$cycloalkyl, $C_{1-6}$alkyl-S(O)$_2$—, and $C_{1-6}$alkylcarbonyl may be optionally substituted by one or more substituents each independently selected from halogen, hydroxyl, cyano, and $NR^aR^b$;

$R^{66}$ and $R^{67}$ are each independently selected from the group consisting of hydrogen, halogen, $C_{1-4}$alkyl (optionally substituted by one, two, three substituents selected from halogen, hydroxyl, cyano and $NR^aR^b$), and phenyl (optionally substituted by one, two or three halogens); and $R^a$ and $R^b$ are independently selected, for each occurrence, from the group consisting of hydrogen, hydroxyl, and $C_{1-3}$alkyl; or $R^a$ and $R^b$, together with the nitrogen to which they are attached, form a 4-6 membered heterocyclic ring which may have an additional heteroatom selected from O, S, or N.

In some embodiments, $R^1$ and $R^2$, together with the nitrogen to which they are attached, form a 4-6 membered heterocyclic ring optionally substituted on a carbon not adjacent to the nitrogen by one, two or more substituents each independently selected from the group consisting of halogen, cyano, oxo, hydroxyl and $C_{1-6}$alkyl (optionally substituted by one, two or three halogens).

In other embodiments, $R^3$ is selected from the group consisting of phenyl and heteroaryl; wherein $R^3$ is optionally substituted with one, two or three substituents each independently selected from the group consisting of $C_{1-4}$alkyl, halogen, hydroxyl, cyano, $C_{1-4}$alkoxy, $C_{2-6}$alkenyl, $C_{2-6}$alkynyl, $C_{3-6}$cycloalkyl, $C_{1-6}$alkyl-S(O)$_2$—, $C_{1-6}$alkylcarbonyl, $R^aR^bN$—SO$_2$—, $NR^aR^b$, C(O)OH, $C_{1-4}$alkoxycarbonyl, and $NR^aR^b$carbonyl; wherein $C_{1-4}$alkyl, $C_{1-4}$alkoxy, $C_{2-6}$alkenyl, $C_{2-6}$alkynyl, $C_{3-6}$cycloalkyl, $C_{1-6}$alkyl-S(O)$_2$—, and $C_{1-6}$alkylcarbonyl may be optionally substituted by one or more substituents each independently selected from halogen, hydroxyl, cyano, and $NR^aR^b$.

In some embodiments, a compound for use in the disclosed methods may be represented by:

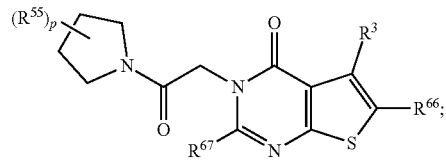

wherein

R$^{55}$ is selected from the group consisting of hydroxyl, fluorine, methyl, CF$_3$, phenyl and hydroxyl; and wherein p is 0, 1 or 2.

In other embodiments, a compound for use in the disclosed methods may be represented by:

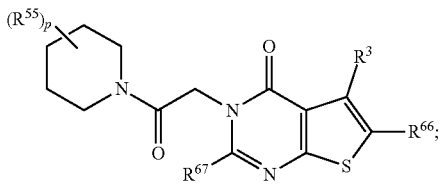

wherein

R$^{55}$ is selected from the group consisting of hydroxyl, fluorine, methyl, CF$_3$, phenyl and hydroxyl; and wherein p is 0, 1 or 2.

For example, R$^3$ is phenyl, pyrimidinyl or pyridinyl, each optionally substituted by one or two substituents each independently selected from halogen and C$_{1-3}$alkyl (optionally substituted by one, two or three halogens).

In some embodiments, a compound for use in the disclosed methods may be represented by:

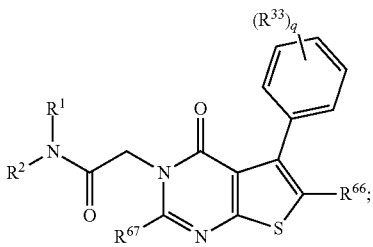

wherein

R$^{33}$ is selected from the group consisting of fluorine, chlorine, CF$_3$ and methyl; and wherein q is 0, 1, 2 or 3.

Also provided herein are methods of treating a neurological disorder in a patient in need thereof, comprising administering to the patient an effective amount of a compound represented by Formula II:

Formula II

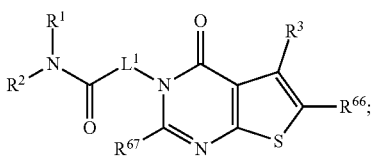

and pharmaceutically acceptable salts, stereoisomers and prodrugs thereof, wherein:

L$^1$ is selected from the group consisting of —(CR$^{11}$R$^{22}$)$_n$—, —O—, —NR$^a$—, —(CR$^{11}$R$^{22}$)$_n$NR$^a$—, —(CR$^{11}$R$^{22}$)$_n$O—, and —H(C=N)—;

R$^{11}$ and R$^{22}$ are each independently selected for each occurrence from the group consisting of hydrogen and C$_{1-4}$alkyl;

n is 1 or 2;

R$^1$ and R$^2$ are each independently selected from the group consisting of H, C$_{1-4}$ alkyl, C$_{3-6}$cycloalkyl, C$_{1-4}$alkoxy, and C$_{1-4}$ alkylcarbonyl (wherein C$_{1-4}$ alkyl, C$_{3-6}$cycloalkyl, C$_{1-4}$alkoxy, and C$_{1-4}$ alkylcarbonyl may be optionally substituted on a carbon not bound to the nitrogen with one, two or three substituents each independently selected from halogen, hydroxyl, cyano, and NR$^a$R$^b$) or R$^1$ and R$^2$, together with the nitrogen to which they are attached, form a 3-7 membered heterocyclic ring which may have an additional heteroatom selected from O, S, or N; and wherein the 3-6 membered heterocyclic ring may optionally be substituted on carbon by one, two or more substituents each selected from the group consisting of: phenyl (optionally substituted by one, two or three halogens), C$_3$-C$_6$cycloalkyl (optionally substituted by one, two or three halogens), C$_{1-6}$alkoxy (optionally substituted by one, two or three halogens), and C$_{1-6}$alkyl (optionally substituted by one, two or three halogens), and on a carbon not bound to the nitrogen, by halogen, cyano, oxo, and hydroxyl;

R$^3$ is selected from the group consisting of phenyl, naphthyl, heteroaryl, heterocyclyl and C$_{3-6}$cycloalkyl, wherein R$^3$ is optionally substituted with one, two or three substituents each independently selected from C$_{1-4}$alkyl, halogen, hydroxyl, cyano, C$_{1-4}$alkoxy, C$_{2-6}$alkenyl, C$_{2-6}$ alkynyl, C$_{3-6}$cycloalkyl, C$_{1-6}$alkyl-S(O)$_2$—, C$_{1-6}$alkylcarbonyl, R$^a$R$^b$N—SO$_2$—, NR$^a$R$^b$, C(O)OH, C$_{1-4}$alkoxycarbonyl, and NR$^a$R$^b$carbonyl, wherein C$_{1-4}$alkyl, C$_{1-4}$alkoxy, C$_{2-6}$alkenyl, C$_{2-6}$alkynyl, C$_{3-6}$cycloalkyl, C$_{1-6}$alkyl-S(O)$_2$—, and C$_{1-6}$alkylcarbonyl may be optionally substituted by one or more substituents each independently selected from halogen, hydroxyl, cyano, and NR$^a$R$^b$;

R$^{66}$ and R$^{67}$ are each independently selected from the group consisting of hydrogen, halogen, C$_{1-4}$ alkyl (optionally substituted by one, two, three substituents selected from halogen, hydroxyl, cyano and NR$^a$R$^b$), and phenyl (optionally substituted by one, two or three halogens); and R$^a$ and R$^b$ are independently selected, for each occurrence, from the group consisting of: hydrogen, hydroxyl, and C$_{1-3}$alkyl; or R$^a$ and R$^b$, together with the nitrogen to which they are attached, form a 4-6 membered heterocyclic ring which may have an additional heteroatom selected from O, S, or N.

In certain embodiments, L$^1$ may be —CH$_2$—.

Also provided herein are pharmaceutical compositions for use in treating a neurological disorder, comprising a compound of Formula II and a pharmaceutically acceptable excipient.

Procedures for making compounds of Formula I disclosed herein are provided below. In the reactions described below, it may be necessary to protect reactive functional groups (such as hydroxyl, amino, thio or carboxyl groups) to avoid their unwanted participation in the reactions. The incorporation of such groups, and the methods required to introduce and remove them are known to those skilled in the art (for example, see Greene, Wuts, Protective Groups in Organic Synthesis. 2nd Ed. (1999)). The deprotection step may be the final step in the synthesis such that the removal of protecting groups affords compounds of Formula I. Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

Compounds of of Formula I, as depicted above, or any of the intermediates described below, can be further derivatised by using one or more standard synthetic methods known to those skilled in the art. Such methods can involve substitution, oxidation or reduction reactions. These methods can also be used to obtain or modify compounds of Formula I or any preceding intermediates by modifying, introducing or removing appropriate functional groups. Particular substitution approaches include alkylation, arylation, heteroarylation, acylation, thioacylation, halogenation, sulfonylation, nitration, formylation, hydrolysis and coupling procedures. These procedures can be used to introduce a functional group onto the parent molecule (such as the nitration or sulfonylation of aromatic rings) or to couple two molecules together (for example to couple an amine to a carboxylic acid to afford an amide; or to form a carbon-carbon bond between two heterocycles). For example, alcohol or phenol groups can be converted to ether groups by coupling a phenol with an alcohol in a solvent (such as tetrahydrofuran) in the presence of a phosphine (such as triphenylphosphine) and a dehydrating agent (such as diethyl, diisopropyl or dimethyl azodicarboxylate). Alternatively, ether groups can be prepared by deprotonation of an alcohol, using a suitable base (such as sodium hydride) followed by the addition of an alkylating agent (such as an alkyl halide or an alkyl sulfonate).

In another example, a primary or secondary amine can be alkylated using a reductive alkylation procedure. For example, the amine can be treated with an aldehyde and a borohydride (such as sodium triacetoxyborohydride, or sodium cyanoborohydride in a solvent (such as a halogenated hydrocarbon, for example dichloromethane, or an alcohol, for example ethanol) and, where necessary, in the presence of an acid (such as acetic acid).

In another example, hydroxy groups (including phenolic OH groups) can be converted into leaving groups, such as halogen atoms or sulfonyloxy groups (such as alkylsulfonyloxy, for example trifluoromethanesulfonyloxy, or aryl suphonyloxy, for example p-toluenesulfonyloxy) using conditions known to those skilled in the art. For example, an aliphatic alcohol can be reacted with thionyl chloride in a halogenated hydrocarbon (such as dichloromethane) to afford the corresponding alkyl chloride. A base (such as triethylamine) can also be used in the reaction.

In another example, ester groups can be converted to the corresponding carboxylic acid group by acid- or base-catalysed hydrolysis depending on the nature of the ester group. Acid catalysed hydrolysis can be achieved by treatment with an organic or inorganic acid (such as trifluoroacetic acid in an aqueous solvent, or a mineral acid such as hydrochloric acid in a solvent such as dioxane). Base catalysed hydrolysis can be achieved by treatment with an alkali metal hydroxide (such as lithium hydroxide in an aqueous alcohol, for example methanol).

In another example, aromatic halogen substituents in the compounds may be subjected to halogen-metal exchange by treatment with a base (such as a lithium base, for example n-butyl or t-butyllithium) optionally at a low temperature (such as −78° C.) in a solvent (such as tetrahydrofuran) and the mixture may then be quenched with an electrophile to introduce a desired substituent. Thus, for example, a formyl group can be introduced by using dimethylformamide as the electrophile. Aromatic halogen substituents can also be subjected to palladium catalysed reactions to introduce groups such as carboxylic acids, esters, cyano or amino substituents.

In another example, an aryl, or heteroaryl ring substituted with an appropriate leaving group (such as a halogen or sulfonyl ester, for example a triflate) can undergo a palladium catalysed coupling reaction with a wide variety of substrates to form a carbon-carbon bond. For example, a Heck reaction can be used to couple such a ring system to an alkene (which may, or may not, be further substituted) by treatment with an organopalladium complex (such as tetrakis(triphenylphosphine)palladium(0), palladium (II) acetate or palladium (II) chloride) in the presence of a ligand (such as a phosphine, for example triphenylphosphine) in the presence of a base (such as potassium carbonate or a tertiary amine, for example, triethylamine), in an appropriate solvent (such as tetrahydrofuran or DMF), under appropriate conditions (such as heating to, for example, 50-120° C.). In another example, a Sonogashira reaction can be used to couple such a ring system to an alkyne (which may, or may not be further substituted) by treatment with a palladium complex (such as tetrakis(triphenylphosphine)palladium(0)) and a halide salt of copper (I) (such as copper (I) iodide), in the presence of a base (such as a potassium carbonate or a tertiary amine, for example, triethylamine), in an appropriate solvent (such as tetrahydrofuran or dimethylformamide), under appropriate conditions (such as heating to, for example, 50-120° C.). In another example, a Stille reaction can be used to couple such a ring system to an alkene, by treatment with an organotin compound (such as an alkynyltin or alkenyltin reagent, for example an alkenyltributylstannane) in the presence of a palladium complex (such as tetrakis(triphenylphosphine)palladium(0)), with, or without the presence of a salt (such as a copper (I) halide), in an appropriate solvent (such as dioxane or dimethylformamide), under appropriate conditions (such as heating to, for example, 50-120° C.).

Particular oxidation approaches include dehydrogenations and aromatisation, decarboxylation and the addition of oxygen to certain functional groups. For example, aldehyde groups can be prepared by oxidation of the corresponding alcohol using conditions well known to those skilled in the art. For example, an alcohol can be treated with an oxidising agent (such as Dess-Martin periodinane) in a solvent (such as a halogenated hydrocarbon, for example dichloromethane). Alternative oxidising conditions can be used, such as treatment with oxalyl chloride and an activating amount of dimethylsulfoxide and subsequent quenching by the addition of an amine (such as triethylamine). Such a reaction can be carried out in an appropriate solvent (such as a halogenated hydrocarbon, for example dichloromethane) and under appropriate conditions (such as cooling below room temperature, for example to −78° C. followed by warming to room temperature). In another example, sulfur atoms can be oxidised to the corresponding sulfoxide or sulfone using an oxidising agent (such as a peroxy acid, for example 3-chloroperoxybenzoic acid) in an inert solvent (such as a halogenated hydrocarbon, for example dichloromethane) at around ambient temperature.

Particular reduction approaches include the removal of oxygen atoms from particular functional groups or saturation (or partial saturation) of unsaturated compounds including aromatic or heteroaromatic rings. For example, primary alcohols can be generated from the corresponding ester or aldehyde by reduction, using a metal hydride (such as lithium aluminium hydride or sodium borohydride in a solvent such as methanol). Alternatively, $CH_2OH$ groups can be generated from the corresponding carboxylic acid by reduction, using a metal hydride (such as lithium aluminium hydride in a solvent such as tetrahydrofuran). In another example, a nitro group may be reduced to an amine by catalytic hydrogenation in the presence of a metal catalyst (such as palladium on a solid support such as carbon) in a solvent (such as an ether, for example tetrahydrofuran, or an alcohol, such as methanol), or by chemical reduction using a metal (such as zinc, tin or iron) in the presence of an acid (such as acetic acid or hydrochloric acid). In a further example an amine can be obtained by reduction of a nitrile, for example by catalytic hydrogenation in the presence of a metal catalyst (such as palladium on a solid support such as carbon), or Raney nickel in a solvent (such as tetrahydrofuran) and under suitable conditions (such as cooling to below room temperature, for example to −78° C., or heating, for example to reflux).

Salts of compounds of Formula I can be prepared by the reaction of a compound of Formula I with an appropriate acid or base in a suitable solvent, or mixture of solvents (such as an ether, for example, diethyl ether, or an alcohol, for example ethanol, or an aqueous solvent) using conventional procedures. Salts of compound of Formula I can be exchanged for other salts by treatment using conventional ion-exchange chromatography procedures.

Where it is desired to obtain a particular enantiomer of a compound of Formula I, this may be produced from a corresponding mixture of enantiomers by employing any suitable conventional procedure for resolving enantiomers. For example, diastereomeric derivatives (such as salts) can be produced by reaction of a mixture of enantiomers of a compound of Formula I (such a racemate) and an appropriate chiral compound (such as a chiral base). The diastereomers can then be separated by any conventional means such as crystallisation, and the desired enantiomer recovered (such as by treatment with an acid in the instance where the diastereomer is a salt). Alternatively, a racemic mixture of esters can be resolved by kinetic hydrolysis using a variety of biocatalysts (for example, see Patel Steroselective Biocatalysts, Marcel Decker; New York 2000).

In another resolution process a racemate of compounds of Formula I can be separated using chiral High Performance Liquid Chromatography. Alternatively, a particular enantiomer can be obtained by using an appropriate chiral intermediate in one of the processes described above. Chromatography, recrystallisation and other conventional separation procedures may also be used with intermediates or final products where it is desired to obtain a particular geometric isomer of the invention.

Methods

Another aspect of the disclosure provides methods of modulating the activity of the NMDA receptor. Such methods may for example, comprise exposing said receptor to a compound described herein. In some embodiments, the compound utilized by one or more of the foregoing methods is a compound of Formula I. The ability of compounds described herein to modulate the NMDA receptor can be evaluated by procedures known in the art and/or described herein.

In certain embodiments, the present disclosure provides a method of treating and or ameliorating a disease and/or disorder of the nervous system in a patient in need thereof by administering an effective amount of a disclosed compound. Exemplary diseases and disorders of the nervous system include psychiatric diseases, neurological diseases, and neurodevelopmental disorders, further described below.

In one embodiment, an exemplary psychiatric disease is schizophrenia. Schizophrenia is a debilitating mental disorder encompassing three symptom domains: positive (psychosis, hallucination, delusions), negative (withdrawal), and cognitive (global reduction in cognitive ability). Positive symptoms of Schizophrenia typically emerge early in adulthood and are treated with antipsychotic medications. However, cognitive deficits are severe, emerge in the adolescent prodromal stage, are resistant to antipsychotic therapy, and are the leading cause of lifetime disability as measured by impaired global function (inability to live independently, unemployment, etc). NMDA receptor hypofunction is the leading hypothesis for the cause of schizophrenia. This hypothesis is supported by substantial clinical evidence including clinical pharmacology, electrophysiology, imaging, cognition, computational neuroscience, neuroanatomical studies, and genetics. In particular, several lines of evidence implicate hypofunction of GluN2B-containing NMDA receptors in schizophrenia.

The present disclosure provides herein a method of treating schizophrenia, including positive, negative, and cognitive symptoms, in a patient in need thereof, comprising administering an effective amount of a disclosed compound. For example, provided herein are methods of ameloiorating positive, negative, and cognitive symptoms of a patient not adequately treated by approved antipsychotic medications, for example the treatment of cognitive impairments in schizophrenia, by administering an effective amount of a disclosed compound to such a patient.

Also provided herein are methods to improve cognitive and global function, and/or substantially preventing the onset of schizophrenia in people at risk of developing schizophrenia, by administering an effective amount of a disclosed compound to such a patient.

Contemplated herein are methods of treating and/or ameliorating cognitive and emotional deficits and other symptoms associated with exemplary psychiatric disorders including major depressive disorder, and including but not limited to those suffering from bipolar disorder, obsessive-compulsive disorder, dysphobic disorder, dysthymic disorder, psychotic depression, post-traumatic stress disorder, and other anxiety disorders. For example, provided herein are methods of treating attention deficit disorder, ADHD (attention deficit hyperactivity disorder), schizophrenia, anxiety, amelioration of opiate, nicotine and/or ethanol addiction (e.g., method of treating such addiction or ameliorating the side effects of withdrawing from such addiction), spinal cord injury, diabetic retinopathy, traumatic brain injury, and/or post-traumatic stress syndrome in a patient in need thereof, that includes administering a disclosed compound.

In other embodiments, provided herein is a method of treating and/or ameliorating cognitive and emotional deficits and other symptoms resulting from neurological diseases, including but not limited to a patient suffering from Alzheimer's disease, Parkinson's disease, Huntington's disease, amyotrophic lateral sclerosis, multiple sclerosis, and seizure disorders comprising administering to the patient an effective amount of a disclosed compound.

The present disclosure contemplates a method of treating and/or ameliorating dysfunction caused by neurodevelopmental disorders, e.g., abnormal brain development, including but not limited to Rett Syndrome, Attention Deficit and Hyperactivity Disorder, autism and autism spectrum disorders such as Phelan-McDermid Syndrome, and other forms of intellectual disability such as Fragile X syndrome, tuberous sclerosis, Smith-Lemli-Opitz Syndrome, and Down's syndrome. A method is also provided to treat patients suffering from abnormal brain function resulting from infections of the central nervous system, exposure to toxic agents or other xenobiotics or naturally occurring toxins, and/or autoimmune disorders including, but not limited to anti-NMDA receptor encephalitis comprising administering an effective amount of a disclosed compound.

In another aspect, the present disclosure provides herein a method of treating a central nervous system disorder in a patient in need thereof, comprising administering to the patient an effective amount of a disclosed compound, for example, a compound represented by Formula I or Formula II. Exemplary diseases and disorders of the central nervous system include but are not limited to, for example, arachnoid cysts, agnosia, ataxia, attention deficit/hyperactivity disorder (ADHD), autism, dislexia, bipolar disorders (for example, mania, acute mania, and bipolar depression), catalepsy, anxiety disorders (for example, generalized anxiety disorder, panic disorder, and social phobia), posttraumatic stress disorder, obsessive-compulsive disorder, depression, major deppressive disorder, seasonal affective disorder, dysthymia, neuropathic pain, schizophrenia, encephalitis, epilepsy, siezure, aphasia, expressive aphagia, hyperesthesia, paraesthesia, locked-in syndrome, migraine, Alzheimer's disease, Huntington's disease, Parkinson's disease, Pick disease, Creutzfeldt-Jakob Disease, dementia, Lewy body dementia, psychosis, Tourette's syndrome, Klüver-Bucy syndrome, Wernicke-Korsakoff syndrome, multiple sclerosis, amyotrophic lateral sclerosis, and sleep disorders (for example, primary and secondary insomnias, hypersomnias, and narcolepsy).

In particular, in certain embodiments, the disclosure provides a method of treating, preventing, and/or preventing the development of the above medical indications comprising administering to a subject in need thereof a therapeutically effective amount of a compound described herein, such as a compound of Formula I.

In certain embodiments, the compound utilized by one or more of the foregoing methods is one of the generic, subgeneric, or specific compounds described herein, such as a compound of Formula I.

Disclosed compounds may be administered to patients in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound of this invention may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment regimen can include a corrective phase, during which dose sufficient to maintain cognitive and/or emotional function is administered, and can be followed by a maintenance phase, during which a e.g. a lower dose sufficient to prevent a deficit in cognitive and/or emotional function is administered. A suitable maintenance dose is likely to be found in the lower parts of the dose ranges provided herein, but corrective and maintenance doses can readily be established for individual subjects by those of skill in the art without undue experimentation, based on the disclosure herein.

Pharmaceutical Compositions and Kits

Another aspect of the invention provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of the present disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the invention provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present invention.

Pharmaceutical compositions of the present disclosure may also be administered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxide-polylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Advantageously, the invention also provides kits for use by a e.g. a consumer in need of a disclosed NMDA modulator. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the invention.

$^1$H NMR spectral chemical shifts are expressed in ppm relative to tetramethylsilane. The following abbreviations have been used: br=broad signal, s=singlet, d=doublet, dd=double doublet, ddd=double double doublet, dt=double triplet, t=triplet, td=triple doublet, q=quartet, m=multiplet.

Example 1: Preparation of 5-(4-chlorophenyl)-3-(2-(4-hydroxypiperidin-1-yl)-2-oxoethyl)thieno[2,3-d]pyrimidin-4(3H)-one

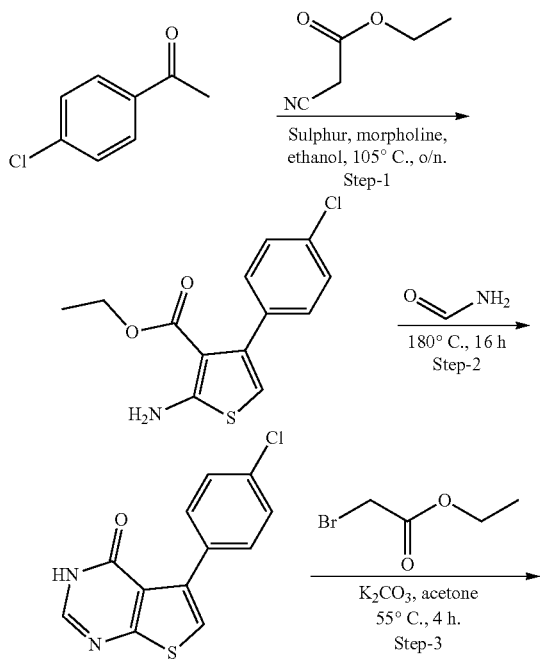

-continued

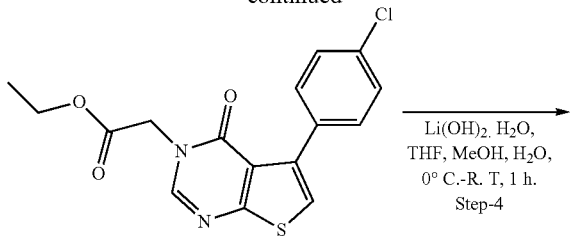

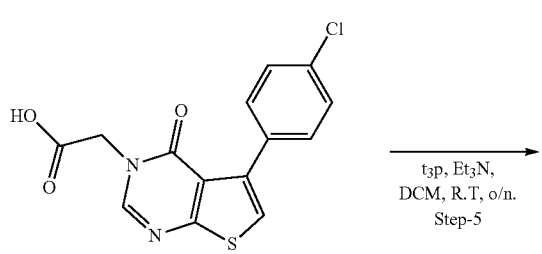

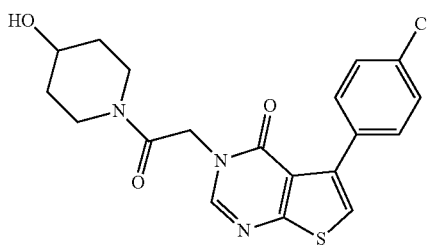

Step 1: Ethyl 2-amino-4-(4-chlorophenyl)thiophene-3-carboxylate

To a stirred solution of 1-(4-chlorophenyl)ethanone (30.0 g, 194.04 mmol) in ethanol (250 mL) was added ethyl 2-cyanoacetate (30.98 mL, 291 mmol), sulfur powder (8.09 g, 252.0 mml) and morpholine (33.47 mL, 388 mmol). The reaction mixture was refluxed for 18 h and was concentrated under reduced pressure. The crude product was purified by silica gel column chromatography using 10% ethyl acetate in hexane to afford ethyl 2-amino-4-(4-chlorophenyl)thiophene-3-carboxylate as a off-white solid (10.65 g, 19.5% yield).

Calculated (M+H): 282.03, Found (M+H): 282.1.

Step 2: 5-(4-chlorophenyl)thieno[2,3-d]pyrimidin-4(3H)-one

A mixture of ethyl 2-amino-4-(4-chlorophenyl)thiophene-3-carboxylate (10.6 g, 37.62 mmol) and formamide was heated at 190° C. for 16 h. The reaction mixture was cooled to room temperature and poured on to crushed ice and stirred for 30 minutes. The precipitated product was filtered, washed with water, dried to afford the title compound 5-(4-chlorophenyl)thieno[2,3-d]pyrimidin-4(3H)-one as a dark brown solid (7.74 g, 78.2% yield).

Calculated (M+H): 263.0; Found (M+H): 263.0.

Step 3: Ethyl 2-(5-(4-chlorophenyl)-4-oxothieno[2,3-d]pyrimidin-3(4H)-yl)acetate To a solution of 5-(4-chlorophenyl)thieno[2,3-d]pyrimidin-4(3H)-one (7.72 g, 29.39 mmol) in acetone (250 mL) was added potassium carbonate (12.19 g, 88.17 mmol) and ethyl-2-bromoacetate (6.52 mL, 58.77 mmol). The reaction mixture was heated at 55° C. for 16 h. After completion of the reaction, the reaction mixture was cooled to room temperature and filtered. The filtrate was concentrated under reduced pressure to afford crude product, which was purified by silica gel column chromatography using 10% ethyl acetate in hexane to afford ethyl 2-(5-(4-chlorophenyl)-4-oxothieno[2,3-d]pyrimidin-3(4H)-yl)acetate (10.51 g, crude) as a off-white solid.

Calculated (M+H): 349.03; Found (M+H): 349.0.

Step 4: 2-(5-(4-chlorophenyl)-4-oxothieno[2,3-d]pyrimidin-3(4H)-yl)acetic Acid To a solution of ethyl 2-(5-(4-chlorophenyl)-4-oxothieno[2,3-d]pyrimidin-3(4H)-yl)acetate (10.5 g, 30.1 mmol) in tetrahydrofuran:water mixture (100 mL, 1:1) was added lithium hydroxide monohydrate (6.31 g, 150.52 mmol) at room temperature and stirred at the same temperature for 1 h. After completion of the reaction, the reaction mixture was concentrated, the residue was diluted with water (50 mL) and acidified with 1.5N hydrochloric acid to pH 2 to 3. The precipitated product was filtered, washed with water and dried to afford 2-(5-(4-chlorophenyl)-4-oxothieno[2,3-d]pyrimidin-3(4H)-yl)acetic acid (9.1 g, 94.2% yield).

Calculated (M+H): 321.0; Found (M+H): 321.0.

Step 5: 5-(4-chlorophenyl)-3-(2-(4-hydroxypiperidin-1-yl)-2-oxoethyl)thieno[2,3-d]pyrimidin-4(3H)-one To a stirred solution of 2-(5-(4-chlorophenyl)-4-oxothieno[2,3-d]pyrimidin-3(4H)-yl)acetic acid (0.15 g, 0.46 mmol) in dichloromethane (10 mL) was added triethylamine (0.33 mL, 2.34 mmol) and piperidin-4-ol (0.14 g, 1.4 mmol) at room temperature. The reaction mixture was cooled to 0° C., 1-propylphosphonic anhydride (T3P) (0.42 mL, 0.93 mmol, 50% solution in ethyl acetate) was added and stirred at room temperature for 16 h. The reaction mixture was diluted with water (50 mL) and extracted with dichloromethane (2×50 mL). The combined organic layer was dried over anhydrous sodium sulfate, filtered and concentrated. The crude product was purified by silica gel column chromatography using 5% methanol in dichloromethane to afford 5-(4-chlorophenyl)-3-(2-(4-hydroxypiperidin-1-yl)-2-oxoethyl)thieno[2,3-d]pyrimidin-4(3H)-one as a white solid (0.04 g, 21.3% yield).

$^1$H NMR (400 MHz, DMSO-$d_6$) δ (ppm): 8.33 (s, 1H), 7.59 (s, 1H), 7.49 (d, J=8.4 Hz, 2H), 7.42 (d, J=8.4 Hz, 2H), 4.9 (s, 2H), 4.75 (d, J=3.6 Hz, 1H), 3.83-3.71 (m, 3H), 3.24 (t, J=10.0 Hz, 1H), 3.04 (t, J=9.6 Hz, 1H), 1.78 (brs, 1H), 1.67 (brs, 1H), 1.43-1.22 (m, 2H).

Calculated (M+H): 404.08, Found (M+H): 404.4.

HPLC purity: 99.79%.

Examples 2-19: The Following Compounds were Prepared by the Method Described Above

| Ex. No. | Structure | Analytical data |
|---|---|---|
| 2 | (4-fluoropiperidinyl acetyl) 5-(4-chlorophenyl)thieno[2,3-d]pyrimidin-4(3H)-one | ¹H NMR (400 MHz, DMSO-d₆) δ (ppm): 8.34 (s, 1H), 7.6 (s, 1H), 7.5 (d, J = 8.4 Hz, 2H), 7.43 (d, J = 8.4 Hz, 2H), 4.84-4.95 (m, 3H), 3.47-3.63 (m, 4H), 1.93-2.06 (m, 1H), 1.78 (brs, 2H), 1.64 (brs, 1H). Calculated (M + H): 406.07; Found (M + H): 406.1, HPLC purity: 99.18% |
| 3 | (4-methylpiperazinyl acetyl) 5-(4-chlorophenyl)thieno[2,3-d]pyrimidin-4(3H)-one | ¹H NMR (400 MHz, DMSO-d₆) δ (ppm): 8.33 (s, 1H), 7.59 (s, 1H), 7.49 (d, J = 8.4 Hz, 2H), 7.43 (d, J = 8.0 Hz, 2H), 4.91 (s, 2H), 3.5 (s, 2H), 3.42 (s, 2H), 2.36 (brs, 2H), 2.25 (brs, 2H), 2.19 (s, 3H); Calculated (M + H): 403.09, Found (M + H): 403.1, HPLC purity: 99.83% |
| 4 | (morpholinyl acetyl) 5-(4-chlorophenyl)thieno[2,3-d]pyrimidin-4(3H)-one | ¹H NMR (400 MHz, DMSO-d₆) δ (ppm): 8.33 (s, 1H), 7.60 (s, 1H), 7.50 (d, J = 8.4 Hz, 2H), 7.43 (d, J = 8.4 Hz, 2H), 4.92 (s, 2H), 3.63 (s, 2H), 3.54 (bs, 4H), 3.41 (bs, 2H). Calculated (M + H): 390.06; Found (M + H): 390.4, HPLC purity: 99.62% |
| 5 | (cyclopropylamino acetyl) 5-(4-chlorophenyl)thieno[2,3-d]pyrimidin-4(3H)-one | ¹H NMR (400 MHz, DMSO-d₆) δ (ppm): 8.36 (s, 1H), 8.31 (d, J = 3.6 Hz, 1H), 7.59 (s, 1H), 7.51 (d, J = 8.4 Hz, 2H), 7.43 (d, J = 8.0 Hz, 2H), 4.54 (s, 2H), 2.65-2.59 (m, 1H), 0.63-0.58 (m, 2H), 0.40-0.39 (m, 2H). Calculated (M + H): 360.05, Found (M + H): 360.3, HPLC purity: 99.10% |
| 6 | (3-hydroxypyrrolidinyl acetyl) 5-(4-chlorophenyl)thieno[2,3-d]pyrimidin-4(3H)-one | ¹H NMR (400 MHz, DMSO-d₆) δ (ppm): 8.34 (s, 1H), 7.59 (s, 1H), 7.50 (d, J = 8.4 Hz, 2H), 7.30 (d, J = 8.4 Hz, 2H), 5.07-4.94 (m, 1H), 4.86-4.72 (m, 2H), 4.25-4.37 (m, 1H), 3.49-3.61 (m, 2H), 3.44-3.23 (m, 2H), 2.1-1.75 (m, 2H). Calculated (M + H): 390.06, Found (M + H): 390.3, HPLC purity: 99.58% |

| Ex. No. | Structure | Analytical data |
|---|---|---|
| 7 | 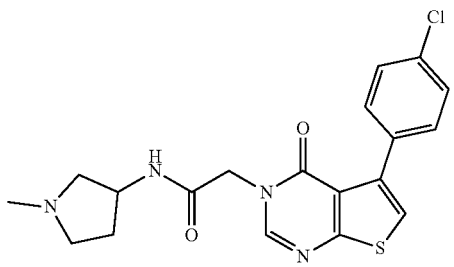 [SMILES: CN1CCC(NC(=O)Cn2cnc3scc(-c4ccc(Cl)cc4)c3c2=O)C1] | ¹H NMR (400 MHz, DMSO-d₆) δ (ppm): 8.5 (d, J = 6.4 Hz, 1H), 8.36 (s, 1H), 7.59 (s, 1H), 7.51 (d, J = 8.4 Hz, 2H), 7.43 (d, J = 8.4 Hz, 2H), 4.60 (s, 2H), 4.18-4.14 (m, 1H), 2.78-2.76 (m, 2H), 2.49 (brs, 1H), 2.37 (s, 3H), 2.17-2.07 (m, 1H), 1.65-1.61 (m, 1H), 1.34-1.22 (1H). Calculated (M + H): 403.09, Found (M + H): 403.1, HPLC Purity: 98.91% |
| 8 | 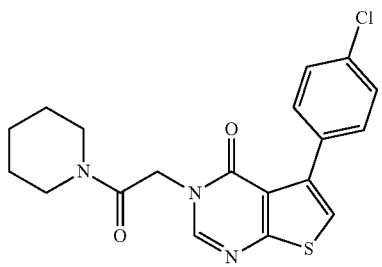 | ¹H NMR (400 MHz, DMSO-d₆) δ (ppm): 8.38 (s, 1H), 7.59 (s, 1H), 7.50 (d, J = 8.4 Hz, 2H), 7.43 (d J = 8.4 Hz, 2H), 4.89 (s, 2H), 3.46 (brs, 2H), 3.40 (brs, 2H), 1.58 (brs, 4H), 1.43 (brs, 2H). Calculated (M + H): 388.08, Found (M + H): 388.1, HPLC purity: 99.68% |
| 9 | 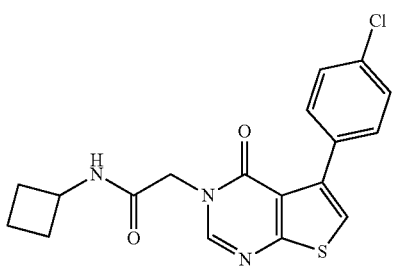 [SMILES: O=C(Cn1cnc2scc(-c3ccc(Cl)cc3)c2c1=O)NC1CCC1] | ¹H NMR (400 MHz, DMSO-d₆) δ (ppm): 8.49 (d, J = 7.6 Hz, 1H), 8.35 (s, 1H), 7.58 (s, 1H), 7.50 (d, J = 8.4 Hz, 2H), 7.42 (d, J = 8.4 Hz, 2H), 4.56 (s, 2H), 4.19-4.11 (m, 1H), 2.14-2.10 (m, 2H), 1.92-1.82 (m, 2H), 1.64-1.55 (m, 2H). Calculated (M + H): 374.07, Found (M + H): 374.1, HPLC purity: 98.35% |
| 10 | 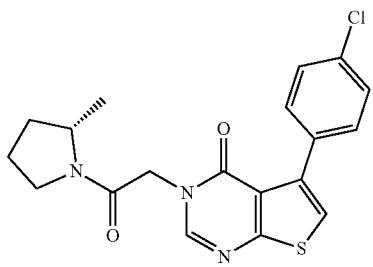 [SMILES: C[C@H]1CCCN1C(=O)Cn1cnc2scc(-c3ccc(Cl)cc3)c2c1=O] | ¹H NMR (400 MHz, DMSO-d₆) δ (ppm): 8.37-8.33 (m, 1H), 7.59-7.58 (m, 1H), 7.51-7.48 (m, 2H), 7.44-7.42 (m, 2H), 4.91 (m, 2H), 4.19-3.97 (m, 1H), 3.60-3.44 (m, 2H), 2.02-1.52 (m, 4H), 1.21 (d, J = 6.4 Hz, 1H), 1.07 (t, J = 14.4 Hz, 2H). Calculated (M + H): 388.08, Found (M + H): 388.1, HPLC purity: 99.12% |
| 11 | 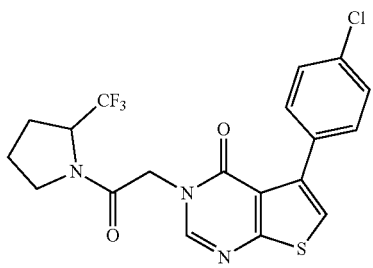 [SMILES: O=C(Cn1cnc2scc(-c3ccc(Cl)cc3)c2c1=O)N1CCCC1C(F)(F)F] | ¹H NMR (400 MHz, DMSO-d₆) δ (ppm): 8.38-8.35 (m, 1H), 7.61 (s, 1H), 7.50 (d, J = 8.0 Hz, 2H), 7.43 (d, J = 8.4 Hz, 2H), 5.09-4.80 (m, 3H), 4.73-4.69 (m, 1H), 3.67-3.59 (m, 2H), 2.18-1.91 (m, 3H). Calculated (M + H): 442.05, Found (M + H): 442.1, HPLC purity: 99.72% |

| Ex. No. | Structure | Analytical data |
|---|---|---|
| 12 | (2,6-dimethylpiperidine acetyl linked to 5-(4-chlorophenyl)thieno[2,3-d]pyrimidin-4(3H)-one) | $^1$H NMR (400 MHz, DMSO-d$_6$) δ (ppm): 8.34-8.33 (m, 1H), 7.59 (s, 1H), 7.49 (d, J = 8.4 Hz, 2H), 7.42 (d, J = 8.4 Hz, 2H), 4.96-4.83 (m, 2H), 4.23 (d, J = 11.2 Hz, 1H), 3.83 (d, J = 12.8 Hz, 1H), 3.48 (d, J = 13.2 Hz, 1H), 3.16-3.03 (m, 1H), 2.65-2.49 (m, 1H), 2.06 (t, J = 12.4 Hz, 1H), 1.93-1.61 (m, 2H), 0.99-0.74 (m, 6H). Calculated (M + H): 416.11, Found (M + H): 416.0, HPLC purity: 97.77% |
| 13 | (N,N-diethylacetamide linked to 5-(4-chlorophenyl)thieno[2,3-d]pyrimidin-4(3H)-one) | $^1$H NMR (400 MHz, DMSO-d$_6$,) δ (ppm): 8.36 (s, 1H), 7.58 (s, 1H), 7.50 (d, J = 8.4 Hz, 2H), 7.43 (d, J = 8.4 Hz, 2H), 4.87 (s, 2H), 3.41-3.36 (m, 2H), 3.28-3.23 (m, 2H), 1.19 (t, J = 7.2 Hz, 3H), 1.00 (t, J = 7.2 Hz, 3H). Calculated (M + H): 376.08, Found (M + H): 376.1, HPLC purity: 99.27% |
| 14 | (4,4-difluoropiperidine acetyl linked to 5-(4-chlorophenyl)thieno[2,3-d]pyrimidin-4(3H)-one) | $^1$H NMR (400 MHz, DMSO-d$_6$) δ (ppm): 8.32 (s, 1H), 7.60 (s, 1H), 7.50 (d, J = 8.4 Hz, 2H), 7.42 (d, J = 8.4 Hz, 2H), 4.98 (s, 2H), 3.63 (brs, 2H), 3.55 (brs, 2H), 2.10-2.06 (brs, 2H), 2.92 (brs, 2H). Calculated (M + H): 424.06, Found (M + H): 424.0 HPLC purity: 99.48% |
| 15 | (4-hydroxy-4-phenylpiperidine acetyl linked to 5-(4-chlorophenyl)thieno[2,3-d]pyrimidin-4(3H)-one) | $^1$H NMR (400 MHz, DMSO-d$_6$) δ (ppm): 8.37 (s, 1H), 7.60 (s, 1H), 7.52-7.42 (m, 6H), 7.32 (t, J = 7.2 Hz, 2H), 7.22 (t, J = 7.2 Hz, 1H), 5.16 (s, 1H), 4.96 (s, 2H), 4.21 (d, J = 12.0 Hz, 1H), 3.84 (d, J = 12.8 Hz, 1H), 3.50 (t, J = 12.4 Hz, 1H), 3.03 (t, J = 12.0 Hz, 1H), 2.06-2.00 (m, 1H), 1.80-1.75 (m, 1H), 1.69-1.60 (m, 2H). Calculated (M + H): 480.11, Found (M + H): 481.1, HPLC purity: 99.25% |
| 16 | (3-fluoropyrrolidine acetyl linked to 5-(4-chlorophenyl)thieno[2,3-d]pyrimidin-4(3H)-one) | $^1$H NMR (400 MHz, DMSO-d$_6$) δ (ppm): 8.35 (s, 1H), 7.60 (s, 1H), 7.50 (d, J = 8.4 Hz, 2H), 7.42 (d, J = 8.4 Hz, 2H), 5.38 (t, J = 48.4 Hz, 1H), 4.92-4.75 (m, 2H), 4.12-3.33 (m, 4H), 2.31-1.94 (m, 2H). Calculated (M + H): 392.06, Found (M + H): 392.1, HPLC purity: 99.16% |

| Ex. No. | Structure | Analytical data |
|---|---|---|
| 17 | 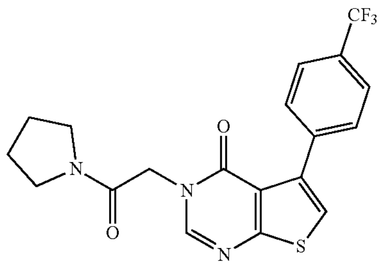 [SMILES: O=C(Cn1cnc2scc(-c3ccc(C(F)(F)F)cc3)c2c1=O)N1CCCC1] | $^1$H NMR (400 MHz, DMSO-$d_6$) δ (ppm): 8.36 (s, 1H), 7.74-7.70 (m, 5H), 4.80 (s, 2H), 3.50 (brs, 2H), 3.29 (brs, 2H), 1.94-1.91 (m, 2H), 1.79-1.76 (m, 2H). Calculated (M + H): 408.09. Found (M + H): 408.1, HPLC purity: 98.72% |
| 18 | 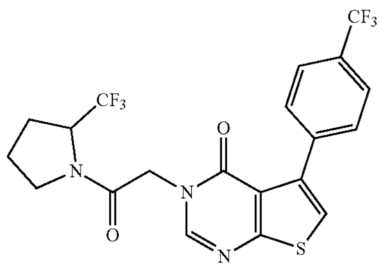 [SMILES: O=C(Cn1cnc2scc(-c3ccc(C(F)(F)F)cc3)c2c1=O)N1CCCC1C(F)(F)F] | $^1$H NMR (400 MHz, DMSO-$d_6$) δ (ppm): 8.40-8.37 (m, 1H), 7.74-7.69 (m, 5H), 5.10-4.71 (m, 3H), 3.68 (brs, 2H), 2.15-1.90 (m, 4H). Calculated (M + H): 476.08, Found (M + H): 476.3, HPLC purity: 99.31% |
| 19 | 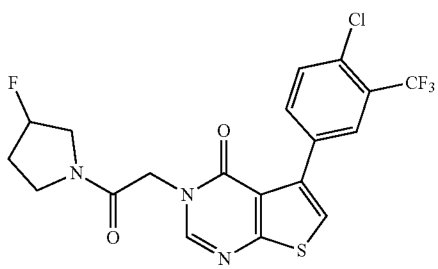 [SMILES: O=C(Cn1cnc2scc(-c3ccc(Cl)c(C(F)(F)F)c3)c2c1=O)N1CCC(F)C1] | $^1$H NMR (400 MHz, DMSO-$d_6$) δ (ppm): 8.36 (s, 1H), 7.94 (s, 1H), 7.79-7.78 (d, J = 7.6 Hz, 2H), 7.72 (d, J = 8.0 Hz, 1H), 5.42-5.30 (m, 1H), 4.94-4.75 (m, 2H), 3.86-3.41 (m, 4H), 2.30-1.98 (m, 2H). Calculated (M + H): 460.04; Found (M + H): 460.0, HPLC purity: 98.31% |

Example 20: 5-(4-chloro-3-(trifluoromethyl)phenyl)-3-(2-oxo-2-(pyrrolidin-1-yl)ethyl)thieno[2,3-d]pyrimidin-4(3H)-one To a stirred solution of 5-(4-chloro-3-(trifluoromethyl)phenyl)thieno[2,3-d]pyrimidin-4(3H)-one (2.0 g, 6.06 mmol) in acetone (50 mL), potassium carbonate (4.18 g, 30.3 mmol) was added followed by 2-chloro-1-(pyrrolidin-1-yl)ethanone (1.07 g, 7.2 mmol) and the resulting mixture was stirred at 55° C. for 2 h. After completion of the reaction, mixture was cooled to room temperature and concentrated under reduced pressure and diluted with water (150 mL) and extracted with ethyl acetate (3×100 mL). The combined organic layer was dried over anhydrous sodium sulphate and concentrated to get crude product and was purified by silica gel column chromatography using 5% methanol in dichloromethane to afford compound 5-(4-chloro-3-(trifluoromethyl)phenyl)-3-(2-oxo-2-(pyrrolidin-1-yl)ethyl)thieno[2,3-d]pyrimidin-4(3H)-one (1.07 g, 40% yield) as off white solid.

$^1$H NMR (400 MHz, DMSO-$d_6$) δ (ppm): 8.34 (s, 1H), 7.94 (s, 1H), 7.79-7.72 (m, 3H), 4.80 (s, 2H), 3.49 (t, J=6.4 Hz, 2H), 3.27 (t, J=6.0 Hz, 2H), 1.94-1.88 (m, 2H), 1.79-1.73 (m, 2H).

Calculated (M+H): 442.05; Found (M+H): 442.3.

HPLC purity: 99.57%.

Example 21: 5-(4-chloro-3-fluorophenyl)-3-(2-oxo-2-(pyrrolidin-1-yl)ethyl)thieno[2,3-d]pyrimidin-4(3H)-one

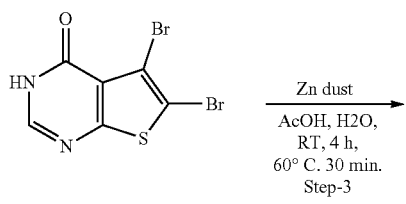

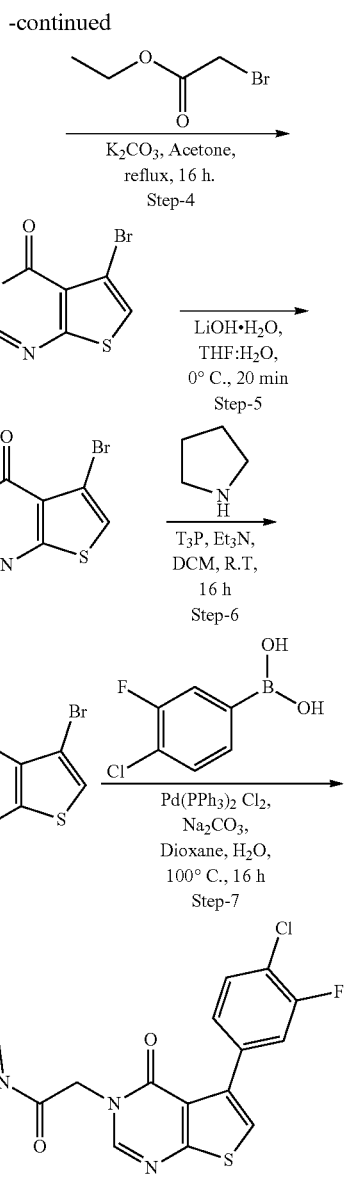

Step 1: Thieno[2,3-d]pyrimidin-4(3H)-one

A suspension of ethyl 2-aminothiophene-3-carboxylate (39.0 g, 248.10 mmol) and formamide (90 mL) was heated at 180° C. for 16 h. The reaction mixture was cooled to room temperature, poured on to ice water (100 mL) and stirred for 30 minutes. The precipitated product was filtered, washed with water, dried to afford the title compound thieno[2,3-d]pyrimidin-4(3H)-one (26.0 g, crude) as a brown solid.

Calculated (M+H): 153.0; Found (M+H): 153.1.

Step 2: 5,6-dibromothieno[2,3-d]pyrimidin-4(3H)-one

To a stirred solution of thieno[2,3-d]pyrimidin-4(3H)-one (2.0 g, 13.15 mmol) and potassium acetate (7.7 g, 78.94 mmol) in acetic acid (20 mL) was added bromine (4.1 mL, 78.94 mmol) at 0° C. The reaction mixture was stirred at 100° C. for 16 h. The reaction mixture was concentrated, the residue was basified with saturated sodium bicarbonate solution and extracted with ethyl acetate (3×100 mL). The combined organic layer was dried over anhydrous sodium sulfate, filtered and evaporated under vacuum to afford title compound 5,6-dibromothieno[2,3-d]pyrimidin-4(3H)-one (2.9 g, crude) as off white solid.

Calculated (M+H): 308.83; Found (M+H): 309.1.

Step 3: 5-bromothieno[2,3-d]pyrimidin-4(3H)-one

To a stirred solution of 5,6-dibromothieno[2,3-d]pyrimidin-4(3H)-one) (2.9 g, 9.41 mmol) in a mixture of acetic acid (144 mL) and water (36 mL) was added zinc dust (1.83 g, 28.24 mmol) at room temperature and stirred for 4 h. A second portion of zinc dust (1.8 g) was added and stirred at 60° C. for 30 minutes. The reaction mixture was diluted with water (100 mL) and extracted with ethyl acetate (3×100 mL). The combined organic layer was dried over anhydrous sodium sulfate, filtered and concentrated under vacuum to afford the title compound 5-bromothieno[2,3-d]pyrimidin-4 (3H)-one (2.1 g, crude) as off white solid.

Calculated (M+H): 230.91; Found (M+H): 231.0.

Step 4: Ethyl 2-(5-bromo-4-oxothieno[2,3-d]pyrimidin-3(4H)-yl)acetate

To a stirred mixture of 5-bromothieno[2,3-d]pyrimidin-4(3H)-one (4.5 g, 19.56 mmol) and potassium carbonate (8.1 g, 58.69 mmol) in acetone (150 mL) was added ethyl-2-bromoacetate (4.33 mL, 39.13 mmol). The reaction mixture was heated at 55° C. for 6 h. The reaction mixture was filtered and the filtrate was evaporated under vacuum to get the crude product, which was purified by silica gel column chromatography using 30% ethyl acetate in hexane to afford the title compound ethyl 2-(5-bromo-4-oxothieno[2,3-d]pyrimidin-3(4H)-yl)acetate (1.6 g, 25.81% yield) as a white solid.

Calculated (M+H): 316.95, Found (M+H): 317.1.

Step 5: 2-(5-bromo-4-oxothieno[2,3-d]pyrimidin-3 (4H)-yl)acetic Acid

To a stirred solution of ethyl 2-(5-bromo-4-oxothieno[2,3-d]pyrimidin-3(4H)-yl)acetate (1.0 g, 3.15 mmol) in tetrahydrofuran:water mixture (50 mL, 4:1) was added lithium hydroxide monohydrate (0.66 g, 15.77 mmol) at 0° C. and stirred for 20 minutes. The reaction mixture was acidified with 1.5 N hydrochloric acid, the pricifitated product was filtered, washed with water, dried to get the title compound 2-(5-bromo-4-oxothieno[2,3-d]pyrimidin-3(4H)-yl)acetic acid (0.79 g, 86.81% yield) as off-white solid.

Calculated (M−H): 286.92; Found (M−H): 287.0.

Step 6: 5-bromo-3-(2-oxo-2-(pyrrolidin-1-yl)ethyl)thieno[2,3-d]pyrimidin-4(3H)-one To a stirred solution of 2-(5-bromo-4-oxothieno[2,3-d]pyrimidin-3(4H)-yl)acetic acid (0.7 g, 2.42 mmol), triethylamine (1.7 mL, 12.11 mmol) and pyrrolidine (0.4 mL, 4.84 mmol) in dichloromethane (20 mL) was added 1-propylphosphonic anhydride (T$_3$P) (1.63 mL, 3.633 mmol, 50% solution in ethyl acetate) at 0° C. and the reaction mixture was stirred at room temperature for 16 h. The reaction mixture was diluted with water (50 mL) and extracted with dichloromethane (3×50 mL). The combined organic layer was dried over anhydrous sodium sulfate, filtered and concentrated under vacuum to afford the crude product, which was purified by silica gel column chromatography using 2% methanol in dichloromethane to afford title compound 5-bromo-3-(2-oxo-2-(pyrrolidin-1-yl)ethyl)thieno[2,3-d]pyrimidin-4(3H)-one (0.4 g, 43.01% yield).

Calculated (M+H): 341.98; Found (M+H): 342.0.

Step 7: 5-(4-chloro-3-fluorophenyl)-3-(2-oxo-2-(pyrrolidin-1-yl)ethyl)thieno[2,3-d]pyrimidin-4(3H)-one To a stirred suspension of 5-bromo-3-(2-oxo-2-(pyrrolidin-1-yl)ethyl)thieno[2,3d]pyrimidin-4(3H)-one (0.11 g, 0.32 mmol), (4-chloro-3-fluorophenyl)boronic acid (0.073 g, 0.41 mmol) and sodium carbonate (0.1 g, 0.96 mmol) in 1,4-dioxane:water mixture (10 mL, 4:1) argon was purged for 10 minutes. Then bis(triphenylphosphine)palladium(II) dichloride (0.02 g, 0.03 mmol) was added and the reaction mixture was heated at 100° C. for 16 h. The reaction mixture was diluted with water (30 mL) and extracted with ethyl acetate (2×50 mL). The combined organic layer was dried over anhydrous sodium sulfate, filtered and evaporated to get the crude product, which was purified by preparative HPLC (method: column: Inertsil ODS 3V (250 mm×4.6 mm×5µ), mobile phase (A): 0.01% ammonia in water, mobile phase (B): methanol, flow rate: 1.0 mL/min, T/% B: 0/20, 8/80, 25/90, 27/20, 30/20) to afford the title compound 5-(4-chloro-3-fluorophenyl)-3-(2-oxo-2-(pyrrolidin-1-yl)ethyl)thieno[2,3-d]pyrimidin-4(3H)-one (0.035 g, 27.77% yield) as a white solid.

$^1$H NMR (400 MHz, DMSO-$d_6$) δ (ppm): 8.35 (s, 1H), 7.7 (s, 1H), 7.61-7.52 (m, 2H), 7.36 (d, J=8.0 Hz, 1H), 4.81 (s, 2H), 3.51 (t, J=6.8 Hz, 2H), 3.28 (t, J=9.2 Hz, 2H), 1.94-1.89 (m, 2H), 1.81-1.76 (m, 2H).

Calculated (M+H): 392.06; Found M+H: (392.2).

HPLC purity: 98.49%.

Examples 22-75: The Following Compounds were Prepared by the Method Described Above

| Ex. No. | Structure | Analytical data |
| --- | --- | --- |
| 22 | 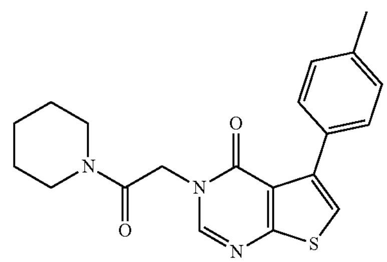 [SMILES: Cc1ccc(-c2csc3ncn(CC(=O)N4CCCCC4)c(=O)c23)cc1] | $^1$H NMR (400 MHz, DMSO-$d_6$) δ (ppm): 8.31 (s, 1H), 7.47 (s, 1H), 7.36 (d, J = 7.6 Hz, 2H), 7.17 (d, J = 7.6 Hz, 2H), 4.88 (s, 2H), 3.3.46 (brs, 2H), 3.39 (brs, 2H), 2.32 (s, 3H), 1.58 (brs, 4H), 1.42 (brs, 2H). Calculated (M + H): 368.14, Found (M + H): 368.4. HPLC purity: 99.82% |
| 23 | 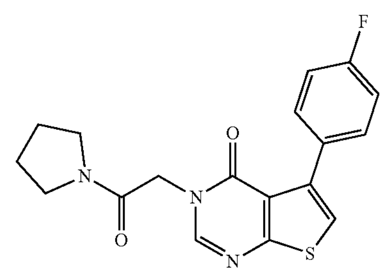 [SMILES: O=C(Cn1cnc2scc(-c3ccc(F)cc3)c2c1=O)N1CCCC1] | $^1$H NMR (400 MHz, DMSO-$d_6$) δ (ppm): 8.33 (s, 1H), 7.55 (s, 1H), 7.53-7.50 (m, 2H), 7.19 (t, J = 8.8 Hz, 2H), 4.79 (s, 2H) 3.50 (t, J = 7.2 Hz, 2H), 3.28-3.30 (m, 2H), 1.96-1.89 (m, 2H), 1.81-1.74 (m, 2H). Calculated (M + H): 358.09, Found (M + H): 358.4. HPLC purity: 99.79% |
| 24 | 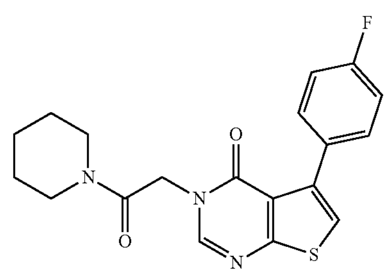 [SMILES: O=C(Cn1cnc2scc(-c3ccc(F)cc3)c2c1=O)N1CCCCC1] | $^1$H NMR (400 MHz, DMSO-$d_6$) δ (ppm): 8.32 (s, 1H), 7.54 (s, 1H), 7.53-7.49 (m, 2H), 7.19 (t, J = 8.8 Hz, 2H), 4.89 (s, 2H), 3.45-3.38 (m, 4H), 1.58 (s, 4H), 1.42 (brs, 2H). Calculated (M + H): 372.11, Found (M + H): 372.1. HPLC purity: 99.26% |
| 25 | 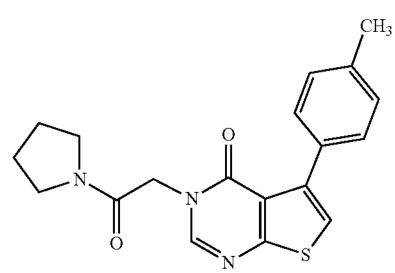 [SMILES: Cc1ccc(-c2csc3ncn(CC(=O)N4CCCC4)c(=O)c23)cc1] | $^1$H NMR (400 MHz, DMSO-$d_6$) δ (ppm): 8.32 (s, 1H), 7.48 (s, 1H), 7.36 (d, J = 7.6 Hz, 2H), 7.16 (d, J = 8.0 Hz, 2H), 4.78 (s, 2H), 3.51 (t, J = 6.8 Hz, 2H), 3.30 (t, J = 8.4 Hz, 2H), 2.32 (s, 3H), 1.96-1.89 (m, 2H), 1.81-1.74 (m, 2H). Calculated (M + H): 354.12, Found (M + H): 354.1. HPLC purity: 99.67% |

-continued

| Ex. No. | Structure | Analytical data |
|---|---|---|
| 26 | 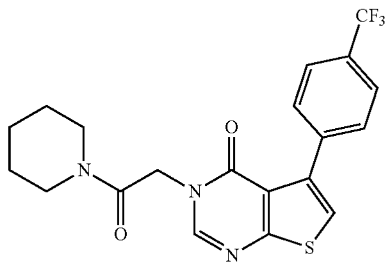 [SMILES: O=C(Cn1cnc2scc(-c3ccc(C(F)(F)F)cc3)c2c1=O)N1CCCCC1] | ¹H NMR (400 MHz, DMSO-d₆) δ (ppm): 8.36 (s, 1H), 7.75-7.68 (m, 5H), 4.9 (s, 2H), 3.45-(brs, 2H), 3.39 (brs, 2H), 1.57 (brs, 4H), 1.43 (brs, 2H). Calculated (M + H): 422.11, Found (M + H): 422.1. HPLC purity: 98.21% |
| 27 | 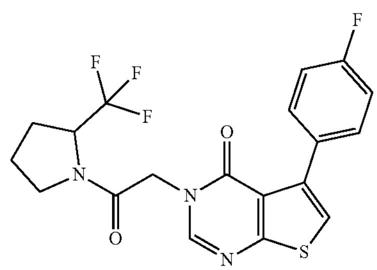 [SMILES: O=C(Cn1cnc2scc(-c3ccc(F)cc3)c2c1=O)N1CCCC1C(F)(F)F] | ¹H NMR (400 MHz, DMSO-d₆) δ (ppm): 8.36 (d, J = 13.2 Hz, 1H), 7.56 (s, 1H), 7.53-7.50 (m, 2H), 7.19 (t, J = 8.8 Hz, 2H), 5.09-4.69 (m, 3H), 3.68-3.62 (m, 2H), 2.18-1.90 (m 4H). Calculated (M + H) 426.08, Found (M + H): 426.3. HPLC purity: 99.30% |
| 28 | 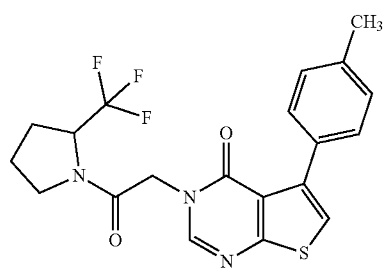 [SMILES: Cc1ccc(-c2csc3ncn(CC(=O)N4CCCC4C(F)(F)F)c(=O)c23)cc1] | ¹H NMR (400 MHz, DMSO-d₆) δ (ppm): 8.32 (s, 1H), 7.48 (s, 1H), 7.36 (d, J = 7.6 Hz, 2H), 7.16 (d, J = 8.0 Hz, 2H), 4.78 (s, 2H), 3.51 (t, J = 6.8 Hz, 2H), 3.30 (t, J = 8.4 Hz, 2H), 2.32 (s, 3H), 1.96-1.89 (m, 2H), 1.81-1.74 (m, 2H). Calculated (M + H): 422.11, Found (M + H): 354.1. HPLC purity: 99.67% |
| 29 | 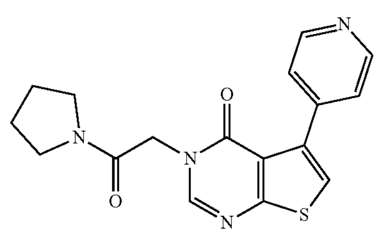 [SMILES: O=C(Cn1cnc2scc(-c3ccncc3)c2c1=O)N1CCCC1] | ¹H NMR (400 MHz, DMSO-d₆) δ (ppm): 8.57 (d, J = 5.6 Hz 2H), 8.36 (s, 1H), 7.79 (s, 1H), 7.5 (d, J = 6.0 Hz, 2H), 4.81 (s, 2H), 3.51 (t, J = 6.8 Hz, 2H), 3.28 (t, J = 11.2 Hz, 2H), 1.96-1.89 (m, 2H), 1.74-1.81 (m, 2H). Calculated (M + H): 341.1, Found (M + H): 341.1 HPLC purity: 98.58%. |
| 30 | 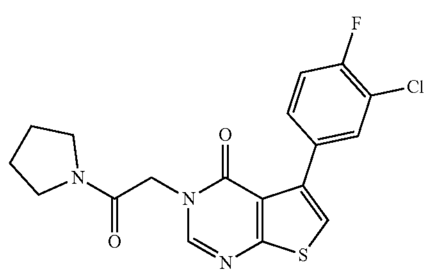 [SMILES: O=C(Cn1cnc2scc(-c3ccc(F)c(Cl)c3)c2c1=O)N1CCCC1] | ¹H NMR (400 MHz, DMSO-d₆) δ (ppm): 8.34 (s, 1H), 7.71-7.68 (m, 1H), 7.66 (s, 1H), 7.50-7.48 (m 1H), 7.42 (t, J = 8.8 Hz, 1H), 4.81 (s, 2H), 3.51 (t, J = 6.4 Hz, 2H), 3.30-3.28 (m, 2H), 2.06-1.89 (m, 2H), 1.81-1.74 (m, 2H). Calculated (M + H): 392.06, Found (M + H): 392.1. HPLC purity: 99.25% |
| 31 | 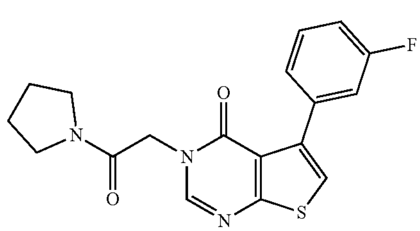 [SMILES: O=C(Cn1cnc2scc(-c3cccc(F)c3)c2c1=O)N1CCCC1] | ¹H NMR (400 MHz, DMSO-d₆) δ (ppm): 8.34 (s, 1H), 7.64 (s, 1H), 7.44-7.38 (m, 1H), 7.34-7.30 (m, 2H), 7.20-7.16 (m, 1H), 4.80 (s, 2H), 3.51 (t, J = 6.8 Hz, 2H), 1.96-1.89 (m, 2H) 1.81-1.74 (m, 2H) (2H are merged with DMSO water peak). Calculated (M + H): 358.09, Found (M + H): 358.1. HPLC purity: 99.61 |

| Ex. No. | Structure | Analytical data |
|---|---|---|
| 32 | 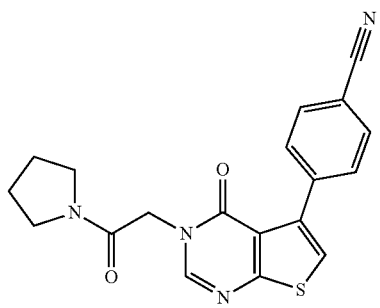 [SMILES: N#Cc1ccc(-c2csc3ncn(CC(=O)N4CCCC4)c(=O)c23)cc1] | $^1$H NMR (400 MHz, DMSO-d$_6$) δ (ppm): 8.36 (s, 1H), 7.84 (t, J = 1.6 Hz, 2H), 7.76 (s, 1H), 7.68 (d, J = 8.4 Hz, 2H), 4.8 (s, 2H), 3.5 (t, J = 7.2 Hz, 2H), 3.28 (t, J = 8.4 Hz, 2 H), 1.95-1.89 (m, 2H), 1.81-1.74 (m, 2H). Calculated (M + H): 365.1, Found (M + H): 365.1. HPLC: 99.77% |
| 33 | 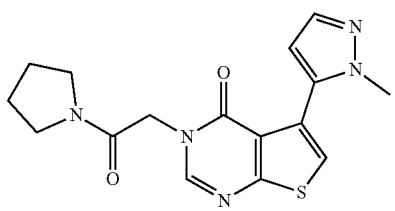 [SMILES: Cn1nccc1-c1csc2ncn(CC(=O)N3CCCC3)c(=O)c12] | $^1$H NMR (400 MHz, DMSO-d$_6$) δ (ppm): 8.35 (s, 1H), 7.67 (s, 1H), 7.40 (s, 1H), 6.28 (s, 1H), 4.79 (s, 2H), 3.59 (s, 3H), 3.5 (t, J = 6.8 Hz, 2H), 3.28 (s, 2H), 2.06-1.89 (m, 2H), 1.81-1.76 (m, 2H). Calculated (M + H): 344.11, Found (M + H): 344.1. HPLC purity: 99.16%. |
| 34 | 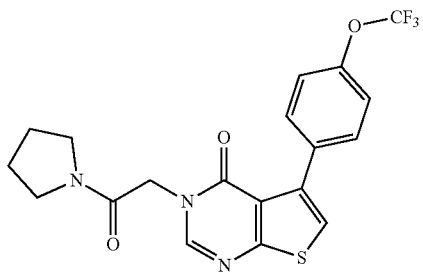 [SMILES: O=C(Cn1cnc2scc(-c3ccc(OC(F)(F)F)cc3)c2c1=O)N1CCCC1] | $^1$H NMR (400 MHz, CDCl$_3$) δ (ppm): 8.05 (s, 1H), 7.55 (d, J = 8.8 Hz, 2H), 7.24 (t, J = 6.8 Hz, 2H), 7.13 (s, 1H), 4.71 (s, 2H), 3.57 (t, J = 7.2 Hz, 2H), 3.49 (t, J = 6.8 Hz, 2H), 2.05-1.99 (m, 2H), 1.91-1.84 (m, 2H). Calculated (M + H): 424.09, Found (M + H): 424.1. HPLC: 99.75% |
| 35 | 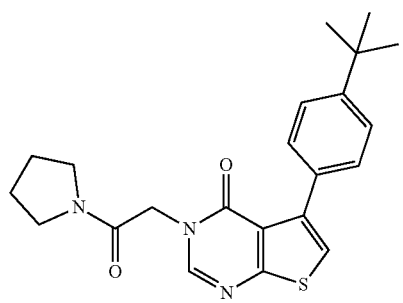 [SMILES: CC(C)(C)c1ccc(-c2csc3ncn(CC(=O)N4CCCC4)c(=O)c23)cc1] | $^1$H NMR (400 MHz, DMSO-d$_6$) δ (ppm): 8.32 (s, 1H), 7.49 (s, 1H), 7.41-7.36 (m, 4H), 4.78 (s, 2H), 3.50 (t, J = 6.4 Hz, 2H) 3.30 (s, 2H) 1.92 (t, J = 8.0 Hz, 2H), 1.77 (t, J = 6.8 Hz, 2H), 1.30 (s, 9H). Calculated (M + H): 396.17, Found (M + H): 396.2. HPLC purity: 99.13% |
| 36 | 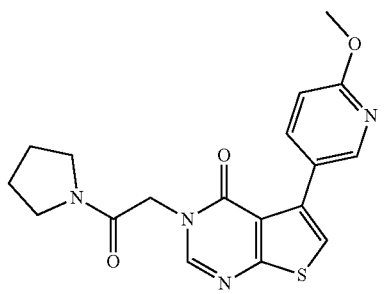 [SMILES: COc1ccc(-c2csc3ncn(CC(=O)N4CCCC4)c(=O)c23)cn1] | $^1$H NMR (400 MHz, DMSO-d$_6$) δ (ppm): 8.34 (s, 1H), 8.26 (d, J = 2.4 Hz, 1H), 7.82-7.79 (dd, J = 2.0 Hz, 8.4 Hz, 1H), 7.59 (s, 1H), 6.82 (d, J = 9.2 Hz, 1H), 4.79 (s, 2H), 3.88 (s, 3H), 3.51 (t, J = 6.4 Hz, 2H), 3.31 (t, J = 10.4 Hz, 2H), 1.96-1.89 (m, 2H), 1.82-1.75 (m, 2H). Calculated M + H: 371.11, Found M + H: 371.1. HPLC: 99.29% |

-continued

| Ex. No. | Structure | Analytical data |
|---|---|---|
| 37 | 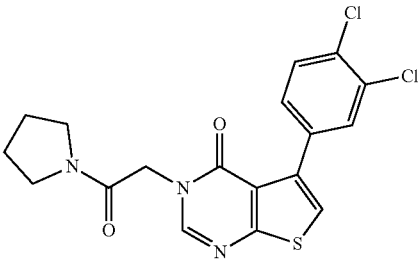 [SMILES: O=C(Cn1cnc2scc(-c3ccc(Cl)c(Cl)c3)c2c1=O)N1CCCC1] | ¹H NMR (400 MHz, DMSO-d$_6$) δ 8.35 (s, 1H), 7.75 (d, J = 1.6 Hz, 1H), 7.71 (s, 1H), 7.64 (d, J = 8.4 Hz, 1H), 7.46-7.49 (m, 1H), 4.81 (s, 2H), 3.51 (t, J = 6.8 Hz, 2H), 3.28 (t, J = 9.6 Hz, 2H), 1.89-2.06 (m, 2H), 1.74-1.81 (m, 2H). Calculated M + H: 408.3, Found M + H: 408.3. HPLC purity: 98.49% |
| 38 | 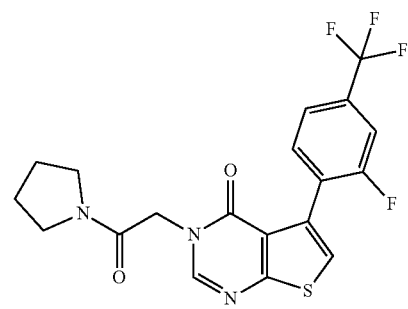 [SMILES: O=C(Cn1cnc2scc(-c3ccc(C(F)(F)F)cc3F)c2c1=O)N1CCCC1] | ¹H NMR (400 MHz, DMSO-d$_6$) δ (ppm): 8.34 (s, 1H), 7.73 (s, 1H), 7.70-7.60 (m, 3H), 4.78 (s, 2H), 3.48 (t, J = 6.8 Hz, 2H), 1.93-1.89 (m, 2H), 1.8-1.75 (m, 2H). 2H merged with DMSO water peak. Calculated (M + H): 426.08, Found (M + H): 426.3. HPLC purity: 99.55% |
| 39 | 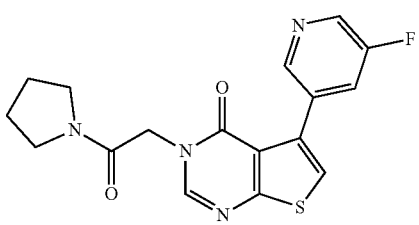 [SMILES: O=C(Cn1cnc2scc(-c3cncc(F)c3)c2c1=O)N1CCCC1] | ¹H NMR (400 MHz, DMSO-d$_6$) δ (ppm): 8.58 (m, 2H), 8.37 (s, 1H), 7.86-7.82 (m, 2H), 4.82 (s, 2H), 3.51 (t, J = 6.8 Hz, 2H) 3.28 (CH$_2$ merged with water peak), 1.95-1.89 (m, 2H), 1.81-1.76 (m, 2H). Calculated (M + H): 358.09, Found (M + H): 359.3. HPLC purity: 98.91% |
| 40 | 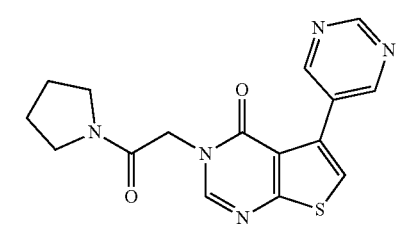 [SMILES: O=C(Cn1cnc2scc(-c3cncnc3)c2c1=O)N1CCCC1] | ¹H NMR (400 MHz, DMSO-d$_6$) δ (ppm): 9.12 (s, 1H), 8.91 (s, 2H), 8.37 (s, 1H), 7.87 (s, 1H), 4.81 (s, 2H), 3.50 (t, J = 7.2 Hz, 2H), 3.29 (t, J = 11.2 Hz, 2H), 1.93-1.88 (m, 2H), 1.80-1.73 (m, 2H). Calculated (M + H): 342.38. Found (M + H): 342.0. HPLC purity: 99.52% |
| 41 | 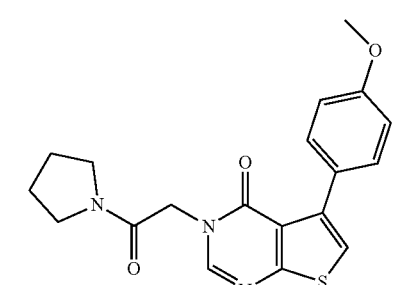 | ¹H NMR (400 MHz, DMSO-d$_6$) δ (ppm): 8.30 (s, 1H), 7.44-7.39 (m, 3H), 6.91 (d, J = 8.0 Hz, 2H), 4.77 (s, 2H), 3.76 (s, 3H), 3.49 (t, J = 6.8 Hz, 2H), 3.27 (brs, 2 H), 1.92-1.89 (m, 2H), 1.78-1.75 (m, 2H). Calculated (M + H): 370.11, Found (M + H): 370.1. HPLC purity: 99.96% |
| 42 | 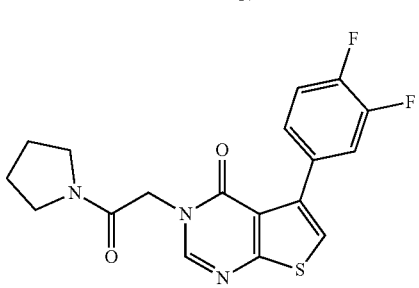 | ¹H NMR (400 MHz, DMSO-d$_6$) δ (ppm): 8.33 (s, 1H), 7.63 (s, 1H), 7.57-7.52 (m, 1H), 7.46-7.39 (m, 1H), 7.33 (brs, 1H), 4.79 (s, 2H), 3.49 (t, J = 6.4 Hz, 2H), 3.28 (t, J = 10 Hz, 2H), 1.95-1.88 (m, 2H), 1.8-1.73 (m, 2H). Calculated (M + H): 376.09, Found (M + H): 376.1. HPLC: 99.32% |

| Ex. No. | Structure | Analytical data |
|---|---|---|
| 43 | 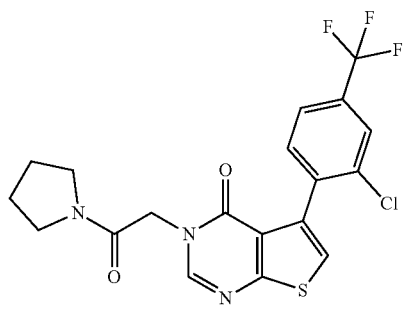 [SMILES: O=C(Cn1cnc2scc(-c3ccc(C(F)(F)F)cc3Cl)c2c1=O)N1CCCC1] | ¹H NMR (400 MHz, DMSO-d₆) δ (ppm): 8.32 (s, 1H), 7.88 (s, 1H), 7.71 (d, J = 8.0 Hz, 1H), 7.64 (s, 1H), 7.59 (d, J = 7.6 Hz, 1H), 4.74 (s, 2H), 3.45 (t, J = 7.2 Hz, 2H), 3.26 (t, J = 7.6 Hz, 2H), 1.92-1.85 (m, 2H), 1.78-1.71 (m, 2H). Calculated (M + H): 442.02, Found (M + H): 442.1. HPLC: 99.78% |
| 44 | 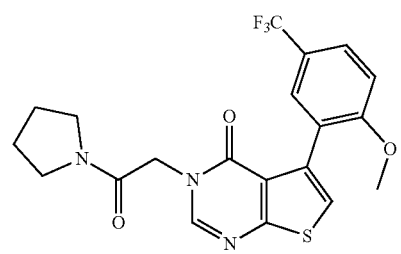 [SMILES: COc1ccc(C(F)(F)F)cc1-c1csc2ncn(CC(=O)N3CCCC3)c(=O)c12] | ¹H NMR (400 MHz, DMSO-d₆) δ (ppm): 8.28 (s, 1H), 7.69 (d, J = 8.8 Hz, 1H), 7.52 (s, 1H), 7.48 (brs, 1H), 7.19 (d, J = 8.8 Hz, 1H), 4.72 (s, 2H), 3.69 (brs, 3H), 3.46 (t, J = 7.2 Hz, 2H), 3.24 (brs, 2H), 1.92-1.86 (m, 2H), 1.76-1.71 (m, 2H). Calculated (M + H): 438.1, Found (M + H): 438.0. HPLC purity: 98.63% |
| 45 | 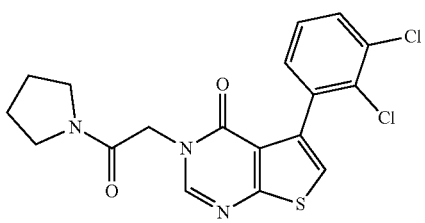 [SMILES: O=C(Cn1cnc2scc(-c3cccc(Cl)c3Cl)c2c1=O)N1CCCC1] | ¹H NMR (400 MHz, DMSO-d₆) δ (ppm): 8.30 (s, 1H), 7.64-7.62 (m, 1H), 7.56 (s, 1H), 7.37-7.31 (m, 2H), 4.74 (s, 2H), 3.45 (t, J = 6.4 Hz, 2H), 3.26 (brs, 2H), 1.92-1.85 (m, 2H), 1.78-1.73 (m, 2H). Calculated (M + H): 408.03, Found (M + H): 408.3. HPLC purity: 99.36% |
| 46 | 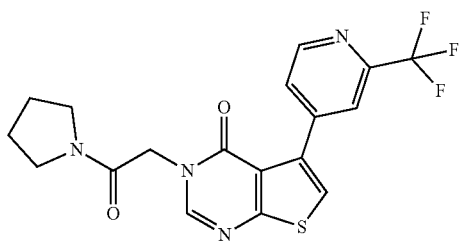 [SMILES: O=C(Cn1cnc2scc(-c3ccnc(C(F)(F)F)c3)c2c1=O)N1CCCC1] | ¹H NMR (400 MHz, DMSO-d₆) δ (ppm): 8.84 (s, 1H), 8.37 (s, 1H), 8.16 (d, J = 8.0 Hz, 1H), 7.92 (d, J = 8.4 Hz, 1H), 7.86 (s, 1H), 4.80 (s, 2H), 3.49 (t, J = 6.8 Hz, 2H), 3.27 (t, J = 8.0 Hz, 2H), 1.88-1.94 (m, 2H), 1.73-1.79 (m, 2H) Calculated (M + H) 409.09, Found (M + H): 409.1. HPLC purity: 99.92% |
| 47 | 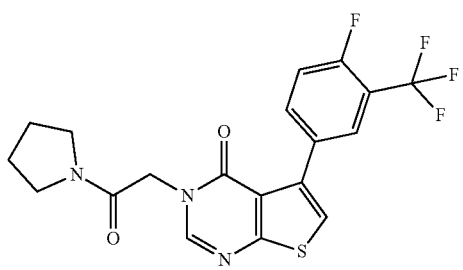 [SMILES: O=C(Cn1cnc2scc(-c3ccc(F)c(C(F)(F)F)c3)c2c1=O)N1CCCC1] | ¹H NMR (400 MHz, DMSO-d₆) δ (ppm): 8.33 (s, 1H), 7.86-7.81 (m, 2H), 7.71 (s, 1H), 7.51 (t, J = 8.8 Hz, 1H), 4.80 (s, 2H), 3.49 (t, J = 7.2 Hz, 2H), 3.27 (t, J = 7.2 Hz, 2H), 1.94-1.87 (m, 2H), 1.83-1.72 (m, 2H). Calculated (M + H): 426.08, Found (M + H): 426.0. HPLC purity: 99.80%. |

| Ex. No. | Structure | Analytical data |
|---|---|---|
| 48 | 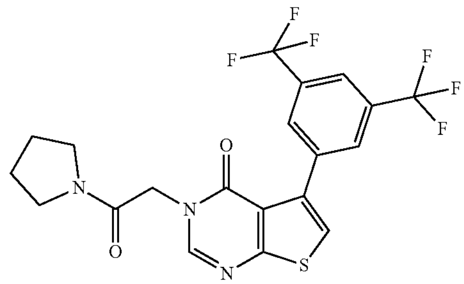 [SMILES: O=C(Cn1cnc2scc(-c3cc(C(F)(F)F)cc(C(F)(F)F)c3)c2c1=O)N1CCCC1] | ¹H NMR (400 MHz, DMSO-d₆) δ (ppm): 8.35 (s, 1H), 8.16 (s, 1H), 8.06 (s, 1H), 7.89 (s, 2H), 4.81 (s, 2H), 3.5 (t, J = 6.8 Hz, 2H), 3.27 (t, J = 8.0 Hz, 2H), 1.94-1.87 (m, 2H), 1.79-1.72 (m, 2H). Calculated (M + H): 476.08, Found (M + H): 476.0. HPLC: 99.52% |
| 49 | 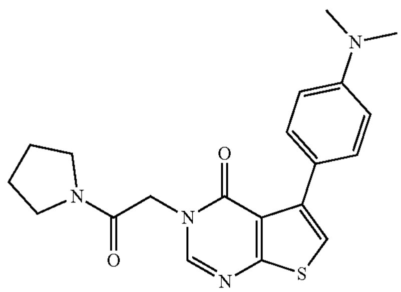 [SMILES: CN(C)c1ccc(-c2csc3ncn(CC(=O)N4CCCC4)c(=O)c23)cc1] | ¹H NMR (400 MHz, DMSO-d₆) δ (ppm): 8.28 (s, 1H), 7.32 (d, J = 10 Hz, 2H), 6.68 (d, J = 8.4 Hz, 2H), 4.77 (s, 2H), 3.49 (t, J = 6.4 Hz, 2H), 3.29 (t, J = 9.6 Hz, 2H), 2.9 (s, 6H), 1.93-1.89 (m, 2H), 1.78-1.75 (m, 2H) Calculated (M + H): 383.15, Found (M + H): 383.1. HPLC: 97.69% |
| 50 | 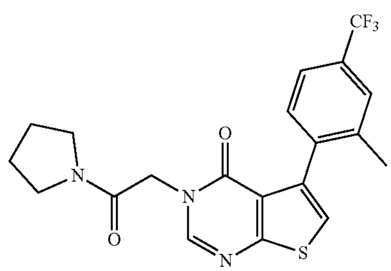 [SMILES: Cc1cc(C(F)(F)F)ccc1-c1csc2ncn(CC(=O)N3CCCC3)c(=O)c12] | ¹H NMR (400 MHz, DMSO-d₆) δ (ppm): 8.32 (s, 1H), 7.58 (s, 1H), 7.52-7.49 (m, 2H), 7.35 (d, J = 8.0 Hz, 1H), 4.73 (s, 2H), 3.44 (t, J = 6.8 Hz, 2H), 3.26 (t, J = 10.8 Hz, 2H), 2.11 (s, 3H), 1.92-1.86 (m, 2H), 1.78-1.71 (m, 2H) Calculated (M + H): 422.11, Found (M + H): 422.0. HPLC purity: 99.6% |
| 51 | 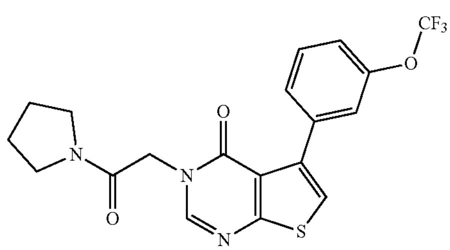 [SMILES: O=C(Cn1cnc2scc(-c3cccc(OC(F)(F)F)c3)c2c1=O)N1CCCC1] | ¹H NMR (400 MHz, DMSO-d₆) δ (ppm): 8.33 (s, 1H), 7.67 (s, 1H), 7.51-7.46 (m, 3H), 7.33 (d, J = 6.4 Hz, 1H), 4.79 (s, 2H), 3.49 (t, J = 6.8 Hz, 2H), 3.29 (t, J = 9.6 Hz, 2H), 1.93-1.88 (m, 2H), 1.79-1.73 (m, 2H). Calculated (M + H): 424.09, Found (M + H): 424.3. HPLC purity: 98.94% |
| 52 | 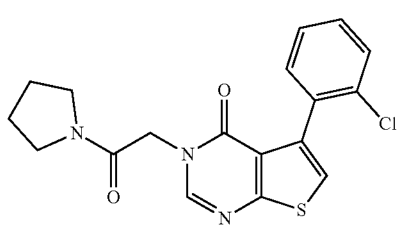 [SMILES: O=C(Cn1cnc2scc(-c3ccccc3Cl)c2c1=O)N1CCCC1] | ¹H-NMR (400 MHz, DMSO-d₆) δ (ppm): 8.29 (s, 1H), 7.50 (s, 1H), 7.45 (d, J = 7.6 Hz, 1H), 7.39-7.30 (m, 3H), 4.73 (s, 2H), 3.45 (t, J = 6.4 Hz, 2H), 3.27-3.24 (m, 2H), 1.92-1.85 (m, 2H), 1.78-1.71 (m, 2H). Calculated (M + H): 374.07, Found (M + H): 374.1. HPLC purity: 97.61% |

-continued

| Ex. No. | Structure | Analytical data |
|---|---|---|
| 53 | 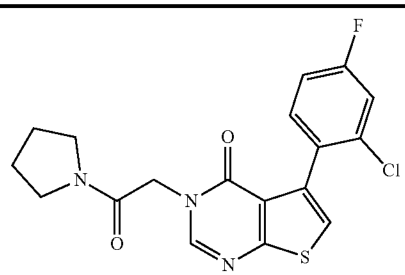 | ¹H NMR (400 MHz, DMSO-d₆) δ (ppm): 8.29 (s, 1H), 7.73 (s, 1H), 7.45 (dd, J₁ = 2.0 Hz, J₂ = 8.8 Hz, 2H), 7.41-7.38 (m, 1H), 7.24-7.19 (m, 1H), 4.74 (s, 2H), 3.46 (t, J = 1.2 Hz, 2H), 3.27 (t, J = 10.4 Hz, 2H), 2.04-1.86 (m, 2H), 1.79-1.72 (m, 2H). Calculated (M + H): 392.06, Found (M + H): 392.1. HPLC purity: 99.79% |
| 54 | 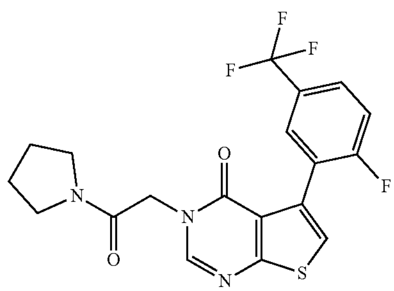 [SMILES: O=C(Cn1cnc2scc(-c3cc(C(F)(F)F)ccc3F)c2c1=O)N1CCCC1] | ¹H NMR (400 MHz, DMSO-d₆) δ (ppm): 8.32 (s, 1H), 7.81-7.75 (m, 3H), 7.46 (t, J = 8.8 Hz, 1H), 4.77 (s, 2H), 3.47 (t, J = 6.8 Hz, 2H), 3.27 (t, J = 8.8 Hz, 2H), 2.04-1.86 (m, 2H), 1.78-1.72 (m, 2H). Calculated (M + H): 426.08, Found (M + H): 426.1. HPLC: 99.89% |
| 55 | 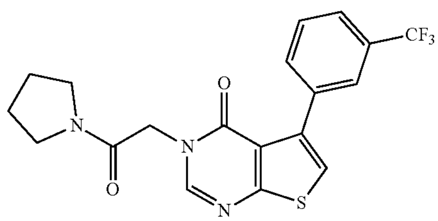 [SMILES: O=C(Cn1cnc2scc(-c3cccc(C(F)(F)F)c3)c2c1=O)N1CCCC1] | ¹H NMR (400 MHz, DMSO-d₆) δ (ppm): 8.34 (s, 1H), 7.81 (s, 1H), 7.77 (d, J = 1.2 Hz, 1H), 7.69 (d, J = 7.6 Hz, 2H), 7.60 (t, J = 8.0 Hz, 1H), 4.80 (s, 2H), 3.49 (LJ = 6.8 Hz, 2H), 1.93-1.88 (m, 2H), 1.79-1.72 (m, 2H). 2H merged with DMSO water peak. Calculated (M + H): 408.09, Found (M + H): 408.1. HPLC purity: 98.93% |
| 56 | 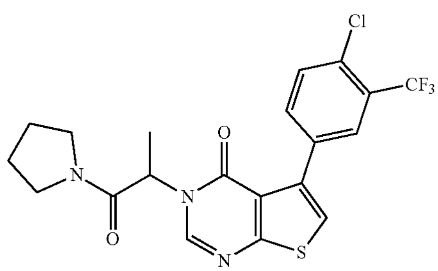 [SMILES: CC(C(=O)N1CCCC1)n1cnc2scc(-c3ccc(Cl)c(C(F)(F)F)c3)c2c1=O] | ¹H NMR (400 MHz, DMSO-d₆) δ (ppm): 8.47 (s, 1H), 7.92 (s, 1H), 7.79-7.72 (m, 3H), 5.62 (q, 1H), 3.59-3.48 (m, 2H), 3.32-3.2 (m, 2H), 1.90-1.84 (m, 2H), 1.79-1.63 (m, 2H), 1.59 (d, J = 7.2 Hz, 3H). Calculated (M + H): 456.07, Found (M + H): 456.0. HPLC purity: 99.9% |
| 57 | 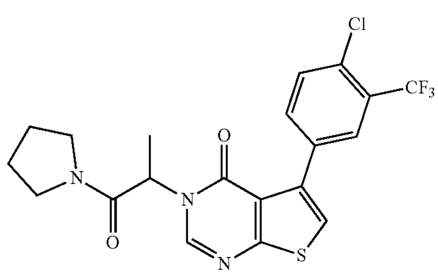 | ¹H-NMR (400 MHz, DMSO-d₆) δ (ppm): 8.45 (s, 1H), 7.68 (dd, J = 2 Hz, 7.2 Hz, 1H), 7.62 (s, 1H), 7.49-7.45 (m, 1H), 7.43-7.39 (m, 1H), 5.65-5.60 (m, 1H), 3.59-3.49 (m, 2H); 3.27-3.24 (m, 2H), 1.91-1.84 (m, 2H), 1.79-1.76 (m, 2H), 1.59 (d, J = 7.6 Hz, 3H). Calculated (M + H): 406.07, Found (M + H): 406.0. HPLC purity: 99.92% |
| 58 | 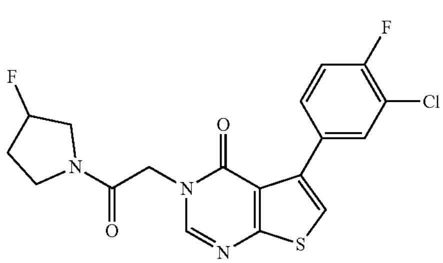 [SMILES: O=C(Cn1cnc2scc(-c3ccc(F)c(Cl)c3)c2c1=O)N1CCC(F)C1] | ¹H-NMR (400 MHz, DMSO-d₆) δ (ppm): 8.34 (d, J = 2.4 Hz, 1H), 7.69 (dd, J = 2.4 Hz, 7.2 Hz, 1H), 7.66 (s, 1H), 7.50-7.47 (m, 1H), 7.43-7.38 (m, 1H), 5.49-5.24 (m, 1H), 4.94-4.76 (m, 2H); 3.89-3.27 (m, 4H), 2.30-1.9 (m, 2H). Calculated (M + H): 410.05, Found (M + H): 410.0. HPLC purity: 98.97% |

-continued

| Ex. No. | Structure | Analytical data |
|---|---|---|
| 59 | 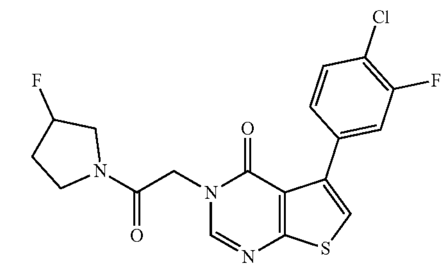 [SMILES: O=C(Cn1cnc2scc(-c3ccc(Cl)c(F)c3)c2c1=O)N1CCC(F)C1] | ¹H NMR (400 MHz, DMSO-d₆) δ (ppm): 8.36 (s, 1H), 7.69 (s, 1H), 7.59-7.51 (m, 2H), 7.35 (d, J = 8.4 Hz, 1H), 5.49-5.24 (m, 1H), 4.93-4.75 (m, 2H), 3.89-3.27 (m, 4H), 2.30-1.93 (m, 2H). Calculated (M + H): 410.05, Found M + H: 410. HPLC purity: 99.99% |
| 60 | 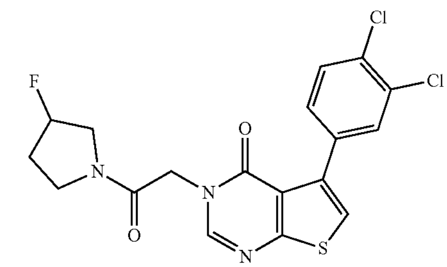 [SMILES: O=C(Cn1cnc2scc(-c3ccc(Cl)c(Cl)c3)c2c1=O)N1CCC(F)C1] | ¹H NMR (400 MHz, DMSO-d₆) δ (ppm): 8.35 (d, J = 2.0 Hz, 1H), 7.74 (d, J = 1.2, 1H), 7.70 (s, 1H), 7.62 (d, J = 8.4 Hz, 1H), 7.46 (d, J = 8.4 Hz, 1H), 5.49-5.24 (m, 1H), 4.93-4.76 (m, 2H), 3.89-3.27 (m, 4H), 2.30-1.93 (m, 2H). Calculated (M + H): 426.02, Found (M + H): 428.0. HPLC purity: 99.99% |
| 61 | 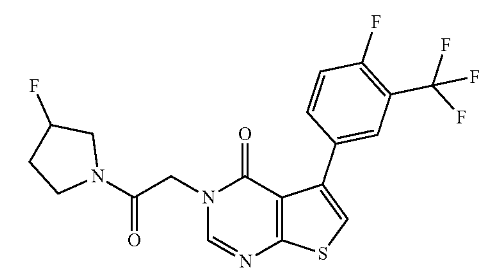 [SMILES: O=C(Cn1cnc2scc(-c3ccc(F)c(C(F)(F)F)c3)c2c1=O)N1CCC(F)C1] | ¹H NMR (400 MHz, DMSO-d₆) δ (ppm): 8.35 (d, J = 2.4 Hz, 1H), 7.87-7.82 (m, 2H), 7.73 (s, 1H), 7.54-7.49 (m, 1H), 5.49-5.24 (m, 1H), 4.94-4.76 (m, 2 H), 3.89-3.27 (m, 4H), 2.30-1.9 (m, 2H). Calculated (M + H): 444.07, Found (M + H): 444.0. HPLC purity: 99.93% |
| 62 | 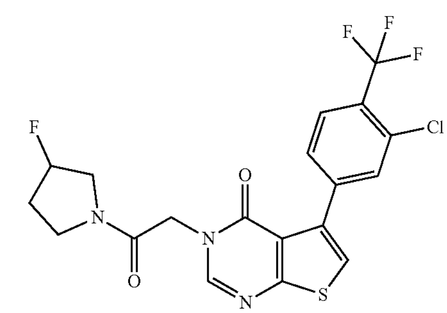 [SMILES: O=C(Cn1cnc2scc(-c3ccc(C(F)(F)F)c(Cl)c3)c2c1=O)N1CCC(F)C1] | ¹H NMR (400 MHz, DMSO-d₆) δ (ppm): 8.37 (d, J = 2.0 Hz, 1H), 7.93-7.81 (m, 3H), 7.64 (d, J = 8.0 Hz, 1H), 5.49-5.24 (m, 1H), 4.94-4.76 (m, 2H), 3.79-3.27 (m, 4H), 2.30-1.90 (m, 2H). Calculated (M + H): 460.84, Found (M + H): 460.0. HPLC purity: 98.05% |
| 63 | 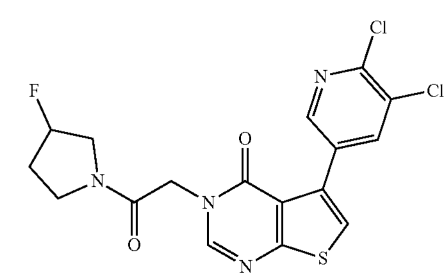 [SMILES: O=C(Cn1cnc2scc(-c3cnc(Cl)c(Cl)c3)c2c1=O)N1CCC(F)C1] | ¹HNMR (400 MHz, DMSO-d₆) δ (ppm): 8.49 (s, 1H), 8.38 (s, 1H), 8.26 (s, 1H), 7.86 (s, 1H), 5.49-5.24 (m, 1H), 4.95-4.77 (m, 2H), 3.90-3.27 (m, 4H), 2.3-1.93 (m, 2H). Calculated (M + H): 427.01, Found (M + H): 427.0. HPLC purity: 98.77% |

-continued

| Ex. No. | Structure | Analytical data |
|---|---|---|
| 64 | 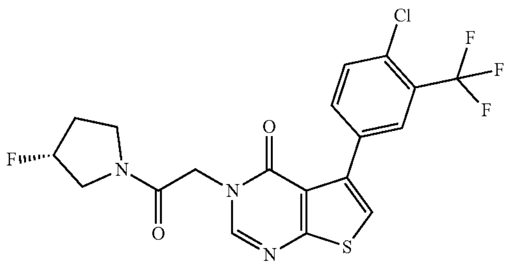 [SMILES: O=C(Cn1cnc2scc(-c3ccc(Cl)c(C(F)(F)F)c3)c2c1=O)N1CC[C@@H](F)C1] | ¹H-NMR (400 MHz, DMSO-d₆) δ (ppm): 8.36 (d, J = 2.0 Hz, 1H), 7.94 (s, 1H), 7.79-7.77 (m, 2H), 7.72 (d, J = 8.4 Hz, 1H), 5.49-5.24 (m, 1H), 4.94-4.76 (m, 2H), 3.86-3.27 (m, 4H), 2.30-2.04 (m, 2H). Calculated (M + H): 460.04, Found (M + H): 460.0. HPLC purity: 99.92% |
| 65 | 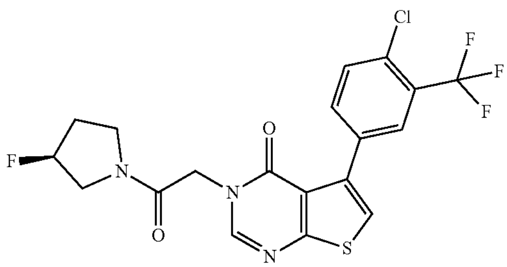 [SMILES: O=C(Cn1cnc2scc(-c3ccc(Cl)c(C(F)(F)F)c3)c2c1=O)N1CC[C@H](F)C1] | ¹H-NMR (400 MHz, DMSO-d₆) δ (ppm): 8.35 (d, J = 2.4 Hz, 1H), 7.94 (s, 1H), 7.79-7.72 (m, 3H), 5.49-5.24 (m, 1H), 4.89-4.79 (m, 2H), 3.86-3.27 (m, 4H), 2.30-2.07 (m, 2H). Calculated (M + H): 460.04, Found (M + H): 460.0. HPLC purity: 99.60% |
| 66 | 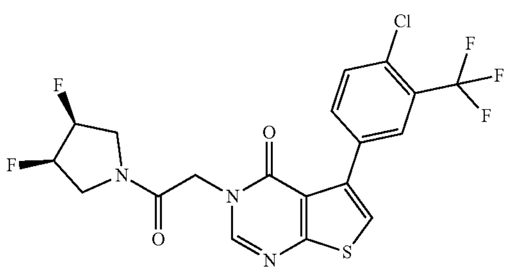 [SMILES: O=C(Cn1cnc2scc(-c3ccc(Cl)c(C(F)(F)F)c3)c2c1=O)N1C[C@@H](F)[C@@H](F)C1] | ¹H-NMR (400 MHz, DMSO-d₆) δ (ppm): 8.35 (s, 1H), 7.94 (d, J = 1.6 Hz, 1H), 7.79-7.72 (m, 3H), 5.38-5.35 (m, 2H), 4.86 (s, 2H), 4.04-3.98 (m, 1H), 3.81-3.27 (m, 3H). Calculated (M + H): 478.04, Found (M + H): 478.0. HPLC purity: 99.76% |
| 67 | 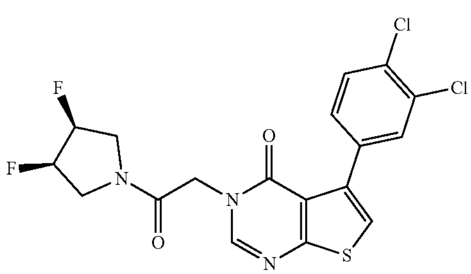 [SMILES: O=C(Cn1cnc2scc(-c3ccc(Cl)c(Cl)c3)c2c1=O)N1C[C@@H](F)[C@@H](F)C1] | ¹H-NMR (400 MHz, DMSO-d₆) δ (ppm): 8.34 (s, 1H), 7.74 (s, 1H), 7.71 (s, 1H), 7.62 (d, J = 8.4 Hz, 1H), 7.46 (d, J = 7.6 Hz, 1H), 5.47-5.23 (m, 2H), 4.85 (s, 2H), 4.06-3.99 (m, 1H), 3.81-3.28 (m, 2H). Calculated (M + H): 444.01, Found (M + H): 444.4. HPLC purity: 99.08% |
| 68 | 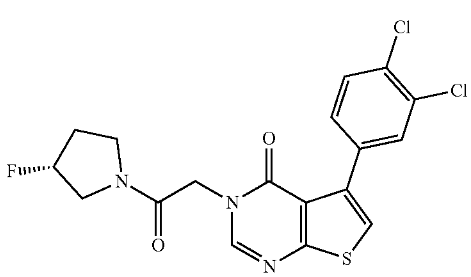 [SMILES: O=C(Cn1cnc2scc(-c3ccc(Cl)c(Cl)c3)c2c1=O)N1CC[C@@H](F)C1] | ¹H-NMR (400 MHz, DMSO-d₆) δ (ppm): 8.30 (s, 1H), 7.74 (s, 1H), 7.70 (s, 1H), 7.62 (d, J = 8.4 Hz, 1H), 7.46 (d, J = 7.2 Hz, 1H), 5.49-5.24 (m, 1H), 4.94-4.76 (m, 2H), 3.86-3.27 (m, 4H), 2.3-1.96 (m, 2H). Calculated (M + H): 426.02, Found (M + H): 426.0. HPLC purity: 98.57% |

-continued

| Ex. No. | Structure | Analytical data |
|---|---|---|
| 69 | 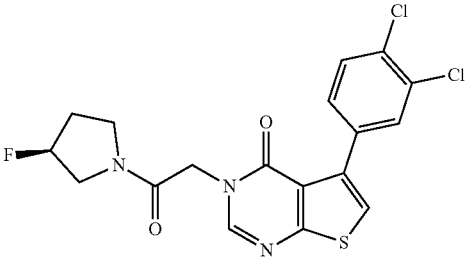 [SMILES: O=C(Cn1cnc2scc(-c3ccc(Cl)c(Cl)c3)c2c1=O)N1CC[C@H](F)C1] | ¹H-NMR (400 MHz, DMSO-d₆) δ (ppm): 8.35 (s, 1H), 7.72 (d, J = 14.8 Hz, 2H), 7.62 (d, J = 8.0 Hz, 1H), 7.46 (d, J = 7.6 Hz, 1H), 5.49-5.24 (m, 1H), 4.89-4.80 (m, 2H), 3.8-3.27 (m, 4H), 2.3-1.9 (m, 2H). Calculated (M + H): 426.02, Found (M + H): 426.0. HPLC purity: 99.30% |
| 70 | 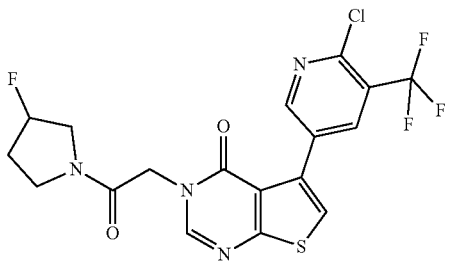 [SMILES: O=C(Cn1cnc2scc(-c3cnc(Cl)c(C(F)(F)F)c3)c2c1=O)N1CCC(F)C1] | ¹H NMR (400 MHz, DMSO-d₆) δ (ppm): 8.79 (d, J = 1.6 Hz, 1H), 8.44 (d, J = 1.6 Hz, 1H), 8.38 (d, J = 2.8, 1H), 7.94 (s, 1H), 5.49-5.24 (m, 1H), 4.96-4.78 (m, 2H), 3.87-3.24 (m, 4H), 2.30-2.07 (m, 2H). Calculated (M + H): 461.8, Found (M + H): 461.0. HPLC purity: 96.21% |
| 71 | 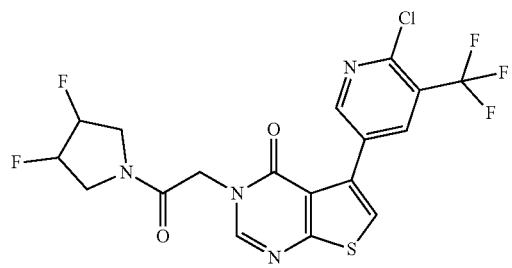 [SMILES: O=C(Cn1cnc2scc(-c3cnc(Cl)c(C(F)(F)F)c3)c2c1=O)N1CC(F)C(F)C1] | ¹H NMR (400 MHz, DMSO-d₆) δ (ppm): 8.80 (d, J = 1.6 Hz, 1H), 8.45 (d, J = 1.6 Hz, 1H), 8.38 (s, 1H), 7.95 (s, 1H), 5.38-5.23 (m, 2H), 4.88 (s, 2H), 4.05-3.99 (m, 1H), 3.77-3.62 (m, 2H), 3.52-3.47 (m, 1H). Calculated (M + H): 479.03, Found (M + H): 479.2, HPLC purity : 99.67% |
| 72 | 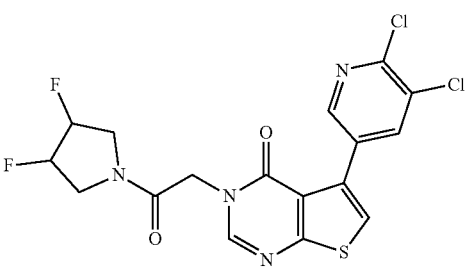 [SMILES: O=C(Cn1cnc2scc(-c3cnc(F)c(Cl)c3)c2c1=O)N1CC(F)C(F)C1] | ¹H NMR (400 MHz, DMSO-d₆) δ (ppm): 8.50 (d, J = 1.6 Hz, 1H), 8.37 (s, 1H), 8.26 (d, J = 1.6 Hz, 1H), 7.87 (s, 1H), 5.47-5.25 (m, 2H), 4.87 (s, 2H), 4.08-3.99 (m, 1H), 3.82-3.63 (m, 2H), 3.52-3.37 (m, 1H). Calculated (M + H): 445.00, Found (M + H): 445.0, HPLC purity: 98.22% |
| 73 | 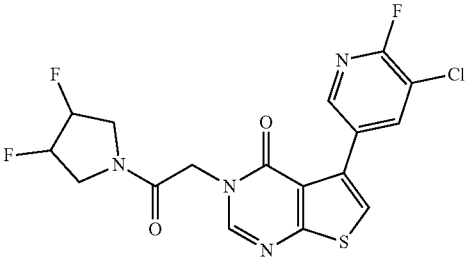 | ¹H NMR (400 MHz, DMSO-d₆) δ (ppm): 8.36 (s, 1H), 8.32-8.30 (m, 2H), 7.83 (s, 1H), 5.47-5.24 (m, 2H), 4.87 (s, 2H), 4.08-3.99 (m, 1H), 3.81-3.63 (m, 2H), 3.53-3.44 (m, 1H). Calculated (M + H): 429.03, Found (M + H): 429.0, HPLC purity: 99.19% |

Example 74: 6-(4-chlorophenyl)-3-(2-oxo-2-(pyrrolidin-1-yl)ethyl)thieno[2,3-d]pyrimidin-4(3H)-one

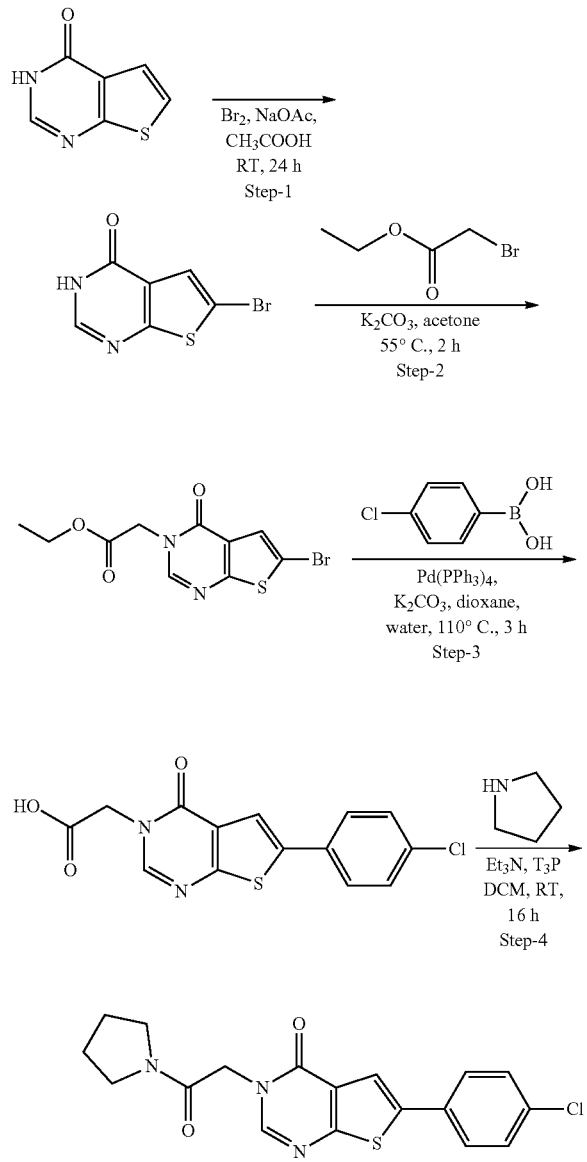

Step 1: 6-bromothieno[2,3-d]pyrimidin-4(3H)-one

To a stirred solution of thieno[2,3-d]pyrimidin-4(3H)-one (4.0 g, 12.33 mmol) and potassium acetate (17.25 g, 210.32 mmol) in acetic acid (100 mL) was added slowly bromine (2.7 mL, 52.57 mmol) at 0° C. The reaction mixture was stirred at room temperature for 24 h. After completion of the reaction, the reaction mixture was concentrated, the residue was basified with saturated sodium bicarbonate solution and extracted with ethyl acetate (2×1000 mL). The combined organic layer was dried over anhydrous sodium sulfate, filtered and concentrated to afford the title compound 6-bromothieno[2,3-d]pyrimidin-4(3H)-one (3.4 g crude, 56% yield) as brown solid.

Calculated (M+H): 230.91; Found (M+H): 231.0.

Step 2: Ethyl 2-(6-bromo-4-oxothieno[2,3-d]pyrimidin-3(4H)-yl)acetate

To a stirred suspension of 6-bromothieno[2,3-d]pyrimidin-4(3H)-one (2.0 g, 8.66 mmol) and potassium carbonate (3.6 g, 25.98 mmol) in acetone, was added ethyl 2-bromoacetate (1.92 mL, 17.31 mmol) at room temperature and resulting mixture was heated at 55° C. for 1 h. The reaction mixture was cooled to room temperature, filtered and the filtrate was evaporated to afford the crude product. The crude product was purified by silica gel column chromatography using 50% ethyl acetate in hexane to afford the title compound ethyl 2-(6-bromo-4-oxothieno[2,3-d]pyrimidin-3 (4H)-yl)acetate (1.91 g, 69.7% yield) as off-white solid.

Calculated (M+H): 316.95; Found (M+H): 317.2.

Step 3: 2-(6-(4-chlorophenyl)-4-oxothieno[2,3-d]pyrimidin-3(4H)-yl)acetic Acid To a stirred suspension of ethyl 2-(6-bromo-4-oxothieno [2,3-d]pyrimidin-3(4H)-yl)acetate (0.1 g, 0.31 mmol) and (4-chlorophenyl)boronic acid (0.12 g, 0.79 mmol) in 1,4-dioxane: water mixture (10 mL, 1:1) was added potassium carbonate (0.13 g, 0.94 mmol). The resulting mixture was purged with argon for 10 minutes. Then tetrakis(triphenylphosphine) palladium(0) (0.02 g, 0.01 mmol) was added and the reaction mixture was heated at 110° C. for 3 h. After completion of the reaction, the reaction mixture was cooled to room temperature and filtered through the celite bed. The filtrate was diluted water (20 mL) and acidified with 1.5 N hydrochloric acid solution at 0° C. The precipitated solid was filtered and dried under suction to afford the title compound 2-(6-(4-chlorophenyl)-4-oxothieno[2,3-d]pyrimidin-3(4H)-yl)acetic acid (0.09 g, 90% yield) as white solid.

Calculated (M+H): 321.0; Found (M+H): 321.0.

Step 4: 6-(4-chlorophenyl)-3-(2-oxo-2-(pyrrolidin-1-yl)ethyl)thieno[2,3-d]pyrimidin-4(3H)-one To a stirred solution of 2-(6-(4-chlorophenyl)-4-oxothieno[2,3-d]pyrimidin-3(4H)-yl)acetic acid (0.09 g, 0.28 mmol) in dichloromethane (20 mL) was added triethylamine (0.23 mL, 1.68 mmol) followed by pyrrolidine (0.03 mL, 0.33 mmol). The reaction mixture was cooled to 0° C., 1-propylphosphonic anhydride ($T_3P$) (0.62 mL, 0.56 mmol, 50% solution in ethyl acetate) was added and stirred at room temperature for 16 h. After completion of the reaction, the reaction mixture was diluted with di chloromethane (50 mL), washed with water (30 mL), brine (30 mL), dried over anhydrous sodium sulfate, filtered and concentrated under vacuum to afford crude product, which was purified by silica gel column chromatography using 5% methanol in dichloromethane to afford title compound 6-(4-chlorophenyl)-3-(2-oxo-2-(pyrrolidin-1-yl)ethyl)thieno[2,3-d]pyrimidin-4 (3H)-one (0.04 g, 38.5% yield)

$^1$H NMR (400 MHz, DMSO-$d_6$) δ (ppm): 8.31 (s, 1H), 7.85 (s, 1H), 7.81 (d, J=8.4 Hz, 2H), 7.50 (d, J=8.4 Hz, 2H), 4.80 (s, 2H), 3.55 (t, J=6.4 Hz, 2H), 3.32 (t, J=6.4 Hz, 2H), 1.98-1.92 (m, 2H), 1.84-1.77 (m, 2H).

Calculated (M+H): 374.07, Found (M+H): 374.1.

HPLC purity: 99.14%.

Examples 75-78: the Following Compounds were Prepared by the Method Described Above

| Ex. No. | Structure | Analytical data |
|---|---|---|
| 75 | 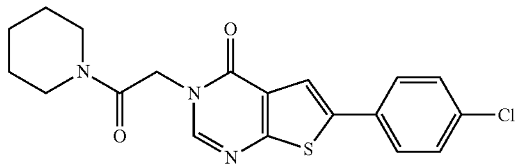 [SMILES: O=C(Cn1cnc2sc(-c3ccc(Cl)cc3)cc2c1=O)N1CCCCC1] | ¹H NMR (400 MHz, DMSO-d₆), δ (ppm): 8.32 (s, 1H), 7.84 (s, 1H), 7.81 (d, J = 8.4 Hz, 1H), 7.5 (d, J = 8.4 Hz, 1H), 4.94 (s, 2H), 3.5 (brs, 2H), 3.44 (brs, 2H), 1.61 (brs, 4H), 1.46 (brs, 2H). Calculated (M + H): 388.08; Found (M + H): 388.1. HPLC purity: 96.23% |
| 76 | 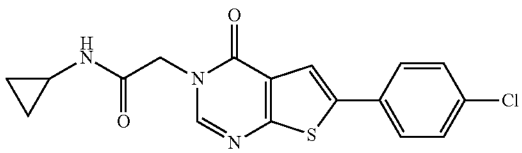 [SMILES: O=C(Cn1cnc2sc(-c3ccc(Cl)cc3)cc2c1=O)NC1CC1] | ¹H NMR (400 MHz, DMSO-d₆) δ (ppm): 8.36 (s, 1H), 8.34 (s, 1H), 7.84 (s, 1H), 7.80 (d, J = 8.4 Hz, 2H), 7.51 (d, J = 8.4 Hz, 2H), 4.72 (s, 2H), 2.65-2.63 (m, 1H), 0.64-0.62 (m, 2H), 0.42 (brs, 2H); Calculated (M + H): 360.05, Found (M + H): 360.1. HPLC purity: 96.49% |
| 77 | 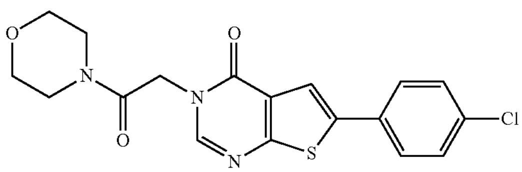 [SMILES: O=C(Cn1cnc2sc(-c3ccc(Cl)cc3)cc2c1=O)N1CCOCC1] | ¹H NMR (400 MHz, DMSO-d₆) δ (ppm): 8.31 (s, 1H), 7.85 (s, 1H), 7.81 (d, J = 8.4 Hz, 2H), 7.51 (d, J = 8.4 Hz, 2H), 4.97 (s, 2H), 3.66 (d, J = 4.0 Hz, 2H), 3.58 (d, J = 4.0 Hz, 4H), 3.45 (s, 2H); Calculated (M + H): 390.06, Found (M + H): 390.1. HPLC purity: 99.45% |
| 78 | 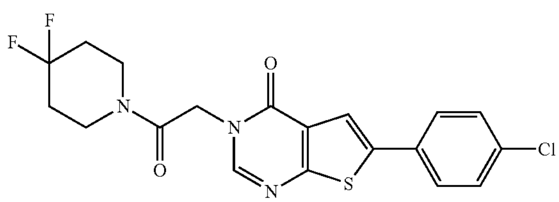 [SMILES: O=C(Cn1cnc2sc(-c3ccc(Cl)cc3)cc2c1=O)N1CCC(F)(F)CC1] | ¹H NMR (400 MHz, DMSO-d₆) δ (ppm): 8.31 (s, 1H), 7.86 (s, 1H), 7.81 (d, J = 8.4 Hz, 2H), 7.50 (d, J = 8.4 Hz, 2H), 5.02 (s, 2H), 3.67 (brs, 2H), 3.59 (brs, 2H), 2.14 (brs, 2H), 1.95 (brs, 2H); Calculated (M + H): 424.06, Found (M + H): 424.3. HPLC purity: 99.59% |

Example 79: 5-(4-Chloro-phenyl)-6-methyl-3-(2-oxo-2-pyrrolidin-1-yl-ethyl)-3H-thieno[2,3-d]pyrimidin-4-one

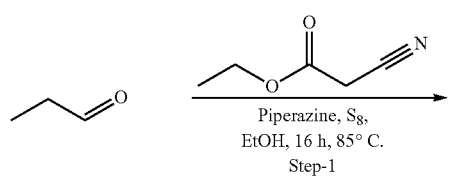

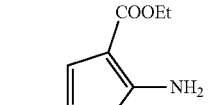

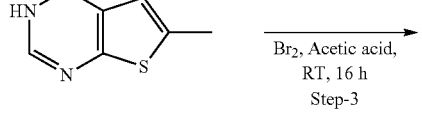

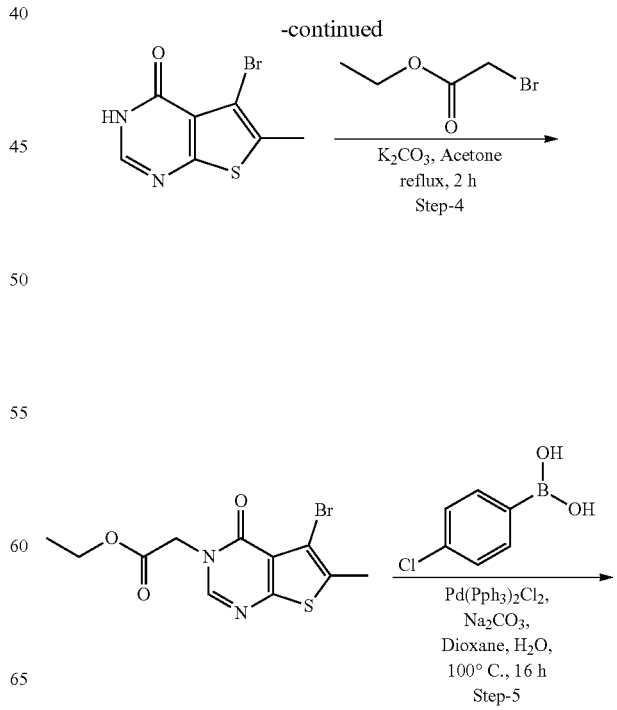

57

-continued

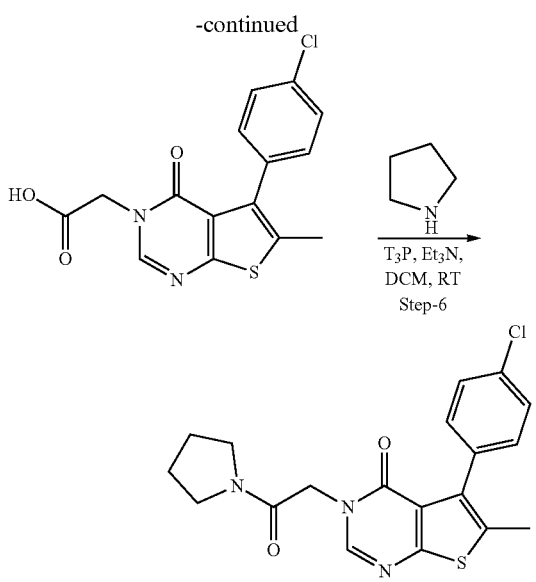

Step 1: Ethyl 2-amino-5-methylthiophene-3-carboxylate

To a solution of propionaldehyde (5.0 g, 44.16 mmol) and ethyl 2-cyanoacetate (6.33 g, 88.33 mmol) in ethanol (200 mL) was added piperazine (19.01 g, 52.99 mmol) followed by $S_8$ (1.69 g, 52.99 mmol). The reaction mixture was heated at 85° C. for 16 h. After completion of the reaction, the reaction mixture was diluted with water (200 mL) and extracted with ethyl acetate (3×200 mL). The combined organic layer was dried over anhydrous sodium sulphate, filtered and concentrated to get the crude product which was purified by silica gel column chromatography using 10% ethyl acetate in hexane to afford the title compound ethyl 2-amino-5-methylthiophene-3-carboxylate (2.3 g, 28% yield) as yellow oily liquid.

Calculated (M+H): 186.05; Found (M+H): 186.

Step 2: 6-methylthieno[2,3-d]pyrimidin-4(3H)-one

A suspension of ethyl 2-amino-5-methylthiophene-3-carboxylate (2.3 g, 0.43 mmol) and form amide (28 mL) was heated at 180° C. for 16 h. After completion of the reaction, the reaction mixture was quenched with water (100 mL) and stirred for 30 minutes. The precipitated solid was filtered and washed with pentane and dried under suction to get the title compound 6-methylthieno[2,3-d]pyrimidin-4(3H)-one (1.0 g, crude) as off white solid.

Calculated (M+H): 167.02; Found (M+H): 167.1.

Step 3: 5-bromo-6-methylthieno[2,3-d]pyrimidin-4(3H)-one

To a solution of 6-methylthieno[2,3-d]pyrimidin-4(3H)-one (1.0 g, 6.02 mmol) in acetic acid (20 mL) was added bromine (0.46 mL, 18.05 mmol) drop-wise at room temperature. The reaction mixture was stirred at the same temperature for 16 h. After completion of the reaction, the reaction mixture was concentrated, the residue was diluted with saturated sodium bicarbonate solution and extracted with ethyl acetate (3×100 mL). The combined organic layer was dried over anhydrous sodium sulphate, filtered and concentrated to get crude product which was purified by silica gel column chromatography using 8% methanol in dichloromethane to afford the title compound 5-bromo-6-methylthieno[2,3-d]pyrimidin-4(3H)-one (0.54 g, 36.7% yield) as off white solid.

Calculated (M+H): 244.93; Found (M+H): 245.1.

Step 4: Ethyl 2-(5-bromo-6-methyl-4-oxothieno[2,3-d]pyrimidin-3(4H)-yl)acetate To a solution of 5-bromo-6-methylthieno[2,3-d]pyrimidin-4(3H)-one (0.54 g, 2.20 mmol) in acetone (20 mL), ethyl bromoacetate (0.8 mL, 4.40 mmol) was added followed by potassium carbonate (0.91 g, 6.6 mmol). The reaction mixture was heated at 55° C. for 2 h. After completion of the reaction, the reaction mixture was filtered and the filtrate was concentrated. The crude product was purified by silica gel column chromatography using 15% ethyl acetate in hexane to afford the title compound ethyl 2-(5-bromo-6-methyl-4-oxothieno[2,3-d]pyrimidin-3(4H)-yl)acetate (0.4 g, 54% yield) as off-white solid.

Calculated (M+H): 330.97; Found (M+H): 331.2.

Step 5: 2-(5-(4-chlorophenyl)-6-methyl-4-oxothieno[2,3-d]pyrimidin-3(4H)-yl)acetic Acid To a solution of ethyl 2-(5-bromo-6-methyl-4-oxothieno[2,3-d]pyrimidin-3(4H)-yl)acetate (0.1 g, 0.30 mmol) in 1,4-dioxane:water mixture (10 mL, 4:1), 4-chlorophenyl) boronic acid (0.06 g, 0.39 mmol), sodium carbonate (0.1 g, 0.96 mmol) were added and the reaction mixture was purged the mixture with argon for 30 minutes. Then bis(triphenylphosphine)palladium(II) dichloride (0.02 g, 0.03 mmol) was added and the reaction mixture was stirred at 100° C. for 16 h. After completion of the reaction, the reaction mixture was diluted with water (50 mL), extracted with ethyl acetate (2×50 mL) and the organic layer was discarded. The aqueous layer pH was adjusted to acidic by the addition of 1.5N hydrochloric acid solution and extracted with ethyl acetate (3×50 mL). The combined organic layer was dried over anhydrous sodium sulphate, filtered and concentrated to get crude product which was purified by silica gel column chromatography using 30% ethyl acetate in hexane to afford the title compound ethyl 2-(5-(4-chlorophenyl)-6-methyl-4-oxothieno[2,3-d]pyrimidin-3(4H)-yl)acetic acid (0.06 g, 59.4% yield) as off-white solid.

Calculated (M+H): 335.02; Found (M+H): 335.2.

Step 6: 5-(4-chlorophenyl)-6-methyl-3-(2-oxo-2-(pyrrolidin-1-yl)ethyl)thieno[2,3-d]pyrimidin-4(3H)-one To a stirred solution of 2-(5-(4-chlorophenyl)-6-methyl-4-oxothieno[2,3-d]pyrimidin-3(4H)-yl)acetic acid (0.06 g, 0.02 mmol) in dichloromethane (20 mL), triethylamine (0.09 g, 0.93 mmol) was added at room temperature followed by pyrrolidine (0.03 g, 0.37 mmol). Then propylphosphonic anhydride solution ($T_3P$) (1.67 mL, 0.28 mmol, 50% sol in ethyl acetate) was added and the RM stirred at RT for 16 h. After completion of the reaction, the reaction mixture was diluted with water (10 mL) and extracted with dichloromethane (2×50 mL). The combined organic layer was dried over anhydrous sodium sulfate, filtered and concentrated to get crude compound which was washed with pentane (3×10 mL) to get the title compound 3-bromo-5-(2-(3-fluoropyrrolidin-1-yl)-2-oxoethyl)thieno[3,2-c]pyridin-4(5H)-one (0.01 g, 15.9% yield) as brown solid.

$^1$H NMR (400 MHz, DMSO-$d_6$) δ (ppm): 8.26 (s, 1H), 7.43 (d, J=8.0 Hz, 2H), 7.28 (d, J=8 Hz, 2H), 4.73 (s, 2H), 3.46 (t, J=6.4 Hz, 2H), 2.31 (s, 3H), 1.92-1.89 (m, 2H), 1.78-1.75 (m, 2H). 2H merged with DMSO water peak.

Calculated (M+H): 388.08; Found M+H: 388.1.

HPLC purity: 98.93%.

Examples 80-84: The Following Compounds were Prepared by the Method Described Above

| Ex. No. | Structure | Analytical Data |
|---|---|---|
| 80 | 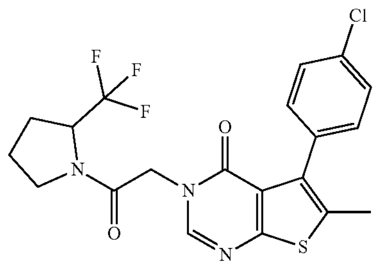 [SMILES: Cc1sc2ncn(CC(=O)N3CCCC3C(F)(F)F)c(=O)c2c1-c1ccc(Cl)cc1] | $^1$H NMR (400 MHz, DMSO-d$_6$) δ (ppm): 8.29-8.26 (s, 1H), 7.41 (d, J = 8.4 Hz, 2H), 7.27 (d, J = 8.4 Hz, 2H), 5.02-4.68 (m, 3H), 3.62 (brs, 2H), 2.31 (s, 3H), 2.13-1.88 (m, 4H). Calculated M + H: 456.07; Found M + H: 456.1. HPLC purity: 99.75% |
| 81 | 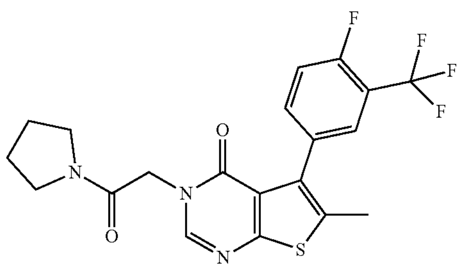 [SMILES: Cc1sc2ncn(CC(=O)N3CCCC3)c(=O)c2c1-c1ccc(F)c(C(F)(F)F)c1] | $^1$H NMR (400 MHz, DMSO-d6) δ (ppm): 8.26 (s, 1H), 7.65-7.64 (m, 2H), 7.54-7.49 (t, J = 10 Hz, 2H), 4.73 (s, 2H), 3.47-3.46 (m, 2H), 3.25 (t, J = 6.8 Hz, 2H), 2.32 (s, 3H), 1.91-1.86 (m, 2H), 1.78-1.73 (m, 2H). Calculated (M + H): 440.1; Found (M + H): 440.3. HPLC purity: 98.97% |
| 82 | 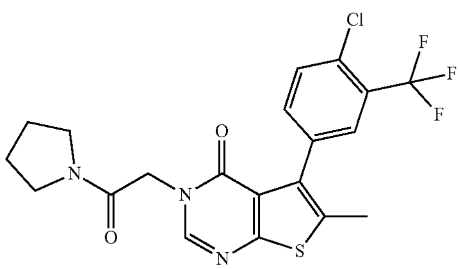 [SMILES: Cc1sc2ncn(CC(=O)N3CCCC3)c(=O)c2c1-c1ccc(Cl)c(C(F)(F)F)c1] | $^1$H NMR (400 MHz, DMSO-d$_6$) δ (ppm): 8.26 (s, 1H), 7.72 (d, J = 8.8 Hz, 2H), 7.601-7.581 (d, J = 8 Hz, 2H), 4.73 (s, 2H), 3.45 (t, J = 6.4 Hz, 2H), 3.27 (t, J = 13.6 Hz, 2H), 2.33 (s, 3H), 1.91-1.86 (m, 2H), 1.78-1.73 (m, 2H). Calculated (M + H): 456.07; Found (M + H): 456.3. HPLC purity: 99.59% |
| 83 | 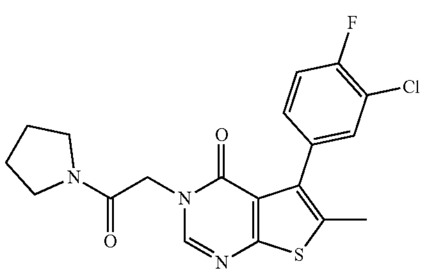 [SMILES: Cc1sc2ncn(CC(=O)N3CCCC3)c(=O)c2c1-c1ccc(F)c(Cl)c1] | $^1$H NMR (400 MHz, DMSO-d$_6$) δ (ppm): 8.25 (s, 1H), 7.47 (dd, J = 1.6 Hz, 7.2 Hz, 1H), 7.41 (t, J = 9.2 Hz, 1H), 7.28-7.25 (m, 2H), 4.73 (s, 2H), 3.46 (t, J = 7.2 Hz, 2H), 3.27 (t, J = 9.2 Hz, 2H), 2.31 (s, 3H), 1.91-1.86 (m, 2H), 1.79-1.74 (m, 2H). Calculated (M + H): 406.07; Found (M + H): 406.1. HPLC purity: 99.34% |
| 84 | 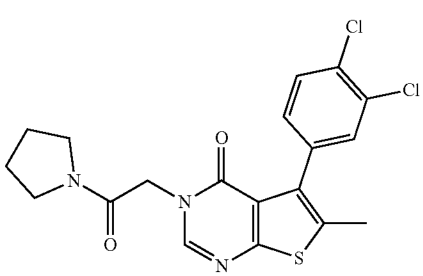 [SMILES: Cc1sc2ncn(CC(=O)N3CCCC3)c(=O)c2c1-c1ccc(Cl)c(Cl)c1] | $^1$H NMR (400 MHz, DMSO-d$_6$) δ (ppm): 8.25 (s, 1H), 7.62 (d, J = 8 Hz, 1H), 7.51 (d, J = 1.2 Hz, 1H), 7.26 (dd, J$_1$ = 1.2 Hz, J$_2$ = 8 Hz, 1H), 4.73 (s, 2H), 3.46 (t, J = 6.8 Hz, 2H), 3.26 (t, J = 7.6 Hz, 2H), 2.32 (s, 3H), 1.93-1.86 (m, 2H), 1.78-1.72 (m, 2H). Calculated (M + H): 422.04; Found (M + H): 422.0; HPLC purity: 99.09%. |

Example 85: 5-(4-chloro-3-(trifluoromethyl)phenyl)-4-oxothieno[2,3-d]pyrimidin-3(4H)-yl pyrrolidine-1-carboxylate

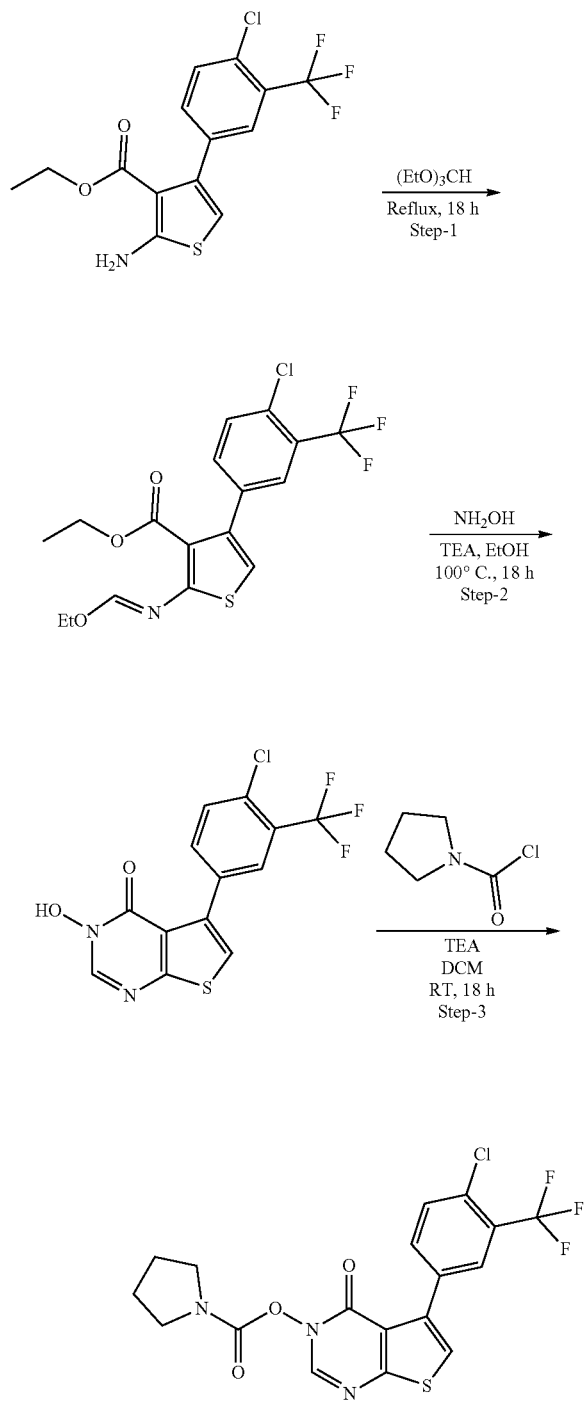

Step 1: (E)-ethyl 4-(4-chloro-3-(trifluoromethyl)phenyl)-2-((ethoxymethylene)amino) thiophene-3-carboxylate A mixture of ethyl 2-amino-4-(4-chloro-3-(trifluoromethyl)phenyl)thiophene-3-carboxylate (1 g) and triethyl orthoformate (25 mL) was refluxed for 18 h. After completion of the reaction, the reaction mixture was concentrated and dried to afford the title compound (E)-ethyl 4-(4-chloro-3-(trifluoromethyl)phenyl)-2-((ethoxymethylene)amino) thiophene-3-carboxylate (1.2 g, crude) as a brownish semi solid.

$^1$H NMR (400 MHz, DMSO-$d_6$) δ (ppm): 8.15 (s, 1H), 7.72 (d, J=8.4 Hz, 1H), 7.67 (s, 1H), 7.59 (d, J=16.4 Hz, 1H), 7.26 (s, 1H), 4.29-4.24 (m, 2H), 4.07-4.02 (m, 2H), 1.29 (t, J=7.2 Hz, 3H), 1.02 (t, J=6.8 Hz, 3H).

Step 2: 5-(4-chloro-3-(trifluoromethyl)phenyl)-3-hydroxythieno[2,3-]pyrimidin-4(3H)-one To a suspension of hydroxylamine hydrochloride (0.43 g, 6.16 mmol) in ethanol (30 mL) was added triethylamine (1.11 mL, 8.00 mmol) followed by (E)-ethyl 4-(4-chloro-3-(trifluoromethyl)phenyl)-2-((ethoxymethylene)amino)thiophene-3-carboxylate (0.5 g, 1.23 mmol). The reaction mixture was heated at 100° C. for 18 h. After completion of the reaction, the reaction mixture was concentrated, the residue was diluted with water (100 mL) and extracted with ethyl acetate (3×10 mL). The combined organic layer was concentrated to get crude product which was purified by silica gel column chromatography using 6% methanol in DCM to afford the title compound 5-(4-chloro-3-(trifluoromethyl) phenyl)-3-hydroxythieno[2,3-d]pyrimidin-4(3H)-one (0.23 g 55% yield) as a brownish solid.

Calculated (M−H): 344.98; Found (M−H): 345.0.

Step 3: 5-(4-chloro-3-(trifluoromethyl)phenyl)-4-oxothieno[2,3-d]pyrimidin-3(4H)-yl pyrrolidine-1-carboxylate To a solution of 5-(4-chloro-3-(trifluoromethyl)phenyl)-3-hydroxythieno[2,3-d]pyrimidin-4(3H)-one (0.05 g, 0.14 mmol) in dichloromethane (10 mL), triethylamine (0.06 ml, 0.43 mmol) was added followed by pyrrolidine-1-carbonyl chloride (0.04 ml, 0.36 mmol) at 0° C. The reaction mixture was stirred at room temperature for 18 h. After completion of the reaction, the reaction mixture was diluted with water (50 mL) and extracted with dichloromethane (2×30 mL). The combined organic layer was dried over anhydrous sodium sulphate, filtered and concentrated to get crude product which was purified by column chromatography using 30% ethyl acetate in hexane to afford the title compound 5-(4-chloro-3-(trifluoromethyl)phenyl)-4-oxothieno[2,3-d]pyrimidin-3(4H)-yl pyrrolidine-1-carboxylate (0.03 g 55% yield) as a off-white solid.

Calculated (M−H): 444.03; Found (M−H): 444.0.

$^1$H NMR (400 MHz, DMSO-$d_6$) δ (ppm): 8.75 (s, 1H), 7.95 (s, 1H), 7.86 (s, 1H), 7.81-7.78 (m, 1H), 7.75 (d, J=8.4 Hz, 1H), 3.51 (t, J=6.8 Hz, 2H), 3.35 (t, J=6.4 Hz, 2H), 1.96-1.82 (m, 4H).

HPLC purity: 99.38%.

Examples 86-88: The Following Compounds were Prepared by the Method Described Above

| Ex. No. | Structure | Analytical Data |
|---|---|---|
| 86 | 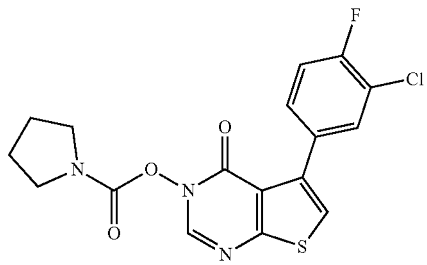 [SMILES: O=C(On1cnc2scc(-c3ccc(F)c(Cl)c3)c2c1=O)N1CCCC1] | $^1$H NMR (400 MHz, DMSO-$d_6$) δ (ppm): 8.73 (s, 1H), 7.74 (s, 1H), 7.72-7.69 (dd, J = 2.4 Hz, 7.2 Hz, 1H), 7.51-7.47 (m, 1H), 7.42 (t, J = 9.2 Hz, 1H), 3.51 (t, J = 6.8 Hz, 2H), 3.35 (t, J = 6.8 Hz, 2H), 1.95-1.81 (m, 4H). Calculated (M + H): 394.04; Found (M + H): 394.0. HPLC purity: 99.46% |
| 87 | 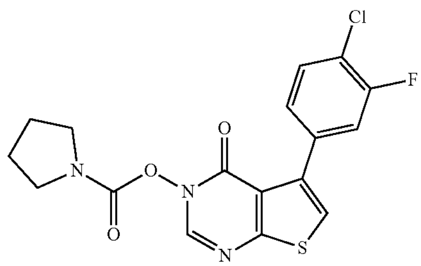 [SMILES: O=C(On1cnc2scc(-c3ccc(Cl)c(F)c3)c2c1=O)N1CCCC1] | $^1$H NMR (400 MHz, DMSO-$d_6$) δ (ppm): 8.75 (s, 1H), 7.78 (s, 1H), 7.62-7.53 (m, 2H), 7.37-7.35 (dd, J = 1.2 Hz, 8.4 Hz, 1H), 3.51 (t, J = 6.4 Hz, 2H), 3.36 (t, J = 6.4 Hz, 2H), 1.95-1.81 (m, 4H). Calculated (M + H): 394.04; Found (M + H): 394.0. HPLC purity: 99.17% |
| 88 | 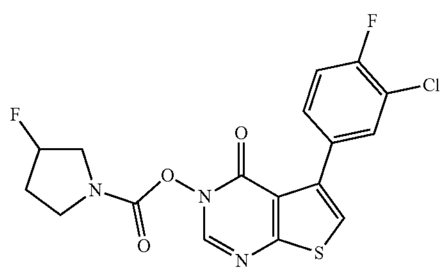 [SMILES: O=C(On1cnc2scc(-c3ccc(F)c(Cl)c3)c2c1=O)N1CCC(F)C1] | $^1$H NMR (400 MHz, DMSO-$d_6$) δ (ppm): 8.78 (d, J = 4.4 Hz, 1H), 7.75 (s, 1H), 7.71 (d, J = 6.0 Hz, 1H), 7.49-7.48 (m, 1H), 7.42 (t, J = 8.8 Hz, 1H), 5.48-5.29 (m, 1H), 3.81-3.27 (m, 4H), 2.25-2.14 (m, 2H). Calculated (M + H): 412.03; Found (M + H): 412.0. HPLC purity: 99.77% |

Example 89: N-(5-(4-chloro-3-(trifluoromethyl)phenyl)-4-oxothieno[2,3-d]pyrimidin-3(4H)-yl)pyrrolidine-1-carboxamide

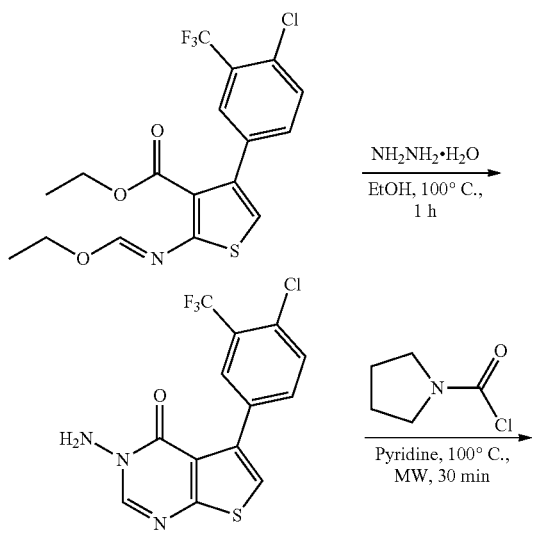

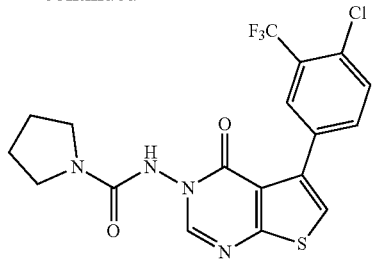

Step 1: 3-amino-5-(4-chloro-3-(trifluoromethyl)phenyl)thieno[2,3-d]pyrimidin-4(3H)-one To a stirred solution of (E)-ethyl 4-(4-chloro-3-(trifluoromethyl)phenyl)-2-((ethoxymethylene)amino)thiophene-3-carboxylate (0.5 g, 1.23 mmol) in ethanol (20 mL), hydrazine hydrate (5.0 mL) was added and the resulting reaction mixture was stirred at 100° C. for 1 h. After completion of the reaction, the reaction mixture was evaporated to afford the title compound 3-amino-5-(4-chloro-3-(trifluoromethyl)phenyl)thieno[2,3-d]pyrimidin-4(3H)-one (0.29 g, crude) as off-white solid.

Calculated (M+H): 346.0; Found (M+H): 346.0.

Step 2: N-(5-(4-chloro-3-(trifluoromethyl)phenyl)-4-oxothieno[2,3-d]pyrimidin-3(4H)-yl)pyrrolidine-1-carboxamide To a stirred solution of 3-amino-5-(4-chloro-3-(trifluoromethyl)phenyl)thieno[2,3-d]pyrimidin-4(3H)-one (0.07 g, 0.20 mmol) in pyridine (1.0 mL), pyrrolidine-1-carbonyl chloride (0.06 mL, 0.51 mmol) was added at room temperature and the reaction mixture was heated at 120° C. for 30 minutes under microwave irradiation. After completion of the reaction, the reaction mixture was diluted with ethyl acetate (50 mL) and washed with saturated citric acid (10 mL) and saturated sodium bicarbonate solution (10 mL). The organic layer was dried over anhydrous sodium sulphate, filtered and evaporated to get the crude product which was purified by preparative HPLC (column: Inertsil ODS 3V (250 mm×4.6 mm×5µ), mobile phase (A): 0.01% NH₄OH in water; mobile phase (B): acetonitrile, flow rate: 1.0 mL/min, T/% B: 0/10, 10/70, 25/70, 27/10, 30/10) to afford the title compound N-(5-(4-chloro-3-(trifluoromethyl)phenyl)-4-oxothieno[2,3-d]pyrimidin-3(4H)-yl)pyrrolidine-1-carboxamide as off-white solid (0.01 g, 14.4% yield).

¹H-NMR (400 MHz, DMSO-d₆) δ (ppm): 9.60 (s, 1H), 8.39 (s, 1H), 7.94 (s, 1H), 7.81 (s, 1H), 7.78-7.74 (m, 2H), 3.31 (brs, 4H), 1.83 (brs, 4H).
Calculated (M+H): 443.05; Found (M+H): 443.0.
HPLC purity: 99.93%.

Example 90: The Following Compound was Prepared by the Method Described Above

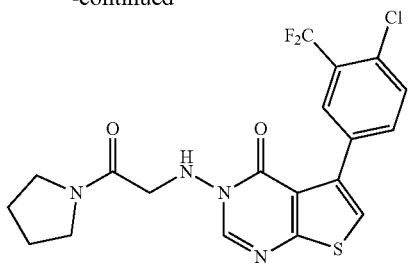

To a stirred solution of 3-amino-5-(4-chloro-3-(trifluoromethyl)phenyl)thieno[2,3-d]pyrimidin-4(3H)-one (0.05 g, 0.15 mmol) in acetone (10 mL), potassium carbonate (0.06 g, 0.43 mmol) and 2-chloro-1-(pyrrolidin-1-yl)ethan-1-one (0.06 g, 0.43 mmol) were added at room temperature and the reaction mixture was stirred at 55° C. for 16 h. The reaction mixture was filtered and the filtrate was evaporated to get crude product which was purified by silica gel column chromatography using 5% methanol in dichloromethane to afford title compound 5-(4-chloro-3-(trifluoromethyl)phenyl)-3-((2-oxo-2-(pyrrolidin-1-yl)ethyl)amino)thieno[2,3-d]pyrimidin-4(3H)-one (0.015 g, 22.7% yield) as off-white solid.

¹H-NMR (400 MHz, DMSO-d6) δ (ppm): 8.57 (s, 1H), 8.01 (s, 1H), 7.84 (d, J=8.4 Hz, 1H), 7.77-7.73 (m, 2H), 6.68 (brs, 1H), 3.78 (d, J=4.0 Hz, 2H), 1.83-1.78 (m, 2H), 1.75-1.70 (m, 2H). 4H merged with DMSO water peak.
Calculated (M+H): 457.06, Found (M+H): 457.0.
HPLC purity: 99.51%.

| Ex. No. | Structure | Analytical Data |
|---|---|---|
| 90 | 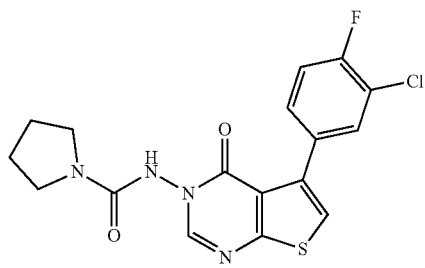 [SMILES: O=C(Nn1cnc2scc(-c3ccc(F)c(Cl)c3)c2c1=O)C1CCCC1] | ¹H-NMR (400 MHz, DMSO-d₆) δ (ppm): 9.57 (s, 1H), 8.38 (s, 1H), 7.70-7.67 (m, 2H), 7.47-7.41 (m, 2H), 3.37 (s, 4H), 1.84 (s, 4H); Calculaled (M + H): 393.05, Found (M + H): 393.0, HPLC purity: 97.29% |

Example 91: 5-(4-chloro-3-(trifluoromethyl)phenyl)-3-((2-oxo-2-(pyrrolidin-1-yl)ethyl)amino)thieno[2,3-d]pyrimidin-4(3H)-one

Example 92: 5-(4-chloro-3-(trifluoromethyl)phenyl)-3-(2-oxo-2-(pyrrolidin-1-yl)ethoxy)thieno[2,3-d]pyrimidin-4(3H)-one

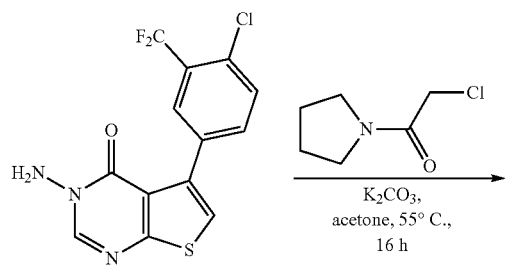

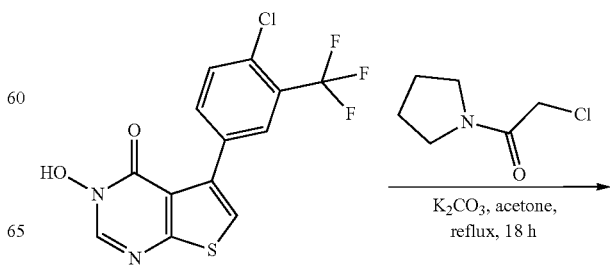

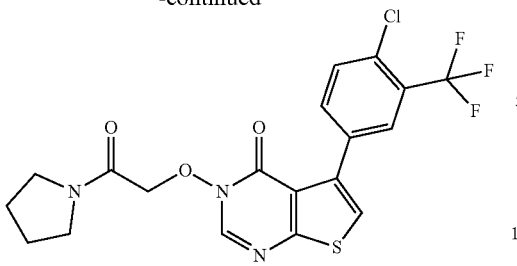

A mixture of 5-(4-chloro-3-(trifluoromethyl)phenyl)-3-hydroxythieno[2,3-d]pyrimidin-4(3H)-one (0.07 g, 0.20 mmol), 2-chloro-1-(pyrrolidin-1-yl)ethanone (0.06 g, 0.40 mmol) and potassium carbonate (0.08 g, 0.61 mmol) in acetone (10 mL) was refluxed for 18 h. After completion of the reaction, the reaction mixture was filtered and the filtrate was concentrated to get the crude product which was purified by silica gel column chromatography using 70% ethyl acetate in hexane to afford the title compound 5-(4-chloro-3-(trifluoromethyl)phenyl)-3-(2-oxo-2-(pyrrolidin-1-yl)ethoxy)thieno[2,3-d]pyrimidin-4(3H)-one (0.02 g, 22% yield) as a off-white solid.

Calculated (M+H): 458.05; Found (M+H): 458.0. $^1$H NMR (400 MHz, DMSO-$d_6$) δ (ppm): 8.85 (s, 1H), 8.02 (s, 1H), 7.86 (s, 1H), 7.79 (s, 1H), 7.74 (d, J=8.4 Hz, 1H), 4.96 (s, 2H), 3.29-3.24 (m, 4H), 1.83-1.78 (m, 2H), 1.74-1.69 (m, 2H).

HPLC purity: 99.50%

Example 93: The Following Compound was Prepared by the Method Described Above

| Ex. No. | Structure | Analytical Data |
|---|---|---|
| 93 | 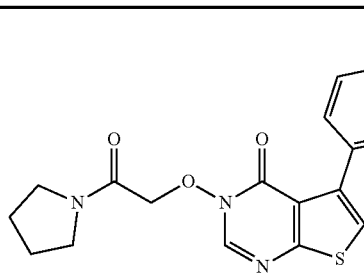 | $^1$H NMR (400 MHz, DMSO-$d_6$) δ (ppm): 8.84 (s, 1H), 7.78-7.76 (m, 1H), 7.67 (s, 1H), 7.56-7.54 (m, 1H), 7.42 (t, J = 9.2 Hz, 1H), 4.96 (s, 2H), 3.27 (s, 2H), 1.83-1.74 (m, 2H), 1.73-1.69 (m, 2H). 2H merged with DMSO water peak. Calculated (M + H): 408.05; Found (M + H): 408.0. HPLC purity: 98.68% |

Example 94: (E)-5-(4-chloro-3-(trifluoromethyl)phenyl)-3-((pyrrolidin-1-ylmethylene)amino)thieno[2,3-d]pyrimidin-4(3H)-one

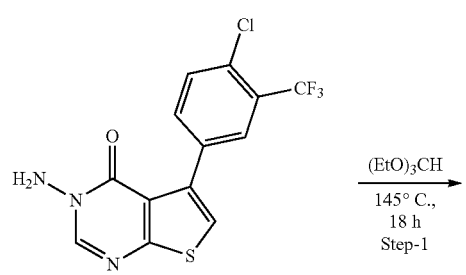

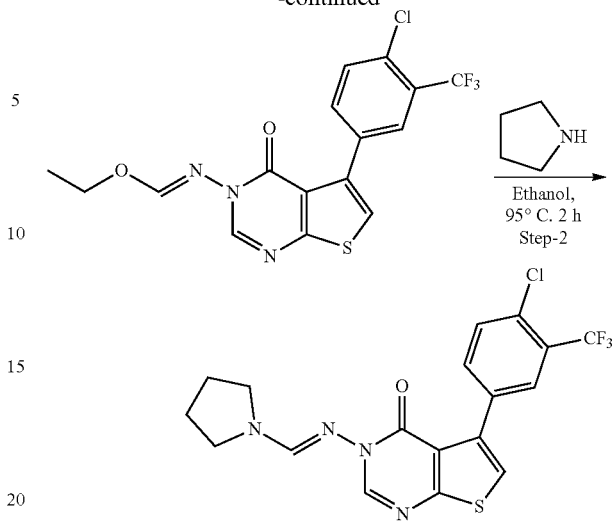

Step 1: (E)-ethyl N-(5-(4-chloro-3-(trifluoromethyl)phenyl)-4-oxothieno[2,3-d]pyrimidin-3(4H)-yl)formimidate A mixture of 3-amino-5-(4-chloro-3-(trifluoromethyl)phenyl)thieno[2,3-d]pyrimidin-4(3H)-one (0.25 g) and triethyl orthoformate (10 mL) was refluxed for 18 h. After completion of the reaction, the reaction mixture was concentrated and dried to afford the title compound (E)-ethyl N-(5-(4-chloro-3-(trifluoromethyl)phenyl)-4-oxothieno[2,3-d]pyrimidin-3(4H)-yl)formimidate (0.29 g, crude).

Calculated (M+H): 402.02; Found (M+H): 402.0.

Step 2: (E)-5-(4-chloro-3-(trifluoromethyl)phenyl)-3-((pyrrolidin-1-ylmethylene)amino)thieno[2,3-d]pyrimidin-4(3H)-one A mixture of (E)-ethyl N-(5-(4-chloro-3-(trifluoromethyl)phenyl)-4-oxothieno[2,3-d]pyrimidin-3(4H)-yl)formimidate (0.29 g, 0.72 mmol) and pyrrolidine (0.13 g, 1.81 mmol) in ethanol (10 mL) was heated at 95° C. for 2 h. After completion of the reaction, the reaction mixture was concentrated to get the crude product which was purified by silica gel column chromatography using 70% ethyl acetate in hexane to afford the title compound (E)-5-(4-chloro-3-(trifluoromethyl)phenyl)-3-((pyrrolidin-1-ylmethylene)amino)thieno[2,3-d]pyrimidin-4(3H)-one (0.09 g, 31% yield) as a white solid.

Calculated (M+H): 427.05.

Found (M+H): 427.0; ¹H NMR (400 MHz, DMSO-d₆) δ (ppm): 8.33 (s, 1H), 8.13 (s, 1H), 7.94 (d, J=2 Hz, 1H), 7.80-7.78 (m, 1H), 7.71 (d, J=6.8 Hz, 2H), 3.40-3.30 (m, 4H), 1.90-1.82 (m, 4H).

HPLC purity: 99.07%.

Example 95: N-(5-(4-chloro-3-(trifluoromethyl)phenyl)-4-oxothieno[2,3-d]pyrimidin-3(4H)-yl)cyclopentanecarboxamide

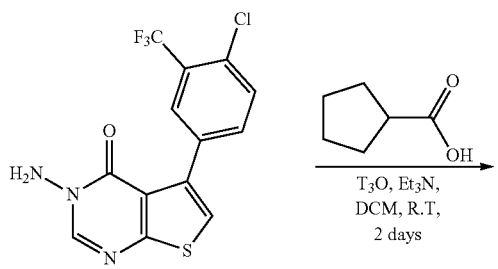

mixture was diluted with water (10 mL) and extracted with dichloromethane (3×15 mL). The combined organic layer was dried over anhydrous sodium sulfate, filtered and evaporated to get crude product which was purified by preparative HPLC (Column: Inertsil ODS 3V (250 mm×4.6 mm×5µ), mobile phase (A): 0.01% ammonia in water, mobile phase (B): methanol, flow rate: 1.0 mL/min, T/% B: 0/20, 8/80, 25/90, 27/20, 30/20) to afford title compound N-(5-(4-chloro-3-(trifluoromethyl)phenyl)-4-oxothieno[2,3-d]pyrimidin-3(4H)yl)cyclopentanecarboxamide (0.02 g, 15.6% yield) as off white solid.

¹H NMR (400 MHz, DMSO-d₆) δ (ppm): 11.15 (s, 1H), 8.38 (s, 1H), 7.95 (s, 1H), 7.82 (s, 1H), 7.79-7.74 (m, 2H), 2.86-2.78 (m, 1H), 1.83 (s, 2H), 1.74-1.71 (m, 2H), 1.60-1.52 (m, 4H).

Calculated (M+H): 442.05, Found (M+H): 442.3.

HPLC purity: 100%

Example 96: The Following Compound was Prepared by the Method Described Above

| Ex. No. | Structure | Analytical Data |
|---|---|---|
| 96 | 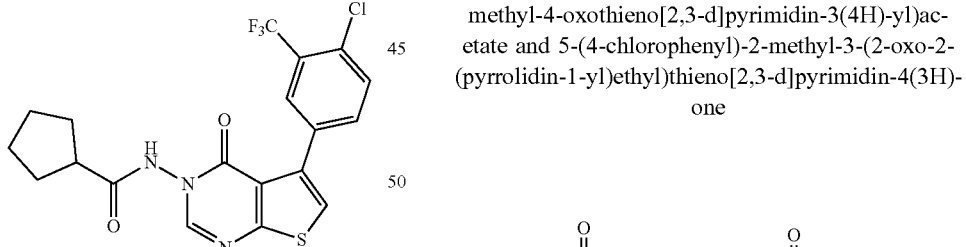 | ¹H-NMR (400 MHz, DMSO-d₆) δ (ppm): 11.11 (s, 1H), 8.37 (s, 1H), 7.70-7.67 (m, 2H), 7.50-7.48 (m, 1H), 7.47-7.40 (m, 1H), 2.87-2.78 (m, 1H), 1.86-1.84 (m, 2H), 1.77-1.69 (m, 2H), 1.61-1.51 (m, 4H); Calculated (M + H): 390.06, Found (M + H): 390.0, HPLC purity: 99.41% |

-continued

To a stirred solution of 3-amino-5-(4-chloro-3-(trifluoromethyl)phenyl)thieno[2,3-d]pyrimidin-4(3H)-one (0.1 g, 0.29 mmol) in dichloromethane (10 mL), triethylamine (0.12 mL, 0.87 mmol) and cyclopentanecarboxylic acid (0.05 g, 0.43 mmol) were added at room temperature and the reaction mixture was stirred at room temperature for 10 minutes. Then propylphosphonic anhydride (T₃P) (0.25 mL, 0.43 mmol, 50% solution in ethyl acetate) was added at 0° C. and the reaction mixture was stirred at room temperature for 2 days. After completion of the reaction, the reaction

Example 97 and 98: Ethyl 2-(5-(4-chlorophenyl)-2-methyl-4-oxothieno[2,3-d]pyrimidin-3(4H)-yl)acetate and 5-(4-chlorophenyl)-2-methyl-3-(2-oxo-2-(pyrrolidin-1-yl)ethyl)thieno[2,3-d]pyrimidin-4(3H)-one

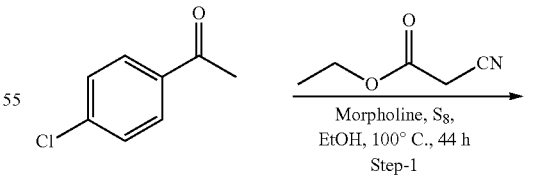
Step-1

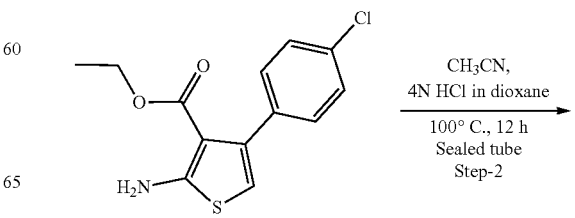
Step-2

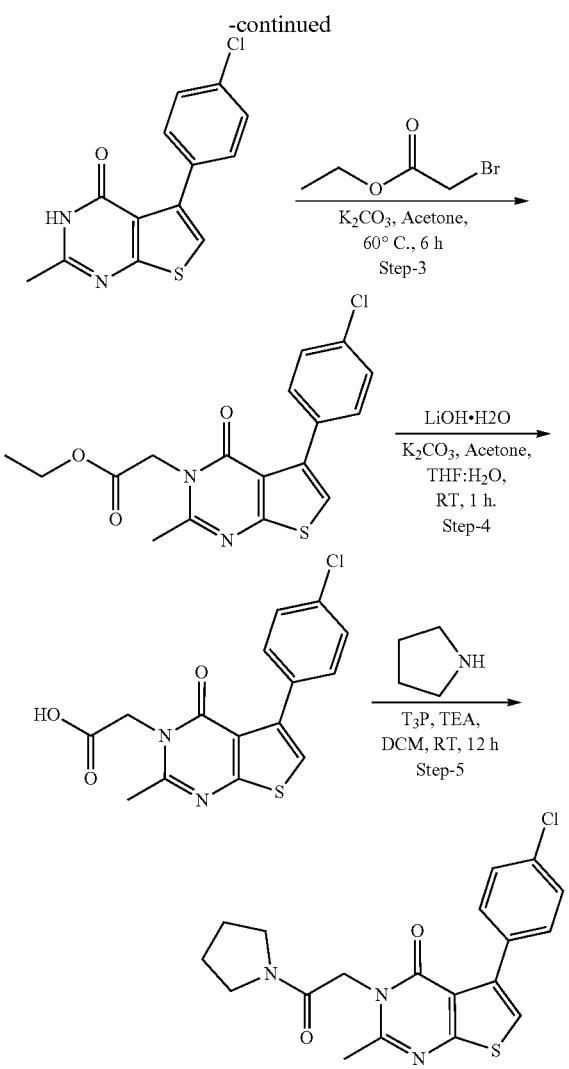

Step 1: Ethyl 2-amino-4-(4-chlorophenyl)thiophene-3-carboxylate

To a stirred solution of 1-(4-chlorophenyl)ethanone (10.0 g, 64.93 mmol) in ethanol (200 mL) were added ethyl 2-cyanoacetate (16.0 ml, 129.87 mmol), morpholine (20 mL, 227.27 mmol), and sulfur (4.0 g, 97.40 mmol) at room temperature and the RM was stirred at 100° C. for 44 h. After completion of the reaction, the RM was concentrated to get the crude product which was purified by silica gel column chromatography using 10% ethyl acetate in hexane to afford the title compound ethyl 2-amino-4-(4-chlorophenyl)thiophene-3-carboxylate (3.9 g, 21.0% yield) as off white solid.

Calculated (M+H): 282.03; Found (M+H): 282.2.

Step 2: 5-(4-chlorophenyl)-2-methylthieno[2,3-d]pyrimidin-4(3H)-one

To a stirred solution of ethyl 2-amino-4-(4-chlorophenyl)thiophene-3-carboxylate (1.0 g, 3.55 mmol) in acetonitrile (8 mL), was added 4N hydrochloric acid in dioxane (18 mL) at room temperature and the RM was stirred at 100° C. for 12 h in a sealed tube. After completion of the reaction, the reaction mixture was cooled to room temperature and diluted with water (100 mL). The precipitated solid was filtered, washed with water (50 mL) and dried under suction to afford the title compound 5-(4-chlorophenyl)-2-methyl-thieno[2,3-d]pyrimidin-4(3H)-one (0.8 g, 88% yield) as off white solid.

Calculated (M+H): 277.01; Found (M+H): 277.0.

Step 3: Ethyl 2-(5-(4-chlorophenyl)-2-methyl-4-oxothieno[2,3-d]pyrimidin-3(4H)-yl)acetate To a stirred solution of 5-(4-chlorophenyl)-2-methylthieno[2,3-d]pyrimidin-4(3H)-one (0.4 g, 1.44 mmol) in acetone (20 mL), potassium carbonate (0.6 g, 4.33 mmol) and ethylbromoacetate (0.48 g, 2.88 mmol) were added at room temperature and the reaction mixture was heated at 60° C. for 6 h. The reaction mixture was filtered and the filtrate was concentrated to get the crude compound which was purified by silica gel column chromatography using 30% ethyl acetate in hexane to get the title compound ethyl 2-(5-(4-chlorophenyl)-2-methyl-4-oxothieno[2,3-d]pyrimidin-3(4H)-yl)acetate (0.38 g, 57.0% yield) as off white solid.

$^1$H NMR (400 MHz, DMSO-$d_6$) δ (ppm): 7.52 (s, 1H), 7.48 (d, J=8.4 Hz, 2H), 7.41 (d, J=8.4 Hz, 2H), 4.86 (s, 2H), 4.16-4.10 (m, 2H), 2.56 (s, 3H), 1.23-1.16 (m, 3H).

Calculated (M+H): 363.05; Found (M+H): 363.1.

HPLC purity: 99.86%.

Step 4: 2-(5-(4-chlorophenyl)-2-methyl-4-oxothieno[2,3-d]pyrimidin-3(4H)-yl)acetic Acid To a stirred solution of ethyl 2-(5-(4-chlorophenyl)-2-methyl-4-oxothieno[2,3-d]pyrimidin-3(4H)-yl)acetate (0.38 g, 1.04 mmol) in tetrahydrofuran:water mixture (20 mL, 4:1), lithium hydroxide monohydrate (0.21 g, 5.23 mmol) was added and the reaction mixture was stirred at room temperature for 1 h. After completion of the reaction, the reaction mixture was evaporated and acidified with 1.5N hydrochloric acid solution. The precipitated solid was filtered, washed with water and dried under suction to get the title compound 2-(5-(4-chlorophenyl)-2-methyl-4-oxothieno[2,3-d]pyrimidin-3(4H)-yl)acetic acid (0.22 g, 62.0% yield) as off white solid.

Calculated (M+H): 335.02; Found (M+H): 335.0.

Step 5: 5-(4-chlorophenyl)-2-methyl-3-(2-oxo-2-(pyrrolidin-1-yl)ethyl)thieno[2,3-d]pyrimidin-4(3H)-one To a stirred solution of (5-(4-chlorophenyl)-2-methyl-4-oxothieno[2,3-d]pyrimidin-3(4H)-yl)acetic acid (0.11 g, 0.32 mmol) in dichloromethane (20 mL) were added triethylamine (0.15 mL, 1.91 mmol) and pyrrolidine (0.03 g, 0.39 mmol) at room temperature and the RM was stirred for 10 minutes. Then propylphosphonic anhydride (T$_3$P) (0.15 mL, 0.49 mmol, 50% solution in ethyl acetate) was added at 0° C. and the RM was stirred at room temperature for 16 h. After completion of the reaction, the reaction mixture was diluted with water (10 mL) and extracted with dichloromethane (3×15 mL). The combined organic layer was dried over anhydrous sodium sulfate, filtered and concentrated to get the crude compound which was purified by silica gel column chromatography using 5% methanol in dichloromethane to afford the title compound 5-(4-chlorophenyl)-2-methyl-3-(2-oxo-2-(pyrrolidin-1-yl)ethyl)thieno[2,3-d]pyrimidin-4(3H)-one (0.021 g, 17.0% yield) as off white solid.

¹H NMR (400 MHz, CDCl₃) δ (ppm): 7.45 (d, J=7.6 Hz, 2H), 7.34 (d, J=8.4 Hz, 2H), 7.02 (s, 1H), 4.81 (s, 2H), 3.56 (t, J=6.8 Hz, 2H), 3.49 (t, J=6.8 Hz, 2H), 2.59 (s, 3H), 2.06-1.99 (m, 2H), 1.91-1.84 (m, 2H).

Calculated (M+H): 388.08; Found (M+H): 388.3.
HPLC: 98.12%.

Example 99: The Following Compounds were Prepared by the Method Described Above

| Ex. No. | Structure | Analytical Data |
|---|---|---|
| 99 | 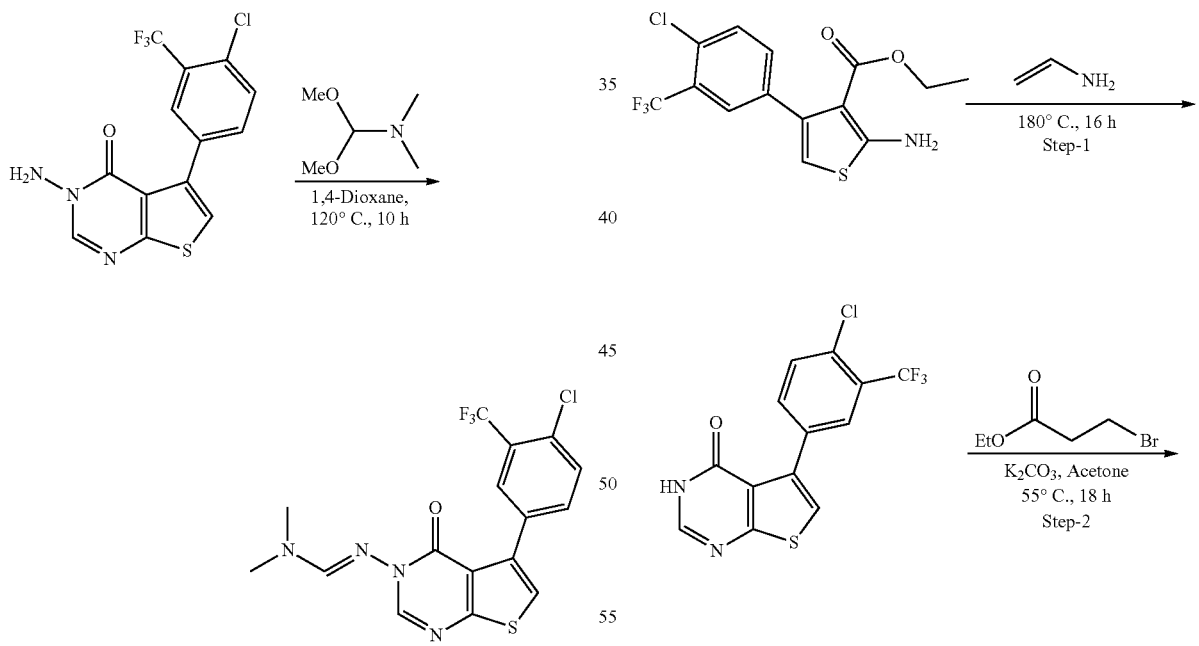 | ¹H NMR (400 MHz, DMSO-d₆) δ (ppm): 7.50-7.47 (m, 3H), 7.41 (d, J = 7.6 Hz, 2H), 5.10-4.71 (m, 3H), 3.71 (brs, 2H), 2.04-1.90 (m, 4H). 3H merged with DMSO residual peak. Calculated (M + H): 456.07; Found (M + H): 456.01; HPLC purity: 99.86% |

Example 100: (E)-N'-(5-(4-chloro-3-(trifluoromethyl)phenyl)-4-oxothieno[2,3-d]pyrimidin-3(4H)-yl)-N,N-dimethylformimidamide To a stirred solution of 3-amino-5-(4-chloro-3-(trifluoromethyl)phenyl)thieno[2,3-d]pyrimidin-4(3H)-one (0.1 g, 0.28 mmol) in 1,4-dioxane (5 mL), was added 1,1-dimethoxy-N,N-dimethylmethanamine (0.05 g, 0.43 mmol) at room temperature and the RM was stirred at 120° C. for 10 h. After completion the reaction, the reaction mixture was diluted with water (20 mL) and extracted with ethyl acetate (3×15 mL). The combined organic layer was dried over anhydrous sodium sulfate, filtered and concentrated to get crude compound which was purified by silica gel column chromatography using 50% ethyl acetate in hexane to afford the title compound (E)-N'-(5-(4-chloro-3-(trifluoromethyl)phenyl)-4-oxothieno[2,3-d]pyrimidin-3(4H)-yl)-N,N-dimethylformimidamide (0.07 g, 68.0% yield) as off white solid.

¹H NMR (400 MHz, DMSO-d₆) δ (ppm): 8.33 (s, 1H), 7.95 (d, J=7.2 Hz, 2H), 7.79 (d, J=8.0 Hz, 1H), 7.73-7.72 (d, J=4.4 Hz, 2H), 2.94 (s, 3H), 2.90 (s, 3H).

Calculated (M+H): 401.04; Found (M+H): 401.0.
HPLC purity: 99.59%

Example 101: 5-(4-chloro-3-(trifluoromethyl)phenyl)-3-(3-oxo-3-(pyrrolidin-1-yl)propyl)thieno[2,3-d]pyrimidin-4(3H)-one

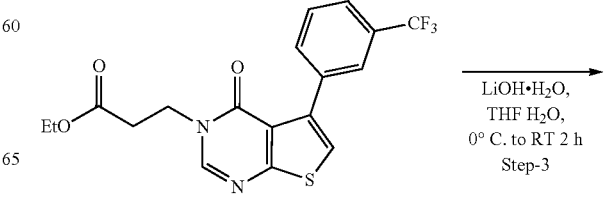

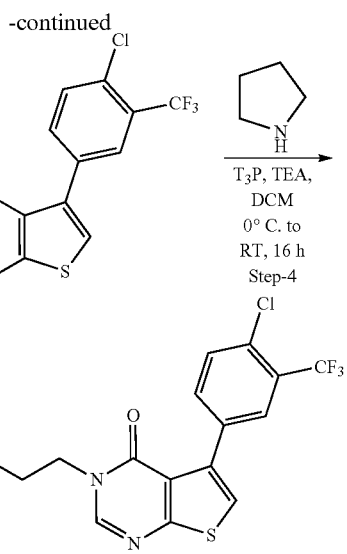

Step 1: 5-(4-chloro-3-(trifluoromethyl)phenyl)thieno[2,3-d]pyrimidin-4(3H)-one A mixture of ethyl 2-amino-4-(4-chloro-3-(trifluoromethyl)phenyl)thiophene-3-carboxylate (3.0 g, 8.58 mmol) and formamide (30 mL) was heated at 180° C. for 16 h. The mixture was allowed to cool to room temperature and diluted with water (150 mL). The precipitated compound was filtered, washed with water and dried under vacuum to afford the title compound 5-(4-chloro-3-(trifluoromethyl)phenyl)thieno[2,3-d]pyrimidin-4(3H)-one (3.2 g, crude) as a brown solid, which was taken for next step without further purification.

Calculated (M+H): 330.98, Found (M+H): 330.0.

Step 2: Ethyl 3-(5-(4-chloro-3-(trifluoromethyl)phenyl)-4-oxothieno[2,3-d]pyrimidin-3(4H)-yl)propanoate To a mixture of 5-(4-chloro-3-(trifluoromethyl)phenyl)thieno[2,3-d]pyrimidin-4(3H)-one (0.4 g, 1.21 mmol) and potassium carbonate (0.5 g, 3.63 mmol) in dry acetone (50 mL) was added ethyl 2-bromoacetate (0.3 g, 2.42 mmol). The resulting mixture was heated at 55° C. for 3 h. The reaction mixture was allowed to cool to room temperature, filtered and the filtrate was concentrated under vacuum to afford crude product, which was purified by silica gel column chromatography using 35% ethyl acetate in hexane to afford the title compound ethyl 3-(5-(4-chloro-3-(trifluoromethyl)phenyl)-4-oxothieno[2,3-d]pyrimidin-3(4H)-yl)propanoate (0.36 g, 69% yield) as white solid.

Calculated (M+H): 431.04, Found (M+1): 431.0.

Step 3: 3-(5-(4-chloro-3-(trifluoromethyl)phenyl)-4-oxothieno[2,3-d]pyrimidin-3(4H)-yl)propanoic Acid To a suspension of ethyl 3-(5-(4-chloro-3-(trifluoromethyl)phenyl)-4-oxothieno[2,3-d]pyrimidin-3(4H)-yl)propanoate (0.36 g, 0.84 mmol) in tetrahydrofuran:water mixture (20 mL, 1:1) was added lithium hydroxide monohydrate (0.1 g, 2.51 mmol) at 0° C. The resulting suspension was gradually allowed to warm to room temperature and stirred for 3 h. The reaction mixture was allowed to cool to 0° C. and acidified with 1.5M hydrochloric acid solution to pH 2 to 3. The precipitated product was filtered, washed with water, dried to obtain the title compound 3-(5-(4-chloro-3-(trifluoromethyl)phenyl)-4-oxothieno[2,3-d]pyrimidin-3(4H)-yl)propanoic acid (0.3 g, 91% yield) as a colorless solid.

Calculated (M+H): 403.0, Found (M+H): 403.0.

Step 4: 5-(4-chloro-3-(trifluoromethyl)phenyl)-3-(3-oxo-3-(pyrrolidin-1-yl)propyl)thieno[2,3-d]pyrimidin-4(3H)-one To a solution of 3-(5-(4-chloro-3-(trifluoromethyl)phenyl)-4-oxothieno[2,3-d]pyrimidin-3(4H)-yl)propanoic acid (0.075 g, 0.19 mmol) in dichloromethane (10 mL) were added pyrrolidine (0.015 g, 0.22 mmol) and triethylamine (0.2 mL, 1.49 mmol). The reaction mixture was cooled to room temperature and 1-propanephosphonic anhydride ($T_3P$) (0.12 mL, 0.37 mmol, 50% solution in ethyl acetate) was added drop-wise. The reaction mixture was allowed to warm to room temperature and stirred for 16 h. The mixture was diluted with dichloromethane (25 mL), washed with water (2×50 mL), brine (30 mL), dried over anhydrous sodium sulfate, filtered and concentrated under reduced pressure to afford crude product, which was purified by silica gel column chromatography using 3% methanol in dichloromethane as eluent to afford the title compound 5-(4-chloro-3-(trifluoromethyl)phenyl)-3-(3-oxo-3-(pyrrolidin-1-yl)propyl)thieno[2,3-d]pyrimidin-4(3H)-one (0.035 g, 41.5% yield) as white solid.

$^1$H NMR (400 MHz, DMSO-$d_6$) δ (ppm): 8.50 (s, 1H), 7.97 (s, 1H), 7.82 (d, J=8.4 Hz, 1H), 7.83-7.71 (m, 2H), 4.15 (t, J=6.4 Hz, 2H), 3.30-3.16 (m, 4H), 2.68 (t, J=6 Hz, 2H), 1.82-1.76 (m, 2H), 1.73-1.67 (m, 2H).

Calculated (M+H): 456.07, Found (M+1): 456.3.
HPLC purity: 97.16%.

Examples 102-103: The Following Compounds were Prepared by the Method Described Above

| Ex. No. | Structure | Analytical data |
|---|---|---|
| 102 | ![structure] | $^1$H NMR (400 MHz, DMSO-$d_6$) δ (ppm): 8.50 (s, 1H), 7.98 (s, 1H), 7.83 (d, J = 8.4 Hz, 1H), 7.73-7.71 (m, 2H), 5.37-5.18 (m, 1H), 4.17-4.14 (m, 2H), 3.62-3.18 (m, 4H), 2.79-2.68 (m, 2H), 2.13-1.88 (m, 2H). Calculated (M + H): 474.06, Found (M + H): 474.0. HPLC purity: 98.86% |

| Ex. No. | Structure | Analytical data |
|---|---|---|
| 103 | 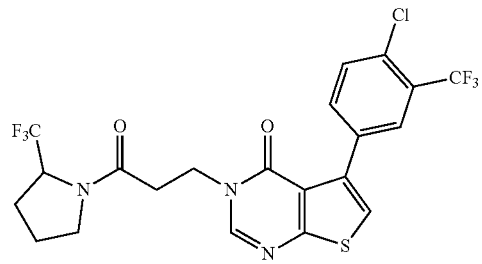 [SMILES: O=C(CCn1cnc2scc(-c3ccc(Cl)c(C(F)(F)F)c3)c2c1=O)N1CCCC1C(F)(F)F] | $^1$H NMR (400 MHz, DMSO-$d_6$) δ (ppm): 8.47 (s, 1H), 7.97 (brs, 1H), 7.83 (d, J = 7.6 Hz, 1H), 7.73-7.71 (m, 2H), 4.69-4.65 (m, 1H), 4.17-4.16 (m, 2H), 3.45-3.43 (m, 2H), 2.87-2.78 (m, 2H), 1.92-1.90 (m, 4H). Calculated (M + H): 524.06, Found (M + H): 524.0. HPLC purity: 97.73% |

Example 104: 5-(4-chlorophenyl)-3-(2-oxo-2-(2-(trifluoromethyl)pyrrolidin-1-yl)ethyl)-2-(trifluoromethyl)thieno[2,3-d]pyrimidin-4(3H)-one

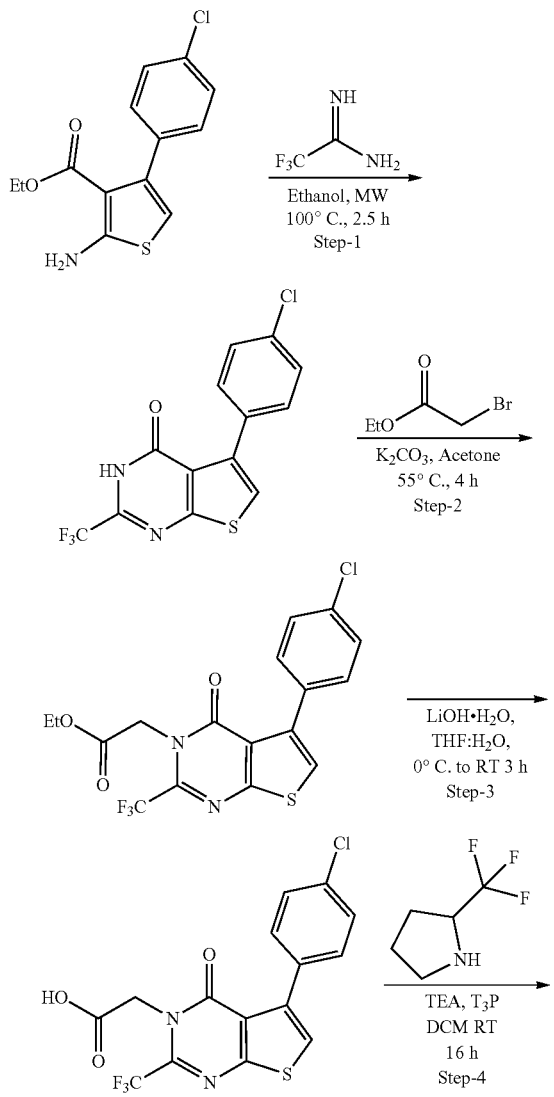

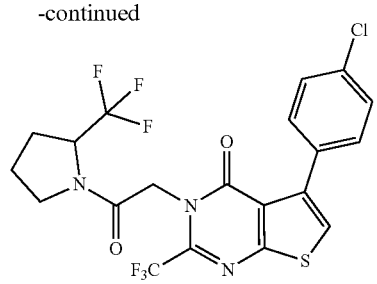

Step 1: 5-(4-chlorophenyl)-2-(trifluoromethyl)thieno[2,3-d]pyrimidin-4(3H)-one To a stirred solution of ethyl 2-amino-4-(4-chlorophenyl)thiophene-3-carboxylate (1.0 g, 3.55 mol) in ethanol (10 mL), was added 2,2,2-trifluoroacetimidamide (3.97 g, 35.49 mol). The resulting mixture was heated under microwave irradiation at 100° C. for 1 h. The progress of the reaction was monitored by TLC, since TLC showed presence of starting material, again 5 eq of 2,2,2-trifluoroacetimidamide was added and the reaction was continued for another 1.5 h. The reaction mixture was cooled to room temperature and the ethanol was evaporated under reduced pressure. The residue was dissolved in ethyl acetate (100 mL), washed water (50 mL), brine (30 mL), dried over anhydrous sodium sulfate, filtered and concentrated under vacuum to afford crude product, which was purified by silica gel column chromatography using 60% ethyl acetate in hexane to afford the title compound 5-(4-chlorophenyl)-2-(trifluoromethyl)thieno[2,3-d]pyrimidin-4(3H)-one (0.8 g, 68% yield) as yellow solid.

Calculated (M+H): 330.98; Found (M+H): 331.2.

Step 2: Ethyl 2-(5-(4-chlorophenyl)-4-oxo-2-(trifluoromethyl)thieno[2,3-d]pyrimidin-3(4H)-yl)acetate To a mixture of 5-(4-chlorophenyl)-2-(trifluoromethyl)thieno[2,3-d]pyrimidin-4(3H)-one (0.4 g, 1.21 mmol) and potassium carbonate (0.5 g, 3.63 mmol) in acetone (50 mL) was added ethyl 2-bromoacetate (0.26 g, 2.42 mmol) at room temperature. The reaction mixture was heated at 55° C. for 4 h. The mixture was allowed to cool to room temperature, filtered and the filtrate was concentrated under reduced pressure to afford crude product, which was purified by silica gel column chromatography using 15% ethyl acetate in hexane to afford the title compound ethyl 2-(5-(4-chlorophenyl)-4-oxo-2-(trifluoromethyl)thieno[2,3-d]pyrimidin-3(4H)-yl)acetate (0.5 g, 98% yield) as colorless semisolid.

Calculated (M+H): 417.02; Found (M+H): 417.0.

Step 3: 2-(5-(4-chlorophenyl)-4-oxo-2-(trifluoromethyl)thieno[2,3-d]pyrimidin-3(4H)-yl)acetic Acid To a suspension of ethyl 2-(5-(4-chlorophenyl)-4-oxo-2-(trifluoromethyl)thieno[2,3-d]pyrimidin-3(4H)-yl)acetate (0.5 g, 1.20 mmol) in tetrahydrofuran:water mixture (10 mL, 1:1) was added lithium hydroxide monohydrate (0.15 g, 3.61 mmol) at 0° C. The resulting suspension was gradually allowed to warm to room temperature and stirred for 3 h. The reaction mixture was cooled to 0° C. and acidified with 1.5M hydrochloric acid solution to pH 2 to 3. The precipitated product was filtered, washed with water and dried to obtain the title compound 2-(5-(4-chlorophenyl)-4-oxo-2-(trifluoromethyl)thieno[2,3-d]pyrimidin-3(4H)-yl)acetic acid (0.4 g, 87% yield) as a colorless solid.

Calculated (M+H): 388.89; Found (M+H): 388.4.

Step 4: 5-(4-chlorophenyl)-3-(2-oxo-2-(2-(trifluoromethyl)pyrrolidin-1-yl)ethyl)-2-(trifluoromethyl)thieno[2,3-d]pyrimidin-4(3H)-one To a solution of 2-(5-(4-chlorophenyl)-4-oxo-2-(trifluoromethyl)thieno[2,3-d]pyrimidin-3(4H)-yl)acetic acid (0.1 g, 0.26 mmol) in dichloromethane (20 mL) was added 2-(trifluoromethyl)pyrrolidine (0.035 g, 0.26 mmol) and triethylamine (0.32 mL, 0.51 mmol) at room temperature. The reaction mixture was cooled to 0° C. and 1-propanephosphonic anhydride (T$_3$P) (0.32 mL, 0.51 mmol, 50% solution in ethyl acetate) was added. Then the reaction mixture was allowed to warm to room temperature and stirred for 16 h. The mixture was diluted with dichloromethane (50 mL), washed with water (2×25 mL), brine solution (25 mL), dried over anhydrous sodium sulfate, filtered and concentrated under vacuum to afford crude product, which was purified by silica gel column chromatography using 30% ethyl acetate in hexane as eluent to afford the title compound 5-(4-chlorophenyl)-3-(2-oxo-2-(2-(trifluoromethyl)pyrrolidin-1-yl)ethyl)-2-(trifluoromethyl)thieno[2,3-d]pyrimidin-4(3H)-one (0.044 g, 34% yield) as a white solid.

$^1$H NMR (400 MHz, DMSO-d$_6$) δ (ppm): 8.10 (s, 1H), 7.66-7.64 (d, J=8.4 Hz, 2H), 7.48-7.46 (d, J=8.4 Hz, 2H), 5.27-5.24 (m, 1H), 5.15-5.11 (m, 1H), 4.68 (brs, 1H), 3.59-3.56 (m, 2H), 2.11-1.89 (m, 4H).

Calculated (M+H): 510.04, Found (M+1): 510.0.

HPLC purity: 99.61%.

Example 105: The Following Compounds were Prepared by the Method Described Above

| Ex. No. | Structure | Analytical data |
|---|---|---|
| 105 | 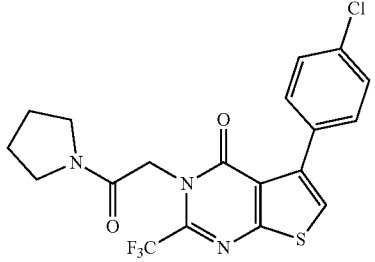 [SMILES: O=C(Cn1c(C(F)(F)F)nc2scc(-c3ccc(Cl)cc3)c2c1=O)N1CCCC1] | $^1$H NMR (400 MHz, DMSO-d$_6$) δ (ppm): 8.08 (s, 1H), 7.66 (d, J = 8.0 Hz, 2H), 7.47 (d, J = 8.4 Hz, 2H), 5.09 (s, 2H), 3.88 (t, J = 6.8 Hz, 2H), 3.26 (m, 2H), 1.90-1.83 (m, 2H), 1.77-1.71 (m, 2H). Calculated (M + H): 442.05, Found (M + H): 442.1. HPLC purity: 99.97% |

Biological Example

HEK293 cells with constructs conferring stable expression of the GRIN1 gene and tetracycline-inducible expression of the GRIN2B gene (Chantest, Cleveland, Ohio) are grown to ~75% confluence in tissue culture flasks at 37° C., 5% CO$_2$. NR2B expression is induced by overnight incubation with 0.3-0.4 μg/ml tetracycline in the presence of 2.5 mM ARL-15896 at 37° C., followed by moving to 30° C. for 3-5 hours. Cells are next harvested using TripleExpress™ (Life Technologies, Carlsbad, Calif.) according to the manufacturer's instructions, first removing culture medium, rinsing with Dulbecco's phosphate buffered saline (Ca$^{2+}$ and Mg$^{2+}$-free), and then adding the TripleExpress™ reagent. Harvested cells are spun down, washed twice in Ca$^{2+}$- and Mg$^{2+}$-free Hank's Balanced Salt Solution with 20 mM HEPES and 10 mM glucose, pH 7.4 (HHnoCa solution), and counted with viability assessed using Trypan Blue. Cells are loaded with fluo-8 Ca$^{2+}$-sensitive dye in HHnoCa solution according to the manufacturer's directions (AAT Bioquest, Sunnyvale, Calif.), incubating at 37° C. for 20 minutes followed by 25 minutes at 22-25° C. After a wash in HHnoCa to remove extracellular dye, cells are resuspended in HHnoCa and plated at 2×10$^7$-3×10$^7$ cells per well in a volume of 25 μl/well in 384 well black-wall, clear bottom plates (Hamamatsu, Middlesex, N.J.). Plates are then centrifuged to create a monolayer in the wells and stored in the dark until used.

Prior to analysis, compound plates are prepared with each compound at 6× the final desired concentration. From stock solutions at 10 mM in 100% DMSO, compounds are spotted in the desired amounts using an ECHO liquid handler (Labcyte, Sunnyvale, Calif.) into wells of a 384-well plate and then diluted with 50 μl of HHnoCa containing 750 nM Ro 25-6981 and 120 μM 5,7-dichlorokynurenic acid (both purchased from Tocris Bioscience (Bristol, England) and maintained as 10 mM stock solutions in 100% DMSO). To insure complete compound dissolution, these plates are then placed in an orbital shaker for at least one hour. Also prepared prior to the assay is a co-agonist plate containing HHnoCa with 240 μM glutamate, 2.4 mM glycine, and 7.2 mM CaCl$_2$, which is 2.4× the desired final concentration of each reagent. Both the compound plate and co-agonist plate are 384-well polypropylene plates from Thermo Fisher Scientific, Waltham, Mass.

The assay is performed by first adding 10 μl solution from each well of the compound plate described above to the cell plate using a CyBiWell liquid handler (Analytik Jena AG, Jena, Germany), followed by 10 minutes pre-incubation in the dark. Cell plates are then loaded onto a Hamamatsu FDSS 6000 plate reader. After a 30-second baseline, 25 μl is added to each well from the co-agonist plate, and the fluorescence signal is recorded for another 2 minutes. FDSS software applies shading and autofluorescence correction, and resultant raw fluorescence measurements are exported in the form of a fluorescence ratio for each well to its own reading at time zero in the experiment. In each plate, negative control wells consist of wells where Ro 25-6981 and 5,7 dichlorokynurenic acid are present and co-agonist is applied in the absence of any added assay compound. Under these conditions, the Ca$^{2+}$ response to co-agonist is suppressed. Positive control wells also present in each plate contain 5,7 dichlorokynurenic acid but no Ro 25-6981, so that co-agonist addition results in a large Ca$^{2+}$ response. Compounds tested are evaluated on the basis of their ability to reverse the suppression of the Ca$^{2+}$ response mediated by Ro 25-6981, which is quantified as % reversal=100*(R−R$_{neg}$)/(R$_{pos}$−R$_{neg}$) where R is the fluorescence ratio for the test compound at the end of the experiment and R$_{neg}$ and R$_{pos}$ are the end ratios for the negative and positive controls, respectively. Using this equation, a compound would return 0% if it had no effect on the Ro 25-6981-mediated suppression of Ca$^{2+}$ flux, whereas a compound that entirely reversed the effect of Ro 25-6981 (to the level of co-agonist stimulation) would return 100%.

The results of the above assay are shown in Table 1.

TABLE 1

| Ex. No. | Compound Name | Response Recovered (%) |
|---|---|---|
| 70 | 5-[6-chloro-5-(trifluoromethyl)pyridin-3-yl]-3-[2-(3-fluoropyrrolidin-1-yl)-2-oxoethyl]-3H,4H-thieno[2,3-d]pyrimidin-4-one | 22 |
| 69 | 5-(3,4-dichlorophenyl)-3-{2-[(3S)-3-fluoropyrrolidin-1-yl]-2-oxoethyl}-3H,4H-thieno[2,3-d]pyrimidin-4-one | 94 |
| 68 | 5-(3,4-dichlorophenyl)-3-{2-[(3R)-3-fluoropyrrolidin-1-yl]-2-oxoethyl}-3H,4H-thieno[2,3-d]pyrimidin-4-one | 71 |
| 67 | 5-(3,4-dichlorophenyl)-3-{2-[(3R,4S)-3,4-difluoropyrrolidin-1-yl]-2-oxoethyl}-3H,4H-thieno[2,3-d]pyrimidin-4-one | 84 |
| 66 | 5-[4-chloro-3-(trifluoromethyl)phenyl]-3-{2-[(3R,4S)-3,4-difluoropyrrolidin-1-yl]-2-oxoethyl}-3H,4H-thieno[2,3-d]pyrimidin-4-one | 103 |
| 65 | 5-[4-chloro-3-(trifluoromethyl)phenyl]-3-{2-[(3S)-3-fluoropyrrolidin-1-yl]-2-oxoethyl}-3H,4H-thieno[2,3-d]pyrimidin-4-one | 87 |
| 64 | 5-[4-chloro-3-(trifluoromethyl)phenyl]-3-{2-[(3R)-3-fluoropyrrolidin-1-yl]-2-oxoethyl}-3H,4H-thieno[2,3-d]pyrimidin-4-one | 117 |
| 63 | 5-(5,6-dichloropyridin-3-yl)-3-[2-(3-fluoropyrrolidin-1-yl)-2-oxoethyl]-3H,4H-thieno[2,3-d]pyrimidin-4-one | 10 |
| 62 | 5-[3-chloro-4-(trifluoromethyl)phenyl]-3-[2-(3-fluoropyrrolidin-1-yl)-2-oxoethyl]-3H,4H-thieno[2,3-d]pyrimidin-4-one | 62 |
| 61 | 5-[4-fluoro-3-(trifluoromethyl)phenyl]-3-[2-(3-fluoropyrrolidin-1-yl)-2-oxoethyl]-3H,4H-thieno[2,3-d]pyrimidin-4-one | 83 |
| 60 | 5-(3,4-dichlorophenyl)-3-[2-(3-fluoropyrrolidin-1-yl)-2-oxoethyl]-3H,4H-thieno[2,3-d]pyrimidin-4-one | 98 |
| 59 | 5-(4-chloro-3-fluorophenyl)-3-[2-(3-fluoropyrrolidin-1-yl)-2-oxoethyl]-3H,4H-thieno[2,3-d]pyrimidin-4-one | 43 |
| 88 | 5-(3-chloro-4-fluorophenyl)-4-oxo-3H,4H-thieno[2,3-d]pyrimidin-3-yl 3-fluoropyrrolidine-1-carboxylate | 83 |
| 94 | 5-[4-chloro-3-(trifluoromethyl)phenyl]-3-[(E)-(pyrrolidin-1-ylmetbylidene)amino]-3H,4H-thieno[2,3-d]pyrimidin-4-one | 18 |
| 95 | N-{5-[4-chloro-3-(trifluoromethyl)phenyl]-4-oxo-3H,4H-thieno[2,3-d]pyrimidin-3-yl}cyclopentanecarboxamide | 21 |
| 87 | 5-(4-chloro-3-fluorophenyl)-4-oxo-3H,4H-thieno[2,3-d]pyrimidin-3-yl pyrrolidine-1-carboxylate | 32 |
| 103 | 5-[4-chloro-3-(trifluoromethyl)phenyl]-3-{3-oxo-3-[2-(trifluoromethyl)pyrrolidin-1-yl]propyl}-3H,4H-thieno[2,3-d]pyrimidin-4-one | −2 |
| 96 | N-[5-(3-chloro-4-fluorophenyl)-4-oxo-3H,4H-thieno[2,3-d]pyrimidin-3-yl]cyclopentanecarboxamide | 27 |
| 58 | 5-(3-chloro-4-fluorophenyl)-3-[2-(3-fluoropyrrolidin-1-yl)-2-oxoethyl]-3H,4H-thieno[2,3-d]pyrimidin-4-one | 65 |
| 100 | (E)-N'-{5-[4-chloro-3-(trifluoromethyl)phenyl]-4-oxo-3H,4H-thieno[2,3-d]pyrimidin-3-yl}-N,N-dimethylmethanimidamide | 14 |
| 93 | 5-(3-chloro-4-fluorophenyl)-3-[2-oxo-2-(pyrrolidin-1-yl)ethoxy]-3H,4H-thieno[2,3-d]pyrimidin-4-one | −1 |
| 102 | 5-[4-chloro-3-(trifluoromethyl)phenyl]-3-[3-(3-fluoropyrrolidin-1-yl)-3-oxopropyl]-3H,4H-thieno[2,3-d]pyrimidin-4-one | 2 |
| 101 | 5-[4-chloro-3-(trifluoromethyl)phenyl]-3-[3-oxo-3-(pyrrolidin-1-yl)propyl]-3H,4H-thieno[2,3-d]pyrimidin-4-one | 6 |
| 90 | N-[5-(3-chloro-4-fluorophenyl)-4-oxo-3H,4H-thieno[2,3-d]pyrimidin-3-yl]pyrrolidine-1-carboxamide | 10 |
| 57 | 5-(3-chloro-4-fluorophenyl)-3-[1-oxo-1-(pyrrolidin-1-yl)propan-2-yl]-3H,4H-thieno[2,3-d]pyrimidin-4-one | 3 |

TABLE 1-continued

| Ex. No. | Compound Name | Response Recovered (%) |
|---|---|---|
| 86 | 5-(3-chloro-4-fluorophenyl)-4-oxo-3H,4H-thieno[2,3-d]pyrimidin-3-yl pyrrolidine-1-carboxylate | 48 |
| 92 | 5-[4-chloro-3-(trifluoromethyl)phenyl]-3-[2-oxo-2-(pyrrolidin-1-yl)ethoxy]-3H,4H-thieno[2,3-d]pyrimidin-4-one | 37 |
| 85 | 5-[4-chloro-3-(trifluoromethyl)phenyl]-4-oxo-3H,4H-thieno[2,3-d]pyrimidin-3-yl pyrrolidine-1-carboxylate | 51 |
| 91 | 5-[4-chloro-3-(trifluoromethyl)phenyl]-3-{[2-oxo-2-(pyrrolidin-1-yl)ethyl]amino}-3H,4H-thieno[2,3-d]pyrimidin-4-one | 2 |
| 89 | N-{5-[4-chloro-3-(trifluoromethyl)phenyl]-4-oxo-3H,4H-thieno[2,3-d]pyrimidin-3-yl}pyrrolidine-1-carboxamide | 29 |
| 56 | 5-[4-chloro-3-(trifluoromethyl)phenyl]-3-[1-oxo-1-(pyrrolidin-1-yl)propan-2-yl]-3H,4H-thieno[2,3-d]pyrimidin-4-one | 0 |
| 19 | 5-[4-chloro-3-(trifluoromethyl)phenyl]-3-[2-(3-fluoropyrrolidin-1-yl)-2-oxoethyl]-3H,4H-thieno[2,3-d]pyrimidin-4-one | 93 |
| 55 | 3-[2-oxo-2-(pyrrolidin-1-yl)ethyl]-5-[3-(trifluoromethyl)phenyl]-3H,4H-thieno[2,3-d]pyrimidin-4-one | 33 |
| 54 | 5-[2-fluoro-5-(trifluoromethyl)phenyl]-3-[2-oxo-2-(pyrrolidin-1-yl)ethyl]-3H,4H-thieno[2,3-d]pyrimidin-4-one | 20 |
| 53 | 5-(2-chloro-4-fluorophenyl)-3-[2-oxo-2-(pyrrolidin-1-yl)ethyl]-3H,4H-thieno[2,3-d]pyrimidin-4-one | 5 |
| 84 | 5-(3,4-dichlorophenyl)-6-methyl-3-[2-oxo-2-(pyrrolidin-1-yl)ethyl]-3H,4H-thieno[2,3-d]pyrimidin-4-one | 60 |
| 83 | 5-(3-chloro-4-fluorophenyl)-6-methyl-3-[2-oxo-2-(pyrrolidin-1-yl)ethyl]-3H,4H-thieno[2,3-d]pyrimidin-4-one | 45 |
| 52 | 5-(2-chlorophenyl)-3-[2-oxo-2-(pyrrolidin-1-yl)ethyl]-3H,4H-thieno[2,3-d]pyrimidin-4-one | 4 |
| 51 | 3-[2-oxo-2-(pyrrolidin-1-yl)ethyl]-5-[3-(trifluoromethoxy)phenyl]-3H,4H-thieno[2,3-d]pyrimidin-4-one | 27 |
| 50 | 5-[2-methyl-4-(trifluoromethyl)phenyl]-3-[2-oxo-2-(pyrrolidin-1-yl)ethyl]-3H,4H-thieno[2,3-d]pyrimidin-4-one | 9 |
| 82 | 5-[4-chloro-3-(trifluoromethyl)phenyl]-6-methyl-3-[2-oxo-2-(pyrrolidin-1-yl)ethyl]-3H,4H-thieno[2,3-d]pyrimidin-4-one | 15 |
| 49 | 5-[4-(dimethylamino)phenyl]-3-[2-oxo-2-(pyrrolidin-1-yl)ethyl]-3H,4H-thieno[2,3-d]pyrimidin-4-one | 0 |
| 81 | 5-[4-fluoro-3-(trifluoromethyl)phenyl]-6-methyl-3-[2-oxo-2-(pyrrolidin-1-yl)ethyl]-3H,4H-thieno[2,3-d]pyrimidin-4-one | 40 |
| 48 | 5-[3,5-bis(trifluoromethyl)phenyl]-3-[2-oxo-2-(pyrrolidin-1-yl)ethyl]-3H,4H-thieno[2,3-d]pyrimidin-4-one | −1 |
| 47 | 5-[4-fluoro-3-(trifluoromethyl)phenyl]-3-[2-oxo-2-(pyrrolidin-1-yl)ethyl]-3H,4H-thieno[2,3-d]pyrimidin-4-one | 43 |
| 46 | 3-[2-oxo-2-(pyrrolidin-1-yl)ethyl]-5-[2-(trifluoromethyl)pyridin-4-yl]-3H,4H-thieno[2,3-d]pyrimidin-4-one | −1 |
| 45 | 5-(2,3-dichlorophenyl)-3-[2-oxo-2-(pyrrolidin-1-yl)ethyl]-3H,4H-thieno[2,3-d]pyrimidin-4-one | 7 |
| 44 | 5-[2-methoxy-5-(trifluoromethyl)phenyl]-3-[2-oxo-2-(pyrrolidin-1-yl)ethyl]-3H,4H-thieno[2,3-d]pyrimidin-4-one | 4 |
| 97 | ethyl 2-[5-(4-chlorophenyl)-2-methyl-4-oxo-3H,4H-thieno[2,3-d]pyrimidin-3-yl]acetate | 2 |
| 98 | 5-(4-chlorophenyl)-2-methyl-3-[2-oxo-2-(pyrrolidin-1-yl)ethyl]-3H,4H-thieno[2,3-d]pyrimidin-4-one | 6 |
| 99 | 5-(4-chlorophenyl)-2-methyl-3-{oxo-2-[2-(trifluoromethyl)pyrrolidin-1-yl]ethyl}-3H,4H-thieno[2,3-d]pyrimidin-4-one | 3 |
| 43 | 5-[2-chloro-4-(trifluoromethyl)phenyl]-3-[2-oxo-2-(pyrrolidin-1-yl)ethyl]-3H,4H-thieno[2,3-d]pyrimidin-4-one | 8 |
| 104 | 5-(4-chlorophenyl)-3-{2-oxo-2-[2-(trifluoromethyl)pyrrolidin-1-yl]ethyl}-2-(trifluoromethyl)-3H,4H-thieno[2,3-d]pyrimidin-4-one | −2 |
| 42 | 5-(3,4-difluorophenyl)-3-[2-oxo-2-(pyrrolidin-1-yl)ethyl]-3H,4H-thieno[2,3-d]pyrimidin-4-one | 3 |
| 41 | 5-(4-methoxyphenyl)-3-[2-oxo-2-(pyrrolidin-1-yl)ethyl]-3H,4H-thieno[2,3-d]pyrimidin-4-one | 5 |
| 40 | 3-[2-oxo-2-(pyrrolidin-1-yl)ethyl]-5-(pyrimidin-5-yl)-3H,4H-thieno[2,3-d]pyrimidin-4-one | 1 |
| 80 | 5-(4-chlorophenyl)-6-methyl-3-{2-oxo-2-[2-(trifluoromethyl)pyrrolidin-1-yl]ethyl}-3H,4H-thieno[2,3-d]pyrimidin-4-one | 10 |
| 105 | 5-(4-chlorophenyl)-3-[2-oxo-2-(pyrrolidin-1-yl)ethyl]-2-(trifluoromethyl)-3H,4H-thieno[2,3-d]pyrimidin-4-one | −1 |
| 39 | 5-(5-fluoropyridin-3-yl)-3-[2-oxo-2-(pyrrolidin-1-yl)ethyl]-3H,4H-thieno[2,3-d]pyrimidin-4-one | 3 |
| 38 | 5-[2-fluoro-4-(trifluoromethyl)phenyl]-3-[2-oxo-2-(pyrrolidin-1-yl)ethyl]-3H,4H-thieno[2,3-d]pyrimidin-4-one | 10 |
| 37 | 5-(3,4-dichlorophenyl)-3-[2-oxo-2-(pyrrolidin-1-yl)ethyl]-3H,4H-thieno[2,3-d]pyrimidin-4-one | 61 |
| 36 | 5-(6-methoxypyridin-3-yl)-3-[2-oxo-2-(pyrrolidin-1-yl)ethyl]-3H,4H-thieno[2,3-d]pyrimidin-4-one | 2 |

TABLE 1-continued

| Ex. No. | Compound Name | Response Recovered (%) |
|---|---|---|
| 79 | 5-(4-chlorophenyl)-6-methyl-3-[2-oxo-2-(pyrrolidin-1-yl)ethyl]-3H,4H-thieno[2,3-d]pyrimidin-4-one | 17 |
| 20 | 5-[4-chloro-3-(trifluoromethyl)phenyl]-3-[2-oxo-2-(pyrrolidin-1-yl)ethyl]-3H,4H-thieno[2,3-d]pyrimidin-4-one | 76 |
| 35 | 5-(4-tert-butylphenyl)-3-[2-oxo-2-(pyrrolidin-1-yl)ethyl]-3H,4H-thieno[2,3-d]pyrimidin-4-one | 14 |
| 34 | 3-[2-oxo-2-(pyrrolidin-1-yl)ethyl]-5-[4-(trifluoromethoxy)phenyl]-3H,4H-thieno[2,3-d]pyrimidin-4-one | 16 |
| 33 | 5-(1-methyl-1H-pyrazol-5-yl)-3-[2-oxo-2-(pyrrolidin-1-yl)ethyl]-3H,4H-thieno[2,3-d]pyrimidin-4-one | 1 |
| 32 | 4-{4-oxo-3-[2-oxo-2-(pyrrolidin-1-yl)ethyl]-3H,4H-thieno[2,3-d]pyrimidin-5-yl}benzonitrile | 2 |
| 31 | 5-(3-fluorophenyl)-3-[2-oxo-2-(pyrrolidin-1-yl)ethyl]-3H,4H-thieno[2,3-d]pyrimidin-4-one | 3 |
| 30 | 5-(3-chloro-4-fluorophenyl)-3-[2-oxo-2-(pyrrolidin-1-yl)ethyl]-3H,4H-thieno[2,3-d]pyrimidin-4-one | 41 |
| 29 | 3-[2-oxo-2-(pyrrolidin-1-yl)ethyl]-5-(pyridin-4-yl)-3H,4H-thieno[2,3-d]pyrimidin-4-one | 2 |
| 21 | 5-(4-chloro-3-fluorophenyl)-3-[2-oxo-2-(pyrrolidin-1-yl)ethyl]-3H,4H-thieno[2,3-d]pyrimidin-4-one | 19 |
| 28 | 5-(4-methylphenyl)-3-{2-oxo-2-[2-(trifluoromethyl)pyrrolidin-1-yl]ethyl}-3H,4H-thieno[2,3-d]pyrimidin-4-one | 6 |
| 27 | 5-(4-fluorophenyl)-3-{2-oxo-2-[2-(trifluoromethyl)pyrrolidin-1-yl]ethyl}-3H,4H-thieno[2,3-d]pyrimidin-4-one | 7 |
| 18 | 3-{2-oxo-2-[2-(trifluoromethyl)pyrrolidin-1-yl]ethyl}-5-[4-(trifluoromethyl)phenyl]-3H,4H-thieno[2,3-d]pyrimidin-4-one | 8 |
| 26 | 3-[2-oxo-2-(piperidin-1-yl)ethyl]-5-[4-(trifluoromethyl)phenyl]-3H,4H-thieno[2,3-d]pyrimidin-4-one | 1 |
| 25 | 5-(4-methylphenyl)-3-[2-oxo-2-(pyrrolidin-1-yl)ethyl]-3H,4H-thieno[2,3-d]pyrimidin-4-one | 5 |
| 24 | 5-(4-fluorophenyl)-3-[2-oxo-2-(piperidin-1-yl)ethyl]-3H,4H-thieno[2,3-d]pyrimidin-4-one | 4 |
| 29 | 5-(4-fluorophenyl)-3-[2-oxo-2-(pyrrolidin-1-yl)ethyl]-3H,4H-thieno[2,3-d]pyrimidin-4-one | 3 |
| 78 | 6-(4-chlorophenyl)-3-[2-(4,4-difluoropiperidin-1-yl)-2-oxoethyl]-3H,4H-thieno[2,3-d]pyrimidin-4-one | 13 |
| 77 | 6-(4-chlorophenyl)-3-[2-(morpholin-4-yl)-2-oxoethyl]-3H,4H-thieno[2,3-d]pyrimidin-4-one | 18 |
| 25 | 5-(4-methylphenyl)-3-[2-oxo-2-(piperidin-1-yl)ethyl]-3H,4H-thieno[2,3-d]pyrimidin-4-one | 1 |
| 17 | 3-[2-oxo-2-(pyrrolidin-1-yl)ethyl]-5-[4-(trifluoromethyl)phenyl]-3H,4H-thieno[2,3-d]pyrimidin-4-one | 11 |
| 76 | 2-[6-(4-chlorophenyl)-4-oxo-3H,4H-thieno[2,3-d]pyrimidin-3-yl]-N-cyclopropylacetamide | 34 |
| 75 | 6-(4-chlorophenyl)-3-[2-oxo-2-(piperidin-1-yl)ethyl]-3H,4H-thieno[2,3-d]pyrimidin-4-one | 0 |
| 16 | 5-(4-chlorophenyl)-3-[2-(3-fluoropyrrolidin-1-yl)-2-oxoethyl]-3H,4H-thieno[2,3-d]pyrimidin-4-one | 21 |
| 74 | 6-(4-chlorophenyl)-3-[2-oxo-2-(pyrrolidin-1-yl)ethyl]-3H,4H-thieno[2,3-d]pyrimidin-4-one | 1 |
| 15 | 5-(4-chlorophenyl)-3-[2-(4-hydroxy-4-phenylpiperidin-1-yl)-2-oxoethyl]-3H,4H-thieno[2,3-d]pyrimidin-4-one | −1 |
| 14 | 5-(4-chlorophenyl)-3-[2-(4,4-difluoropiperidin-1-yl)-2-oxoethyl]-3H,4H-thieno[2,3-d]pyrimidin-4-one | 2 |
| 13 | 2-[5-(4-chlorophenyl)-4-oxo-3H,4H-thieno[2,3-d]pyrimidin-3-yl]-N,N-diethylacetamide | 5 |
| 12 | 5-(4-chlorophenyl)-3-[2-(2,6-dimethylpiperidin-1-yl)-2-oxoethyl]-3H,4H-thieno[2,3-d]pyrimidin-4-one | −1 |
| 11 | 5-(4-chlorophenyl)-3-{2-oxo-2-[2-(trifluoromethyl)pyrrolidin-1-yl]ethyl}-3H,4H-thieno[2,3-d]pyrimidin-4-one | 8 |
| 10 | 5-(4-chlorophenyl)-3-{2-[(2S)-2-methylpyrrolidin-1-yl]-2-oxoethyl}-3H,4H-thieno[2,3-d]pyrimidin-4-one | 2 |
| 9 | 2-[5-(4-chlorophenyl)-4-oxo-3H,4H-thieno[2,3-d]pyrimidin-3-yl]-N-cyclobutylacetamide | 3 |
| 8 | 5-(4-chlorophenyl)-3-[2-oxo-2-(piperidin-1-yl)ethyl]-3H,4H-thieno[2,3-d]pyrimidin-4-one | 3 |
| 7 | 2-[5-(4-chlorophenyl)-4-oxo-3H,4H-thieno[2,3-d]pyrimidin-3-yl]-N-(1-methylpyrrolidin-3-yl)acetamide | 3 |
| 6 | 5-(4-chlorophenyl)-3-[2-(3-hydroxypyrrolidin-1-yl)-2-oxoethyl]-3H,4H-thieno[2,3-d]pyrimidin-4-one | 3 |
| 5 | 2-[5-(4-chlorophenyl)-4-oxo-3H,4H-thieno[2,3-d]pyrimidin-3-yl]-N-cyclopropylacetamide | 2 |
| 4 | 5-(4-chlorophenyl)-3-[2-(morpholin-4-yl)-2-oxoethyl]-3H,4H-thieno[2,3-d]pyrimidin-4-one | 3 |
| 3 | 5-(4-chlorophenyl)-3-[2-(4-methylpiperazin-1-yl)-2-oxoethyl]-3H,4H-thieno[2,3-d]pyrimidin-4-one | 3 |

TABLE 1-continued

| Ex. No. | Compound Name | Response Recovered (%) |
|---|---|---|
| 2 | 5-(4-chlorophenyl)-3-[2-(4-fluoropiperidin-1-yl)-2-oxoethyl]-3H,4H-thieno[2,3-d]pyrimidin-4-one | 25 |
| 1 | 5-(4-chlorophenyl)-3-[2-(4-hydroxypiperidin-1-yl)-2-oxoethyl]-3H,4H-thieno[2,3-d]pyrimidin-4-one | 0 |
| 73 | 5-(5-chloro-6-fluoropyridin-3-yl)-3-[2-(3,4-difluoropyrrolidin-1-yl)-2-oxoethyl]-3H,4H-thieno[2,3-d]pyrimidin-4-one | 11 |
| 72 | 5-(5,6-dichloropyridin-3-yl)-3-[2-(3,4-difluoropyrrolidin-1-yl)-2-oxoethyl]-3H,4H-thieno[2,3-d]pyrimidin-4-one | 15 |
| 71 | 5-[6-chloro-5-(trifluoromethyl)pyridin-3-yl]-3-[2-(3,4-difluoropyrrolidin-1-yl)-2-oxoethyl]-3H,4H-thieno[2,3-d]pyrimidin-4-one | 25 |

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A method of treating Alzheimer's disease in a patient in need thereof, comprising administering to the patient an effective amount of a compound represented by Formula I:

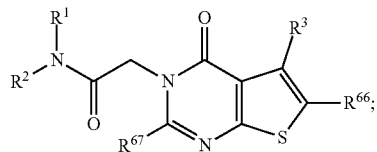

Formula I or a pharmaceutically acceptable salt, stereoisomer or prodrug thereof, wherein:
$R^1$ and $R^2$, together with the nitrogen to which they are attached, form a 4-6 membered heterocyclic ring substituted on a carbon not adjacent to the nitrogen b one, two or more substituents each independently selected from the group consisting of halogen, cyano, oxo, hydroxyl and $C_{1-6}$alkyl (optionally substituted by one, two or three halogens);

$R^3$ is selected from the group consisting of phenyl, naphthyl, heteroaryl, heterocyclyl and $C_{3-6}$cycloalkyl; wherein $R^3$ may optionally be substituted with one, two or three substituents each independently selected from $C_{1-4}$alkyl, halogen, hydroxyl, cyano, $C_{1-4}$alkoxy, $C_{2-6}$alkenyl, $C_{2-6}$alkynyl, $C_{3-6}$cycloalkyl, $C_{1-6}$alkyl-S(O)$_2$—, $C_{1-6}$alkylcarbonyl, $R^aR^bN$—SO$_2$—, $NR^aR^b$, C(O)OH, $C_{1-4}$alkoxycarbonyl, and $NR^aR^b$carbonyl; and wherein $C_{1-4}$alkyl, $C_{1-4}$alkoxy, $C_{2-6}$alkenyl, $C_{2-6}$alkynyl, $C_{3-6}$cycloalkyl, $C_{1-6}$alkyl-S(O)$_2$—, and $C_{1-6}$alkylcarbonyl may be optionally substituted by one or more substituents each independently selected from halogen, hydroxyl, cyano, and $NR^aR^b$;

$R^{66}$ and $R^{67}$ are each independently selected from the group consisting of hydrogen, halogen, $C_{1-4}$alkyl (optionally substituted by one, two, three substituents selected from halogen hydroxyl, cyano and $NR^aR^b$), and phenyl (optionally substituted by one, two or three halogens); and $R^a$ and $R^b$ are independently selected, for each occurrence, from the group consisting of hydrogen, hydroxyl, and $C_{1-3}$alkyl; or $R^a$ and $R^b$ together with the nitrogen to which they are attached, form a 4-6 membered heterocyclic ring which may have an additional heteroatom selected from O, S, or N.

2. The method of claim 1, wherein $R^3$ is selected from the group consisting of phenyl and heteroaryl; wherein $R^3$ is optionally substituted with one, two or three substituents each independently selected from the group consisting of $C_{1-4}$alkyl, halogen, hydroxyl, cyano, $C_{1-4}$alkoxy, $C_{2-6}$alkenyl, $C_{2-6}$alkynyl, $C_{3-6}$cycloalkyl, $C_{1-6}$alkyl-S(O)$_2$—, $C_{1-6}$alkylcarbonyl, $R^aR^bN$—SO$_2$—, $NR^aR^b$, C(O)OH, $C_{1-4}$alkoxycarbonyl, and $NR^aR^b$carbonyl; wherein $C_{1-4}$alkyl, $C_{1-4}$alkoxy, $C_{2-6}$alkenyl, $C_{2-6}$alkynyl, $C_{3-6}$cycloalkyl, $C_{1-6}$alkyl-S(O)$_2$—, and $C_{1-6}$alkylcarbonyl may be optionally substituted by one or more substituents each independently selected from halogen, hydroxyl, cyano, and $NR^aR^b$.

3. The method of claim 1, wherein the compound is represented by the structure:

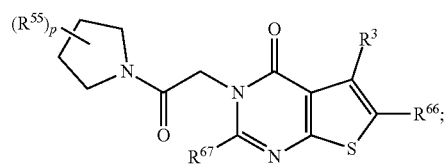

wherein
R⁵⁵ is selected from the group consisting of hydroxyl, fluorine, methyl, CF₃, phenyl and hydroxyl; and wherein p is 0, 1 or 2.

4. The method of claim 1, wherein the compound is represented by the structure:

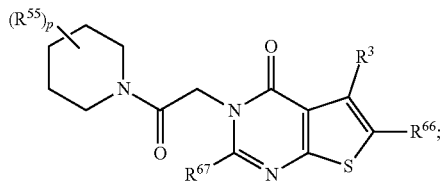

wherein
R⁵⁵ is selected from the group consisting of hydroxyl, fluorine, methyl, CF₃, phenyl and hydroxyl; and wherein p is 0, 1 or 2.

5. The method of claim 1, wherein R³ is phenyl, pyrimidinyl or pyridinyl, each optionally substituted by one or two substituents each independently selected from halogen and C₁₋₃alkyl (optionally substituted by one, two or three halogens).

6. The method of claim 1, wherein the compound is represented by the structure:

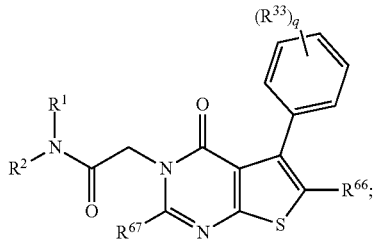

wherein
R³³ is selected from the group consisting of fluorine, chlorine, CF₃ and methyl; and wherein q is 0, 1, 2 or 3.

7. A method of treating Alzheimer's disease in a patient in need thereof, comprising administering to the patient an effective amount of a compound selected from the group consisting of: 5-[6-chloro-5-(trifluoromethyl)pyridin-3-yl]-3-[2-(3-fluoropyrrolidin-1-yl)-2-oxoethyl]-3H,4H-thieno[2,3-d]pyrimidin-4-one; 5-(3,4-dichlorophenyl)-3-{2-[(3S)-3-fluoropyrrolidin-1-yl]-2-oxoethyl}-3H,4H-thieno[2,3-d]pyrimidin-4-one; 5-(3,4-dichlorophenyl)-3-{2-[(3R)-3-fluoropyrrolidin-1-yl]-2-oxoethyl}-3H,4H-thieno[2,3-d]pyrimidin-4-one; 5-(3,4-dichlorophenyl)-3-{2-[(3R,4S)-3,4-difluoropyrrolidin-1-yl]-2-oxoethyl}-3H,4H-thieno[2,3-d]pyrimidin-4-one; 5-[4-chloro-3-(trifluoromethyl)phenyl]-3-{2-[(3R,4S)-3,4-difluoropyrrolidin-1-yl]-2-oxoethyl}-3H,4H-thieno[2,3-d]pyrimidin-4-one; 5-[4-chloro-3-(trifluoromethyl)phenyl]-3-{2-[(3S)-3-fluoropyrrolidin-1-yl]-2-oxoethyl}-3H,4H-thieno[2,3-d]pyrimidin-4-one; 5-[4-chloro-3-(trifluoromethyl)phenyl]-3-{2-[(3R)-3-fluoropyrrolidin-1-yl]-2-oxoethyl}-3H,4H-thieno[2,3-d]pyrimidin-4-one; 5-(5,6-dichloropyridin-3-yl)-3-[2-(3-fluoropyrrolidin-1-yl)-2-oxoethyl]-3H,4H-thieno[2,3-d]pyrimidin-4-one; 5-[3-chloro-4-(trifluoromethyl)phenyl]-3-[2-(3-fluoropyrrolidin-1-yl)-2-oxoethyl]-3H,4H-thieno[2,3-d]pyrimidin-4-one; 5-[4-fluoro-3-(trifluoromethyl)phenyl]-3-[2-(3-fluoropyrrolidin-1-yl)-2-oxoethyl]-3H,4H-thieno[2,3-d]pyrimidin-4-one; 5-(3,4-dichlorophenyl)-3-[2-(3-fluoropyrrolidin-1-yl)-2-oxoethyl]-3H,4H-thieno[2,3-d]pyrimidin-4-one; 5-(4-chloro-3-fluorophenyl)-3-[2-(3-fluoropyrrolidin-1-yl)-2-oxoethyl]-3H,4H-thieno[2,3-d]pyrimidin-4-one; 5-(3-chloro-4-fluorophenyl)-4-oxo-3H,4H-thieno[2,3-d]pyrimidin-3-yl 3-fluoropyrrolidine-1-carboxylate; 5-[4-chloro-3-(trifluoromethyl)phenyl]-3-[(E)-(pyrrolidin-1-ylmethylidene)amino]-3H,4H-thieno[2,3-d]pyrimidin-4-one; N-{5-[4-chloro-3-(trifluoromethyl)phenyl]-4-oxo-3H,4H-thieno[2,3-d]pyrimidin-3-yl}cyclopentanecarboxamide; 5-(4-chloro-3-fluorophenyl)-4-oxo-3H,4H-thieno[2,3-d]pyrimidin-3-yl pyrrolidine-1-carboxylate; 5-[4-chloro-3-(trifluoromethyl)phenyl]-3-{3-oxo-3-[2-(trifluoromethyl)pyrrolidin-1-yl]propyl}-3H,4H-thieno[2,3-d]pyrimidin-4-one; N-[5-(3-chloro-4-fluorophenyl)-4-oxo-3H,4H-thieno[2,3-d]pyrimidin-3-yl]cyclopentanecarboxamide; 5-(3-chloro-4-fluorophenyl)-3-[2-(3-fluoropyrrolidin-1-yl)-2-oxoethyl]-3H,4H-thieno[2,3-d]pyrimidin-4-one; (E)-N'-{5-[4-chloro-3-(trifluoromethyl)phenyl]-4-oxo-3H,4H-thieno[2,3-d]pyrimidin-3-yl}-N,N-dimethylmethanimidamide; 5-(3-chloro-4-fluorophenyl)-3-[2-oxo-2-(pyrrolidin-1-yl)ethoxy]-3H,4H-thieno[2,3-d]pyrimidin-4-one; 5-[4-chloro-3-(trifluoromethyl)phenyl]-3-[3-(3-fluoropyrrolidin-1-yl)-3-oxopropyl]-3H,4H-thieno[2,3-d]pyrimidin-4-one; 5-[4-chloro-3-(trifluoromethyl)phenyl]-3-[3-oxo-3-(pyrrolidin-1-yl)propyl]-3H,4H-thieno[2,3-d]pyrimidin-4-one; N-[5-(3-chloro-4-fluorophenyl)-4-oxo-3H,4H-thieno[2,3-d]pyrimidin-3-yl]pyrrolidine-1-carboxamide; 5-(3-chloro-4-fluorophenyl)-3-[1-oxo-1-(pyrrolidin-1-yl)propan-2-yl]-3H,4H-thieno[2,3-d]pyrimidin-4-one; 5-(3-chloro-4-fluorophenyl)-4-oxo-3H,4H-thieno[2,3-d]pyrimidin-3-yl pyrrolidine-1-carboxylate; 5-[4-chloro-3-(trifluoromethyl)phenyl]-3-[2-oxo-2-(pyrrolidin-1-yl)ethoxy]-3H,4H-thieno[2,3-d]pyrimidin-4-one; 5-[4-chloro-3-(trifluoromethyl)phenyl]-4-oxo-3H,4H-thieno[2,3-d]pyrimidin-3-yl pyrrolidine-1-carboxylate; 5-[4-chloro-3-(trifluoromethyl)phenyl]-3-{[2-oxo-2-(pyrrolidin-1-yl)ethyl]amino}-3H,4H-thieno[2,3-d]pyrimidin-4-one; N-{5-[4-chloro-3-(trifluoromethyl)phenyl]-4-oxo-3H,4H-thieno[2,3-d]pyrimidin-3-yl}pyrrolidine-1-carboxamide; 5-[4-chloro-3-(trifluoromethyl)phenyl]-3-[1-oxo-1-(pyrrolidin-1-yl)propan-2-yl]-3H,4H-thieno[2,3-d]pyrimidin-4-one; 5-[4-chloro-3-(trifluoromethyl)phenyl]-3-[2-(3-fluoropyrrolidin-1-yl)-2-oxoethyl]-3H,4H-thieno[2,3-d]pyrimidin-4-one; 3-[2-oxo-2-(pyrrolidin-1-yl)ethyl]-5-[3-(trifluoromethyl)phenyl]-3H,4H-thieno[2,3-d]pyrimidin-4-one; 5-[2-fluoro-5-(trifluoromethyl)phenyl]-3-[2-oxo-2-(pyrrolidin-1-yl)ethyl]-3H,4H-thieno[2,3-d]pyrimidin-4-one; 5-(2-chloro-4-fluorophenyl)-3-[2-oxo-2-(pyrrolidin-1-yl)ethyl]-3H,4H-thieno[2,3-d]pyrimidin-4-one; 5-(3,4-dichlorophenyl)-6-methyl-3-[2-oxo-2-(pyrrolidin-1-yl)ethyl]-3H,4H-thieno[2,3-d]pyrimidin-4-one; 5-(3-chloro-4-fluorophenyl)-6-methyl-3-[2-oxo-2-(pyrrolidin-1-yl)ethyl]-3H,4H-thieno[2,3-d]pyrimidin-4-one; 5-(2-chlorophenyl)-3-[2-oxo-2-(pyrrolidin-1-yl)ethyl]-3H,4H-thieno[2,3-d]pyrimidin-4-one; 3-[2-oxo-2-(pyrrolidin-1-yl)ethyl]-5-[3-(trifluoromethoxy)phenyl]-3H,4H-thieno[2,3-d]pyrimidin-4-one; 5-[2-methyl-4-(trifluoromethyl)phenyl]-3-[2-oxo-2-(pyrrolidin-1-yl)ethyl]-3H,4H-thieno[2,3-d]pyrimidin-4-one; 5-[4-chloro-3-(trifluoromethyl)phenyl]-6-methyl-3-[2-oxo-2-(pyrrolidin-1-yl)ethyl]-3H,4H-thieno[2,3-d]pyrimidin-4-one; 5-[4-(dimethylamino)phenyl]-3-[2-oxo-2-(pyrrolidin-1-yl)ethyl]-3H,4H-thieno[2,3-d]pyrimidin-4-one; 5-[4-fluoro-3-(trifluoromethyl)phenyl]-6-methyl-3-[2-oxo-2-(pyrrolidin-1-yl)ethyl]-3H,4H-thieno[2,3-d]pyrimidin-4-one; 5-[3,5-bis(trifluoromethyl)phenyl]-3-[2-oxo-2-(pyrrolidin-1-yl)ethyl]-3H,4H-thieno[2,3-d]

pyrimidin-4-one; 5-[4-fluoro-3-(trifluoromethyl)phenyl]-3-[2-oxo-2-(pyrrolidin-1-yl)ethyl]-3H,4H-thieno[2,3-d]pyrimidin-4-one; 3-[2-oxo-2-(pyrrolidin-1-yl)ethyl]-5-[2-(trifluoromethyl)pyridin-4-yl]-3H,4H-thieno[2,3-d]pyrimidin-4-one; 5-(2,3-dichlorophenyl)-3-[2-oxo-2-(pyrrolidin-1-yl)ethyl]-3H,4H-thieno[2,3-d]pyrimidin-4-one; 5-[2-methoxy-5-(trifluoromethyl)phenyl]-3-[2-oxo-2-(pyrrolidin-1-yl)ethyl]-3H,4H-thieno[2,3-d]pyrimidin-4-one; ethyl 2-[5-(4-chlorophenyl)-2-methyl-4-oxo-3H,4H-thieno[2,3-d]pyrimidin-3-yl]acetate; 5-(4-chlorophenyl)-2-methyl-3-[2-oxo-2-(pyrrolidin-1-yl)ethyl]-3H,4H-thieno[2,3-d]pyrimidin-4-one; 5-(4-chlorophenyl)-2-methyl-3-{2-oxo-2-[2-(trifluoromethyl)pyrrolidin-1-yl]ethyl}-3H,4H-thieno[2,3-d]pyrimidin-4-one; 5-[2-chloro-4-(trifluoromethyl)phenyl]-3-[2-oxo-2-(pyrrolidin-1-yl)ethyl]-3H,4H-thieno[2,3-d]pyrimidin-4-one; 5-(4-chlorophenyl)-3-{2-oxo-2-[2-(trifluoromethyl)pyrrolidin-1-yl]ethyl}-2-(trifluoromethyl)-3H,4H-thieno[2,3-d]pyrimidin-4-one; 5-(3,4-difluorophenyl)-3-[2-oxo-2-(pyrrolidin-1-yl)ethyl]-3H,4H-thieno[2,3-d]pyrimidin-4-one; 5-(4-methoxyphenyl)-3-[2-oxo-2-(pyrrolidin-1-yl)ethyl]-3H,4H-thieno[2,3-d]pyrimidin-4-one; 3-[2-oxo-2-(pyrrolidin-1-yl)ethyl]-5-(pyrimidin-5-yl)-3H,4H-thieno[2,3-d]pyrimidin-4-one; 5-(4-chlorophenyl)-6-methyl-3-{2-oxo-2-[2-(trifluoromethyl)pyrrolidin-1-yl]ethyl}-3H,4H-thieno[2,3-d]pyrimidin-4-one; 5-(4-chlorophenyl)-3-[2-oxo-2-(pyrrolidin-1-yl)ethyl]-2-(trifluoromethyl)-3H,4H-thieno[2,3-d]pyrimidin-4-one; 5-(5-fluoropyridin-3-yl)-3-[2-oxo-2-(pyrrolidin-1-yl)ethyl]-3H,4H-thieno[2,3-d]pyrimidin-4-one; 5-[2-fluoro-4-(trifluoromethyl)phenyl]-3-[2-oxo-2-(pyrrolidin-1-yl)ethyl]-3H,4H-thieno[2,3-d]pyrimidin-4-one; 5-(3,4-dichlorophenyl)-3-[2-oxo-2-(pyrrolidin-1-yl)ethyl]-3H,4H-thieno[2,3-d]pyrimidin-4-one; 5-(6-methoxypyridin-3-yl)-3-[2-oxo-2-(pyrrolidin-1-yl)ethyl]-3H,4H-thieno[2,3-d]pyrimidin-4-one; 5-(4-chlorophenyl)-6-methyl-3-[2-oxo-2-(pyrrolidin-1-yl)ethyl]-3H,4H-thieno[2,3-d]pyrimidin-4-one; 5-[4-chloro-3-(trifluoromethyl)phenyl]-3-[2-oxo-2-(pyrrolidin-1-yl)ethyl]-3H,4H-thieno[2,3-d]pyrimidin-4-one; 5-(4-tert-butylphenyl)-3-[2-oxo-2-(pyrrolidin-1-yl)ethyl]-3H,4H-thieno[2,3-d]pyrimidin-4-one; 3-[2-oxo-2-(pyrrolidin-1-yl)ethyl]-5-[4-(trifluoromethoxy)phenyl]-3H,4H-thieno[2,3-d]pyrimidin-4-one; 5-(1-methyl-1H-pyrazol-5-yl)-3-[2-oxo-2-(pyrrolidin-1-yl)ethyl]-3H,4H-thieno[2,3-d]pyrimidin-4-one; 4-{4-oxo-3-[2-oxo-2-(pyrrolidin-1-yl)ethyl]-3H,4H-thieno[2,3-d]pyrimidin-5-yl}benzonitrile; 5-(3-fluorophenyl)-3-[2-oxo-2-(pyrrolidin-1-yl)ethyl]-3H,4H-thieno[2,3-d]pyrimidin-4-one; 5-(3-chloro-4-fluorophenyl)-3-[2-oxo-2-(pyrrolidin-1-yl)ethyl]-3H,4H-thieno[2,3-d]pyrimidin-4-one; 3-[2-oxo-2-(pyrrolidin-1-yl)ethyl]-5-(pyridin-4-yl)-3H,4H-thieno[2,3-d]pyrimidin-4-one; 5-(4-chloro-3-fluorophenyl)-3-[2-oxo-2-(pyrrolidin-1-yl)ethyl]-3H,4H-thieno[2,3-d]pyrimidin-4-one; 5-(4-methylphenyl)-3-{2-oxo-2-[2-(trifluoromethyl)pyrrolidin-1-yl]ethyl}-3H,4H-thieno[2,3-d]pyrimidin-4-one; 5-(4-fluorophenyl)-3-{2-oxo-2-[2-(trifluoromethyl)pyrrolidin-1-yl]ethyl}-3H,4H-thieno[2,3-d]pyrimidin-4-one; 3-{2-oxo-2-[2-(trifluoromethyl)pyrrolidin-1-yl]ethyl}-5-[4-(trifluoromethyl)phenyl]-3H,4H-thieno[2,3-d]pyrimidin-4-one; 3-[2-oxo-2-(piperidin-1-yl)ethyl]-5-[4-(trifluoromethyl)phenyl]-3H,4H-thieno[2,3-d]pyrimidin-4-one; 5-(4-methylphenyl)-3-[2-oxo-2-(pyrrolidin-1-yl)ethyl]-3H,4H-thieno[2,3-d]pyrimidin-4-one; 5-(4-fluorophenyl)-3-[2-oxo-2-(piperidin-1-yl)ethyl]-3H,4H-thieno[2,3-d]pyrimidin-4-one; 5-(4-fluorophenyl)-3-[2-oxo-2-(pyrrolidin-1-yl)ethyl]-3H,4H-thieno[2,3-d]pyrimidin-4-one; 6-(4-chlorophenyl)-3-[2-(4,4-difluoropiperidin-1-yl)-2-oxoethyl]-3H,4H-thieno[2,3-d]pyrimidin-4-one; 6-(4-chlorophenyl)-3-[2-(morpholin-4-yl)-2-oxoethyl]-3H,4H-thieno[2,3-d]pyrimidin-4-one; 5-(4-methylphenyl)-3-[2-oxo-2-(piperidin-1-yl)ethyl]-3H,4H-thieno[2,3-d]pyrimidin-4-one; 3-[2-oxo-2-(pyrrolidin-1-yl)ethyl]-5-[4-(trifluoromethyl)phenyl]-3H,4H-thieno[2,3-d]pyrimidin-4-one; 2-[6-(4-chlorophenyl)-4-oxo-3H,4H-thieno[2,3-d]pyrimidin-3-yl]-N-cyclopropylacetamide; 6-(4-chlorophenyl)-3-[2-oxo-2-(piperidin-1-yl)ethyl]-3H,4H-thieno[2,3-d]pyrimidin-4-one; 5-(4-chlorophenyl)-3-[2-(3-fluoropyrrolidin-1-yl)-2-oxoethyl]-3H,4H-thieno[2,3-d]pyrimidin-4-one; 6-(4-chlorophenyl)-3-[2-oxo-2-(pyrrolidin-1-yl)ethyl]-3H,4H-thieno[2,3-d]pyrimidin-4-one; 5-(4-chlorophenyl)-3-[2-(4-hydroxy-4-phenylpiperidin-1-yl)-2-oxoethyl]-3H,4H-thieno[2,3-d]pyrimidin-4-one; 5-(4-chlorophenyl)-3-[2-(4,4-difluoropiperidin-1-yl)-2-oxoethyl]-3H,4H-thieno[2,3-d]pyrimidin-4-one; 2-[5-(4-chlorophenyl)-4-oxo-3H,4H-thieno[2,3-d]pyrimidin-3-yl]-N,N-diethylacetamide; 5-(4-chlorophenyl)-3-[2-(2,6-dimethylpiperidin-1-yl)-2-oxoethyl]-3H,4H-thieno[2,3-d]pyrimidin-4-one; 5-(4-chlorophenyl)-3-{2-oxo-2-[2-(trifluoromethyl)pyrrolidin-1-yl]ethyl}-3H,4H-thieno[2,3-d]pyrimidin-4-one; 5-(4-chlorophenyl)-3-{2-[(2S)-2-methylpyrrolidin-1-yl]-2-oxoethyl}-3H,4H-thieno[2,3-d]pyrimidin-4-one; 2-[5-(4-chlorophenyl)-4-oxo-3H,4H-thieno[2,3-d]pyrimidin-3-yl]-N-cyclobutylacetamide; 5-(4-chlorophenyl)-3-[2-oxo-2-(piperidin-1-yl)ethyl]-3H,4H-thieno[2,3-d]pyrimidin-4-one; 2-[5-(4-chlorophenyl)-4-oxo-3H,4H-thieno[2,3-d]pyrimidin-3-yl]-N-(1-methylpyrrolidin-3-yl)acetamide; 5-(4-chlorophenyl)-3-[2-(3-hydroxypyrrolidin-1-yl)-2-oxoethyl]-3H,4H-thieno[2,3-d]pyrimidin-4-one; 2-[5-(4-chlorophenyl)-4-oxo-3H,4H-thieno[2,3-d]pyrimidin-3-yl]-N-cyclopropylacetamide; 5-(4-chlorophenyl)-3-[2-(morpholin-4-yl)-2-oxoethyl]-3H,4H-thieno[2,3-d]pyrimidin-4-one; 5-(4-chlorophenyl)-3-[2-(4-methylpiperazin-1-yl)-2-oxoethyl]-3H,4H-thieno[2,3-d]pyrimidin-4-one; 5-(4-chlorophenyl)-3-[2-(4-fluoropiperidin-1-yl)-2-oxoethyl]-3H,4H-thieno[2,3-d]pyrimidin-4-one; 5-(4-chlorophenyl)-3-[2-(4-hydroxypiperidin-1-yl)-2-oxoethyl]-3H,4H-thieno[2,3-d]pyrimidin-4-one; 5-(5-chloro-6-fluoropyridin-3-yl)-3-[2-(3,4-difluoropyrrolidin-1-yl)-2-oxoethyl]-3H,4H-thieno[2,3-d]pyrimidin-4-one; 5-(5,6-dichloropyridin-3-yl)-3-[2-(3,4-difluoropyrrolidin-1-yl)-2-oxoethyl]-3H,4H-thieno[2,3-d]pyrimidin-4-one; 5-[6-chloro-5-(trifluoromethyl)pyridin-3-yl]-3-[2-(3,4-difluoropyrrolidin-1-yl)-2-oxoethyl]-3H,4H-thieno[2,3-d]pyrimidin-4-one; or a pharmaceutically acceptable salt, stereoisomer, or prodrug thereof.

8. A method of treating Alzheimer's disease in a patient in need thereof, comprising administering to the patient an effective amount of a compound represented by Formula II:

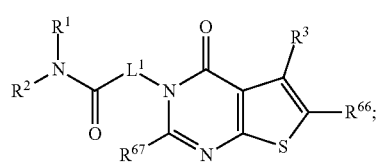

Formula II or a pharmaceutically acceptable salt, stereoisomer or prodrug thereof, wherein:

$L^1$ is selected from the group consisting of —($CR^{11}R^{22}$)$_n$—, —O—, —$NR^a$—, —($CR^{11}R^{22}$)$_n NR^a$—, —($CR^{11}R^{22}$)$_n$O—, and —H(C=N)—;

$R^{11}$ and $R^{22}$ are each independently selected for each occurrence from the group consisting of hydrogen and $C_{1-4}$alkyl;

n is 1 or 2;

$R^1$ and $R^2$, together with the nitrogen to which they are attached, form a 4-6 membered heterocyclic ring substituted on a carbon not adjacent to the nitrogen by one, two or more substituents each independently selected from the group consisting of halogen, cyano, oxo, hydroxyl and $C_{1-6}$alkyl (optionally substituted by one, two or three halogens);

$R^3$ is selected from the group consisting of phenyl, napthyl, heteroaryl, heterocyclyl and $C_{3-6}$cycloalkyl, wherein $R^3$ is optionally substituted with one, two or three substituents each independently selected from $C_{1-4}$alkyl, halogen, hydroxyl, cyano, $C_{1-4}$alkoxy, $C_{2-6}$alkenyl, $C_{2-6}$alkynyl, $C_{3-6}$cycloalkyl, $C_{1-6}$alkyl-S(O)$_2$—, $C_{1-6}$alkylcarbonyl, $R^aR^bN$—SO$_2$—, $NR^aR^b$, C(O)OH, $C_{1-4}$alkoxycarbonyl, and $NR^aR^b$carbonyl, wherein $C_{1-4}$alkyl, $C_{1-4}$alkoxy, $C_{2-6}$alkenyl, $C_{2-6}$alkynyl, $C_{3-6}$cycloalkyl, $C_{1-6}$alkyl-S(O)$_2$—, and $C_{1-6}$alkylcarbonyl may be optionally substituted by one or more substituents each independently selected from halogen, hydroxyl, cyano, and $NR^aR^b$;

$R^{66}$ and $R^{67}$ are each independently selected from the group consisting of hydrogen, halogen, $C_{1-4}$ alkyl (optionally substituted by one, two, three substituents selected from halogen, hydroxyl, cyano and $NR^aR^b$), and phenyl (optionally substituted by one, two or three halogens); and $R^a$ and $R^b$ are independently selected, for each occurrence, from the group consisting of: hydrogen, hydroxyl, and $C_{1-3}$alkyl; or $R^a$ and $R^b$, together with the nitrogen to which they are attached, form a 4-6 membered heterocyclic ring which may have an additional heteroatom selected from O, S, or N.

9. The method of claim 8, wherein $L^1$ is —CH$_2$—.

* * * * *